US008058014B2

(12) United States Patent
Gong et al.

(10) Patent No.: US 8,058,014 B2
(45) Date of Patent: Nov. 15, 2011

(54) METHOD OF DIAGNOSING OR PREDICTING DISEASE STATES IN A SUBJECT USING OMENTIN 1 AND OMENTIN 2

(75) Inventors: Da-Wei Gong, Olney, MD (US); John C. McLenithan, Baltimore, MD (US); Alan R. Shuldiner, Columbia, MD (US); Rong-Ze Yang, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 170 days.

(21) Appl. No.: 12/443,146

(22) PCT Filed: Sep. 29, 2007

(86) PCT No.: PCT/US2007/080025
§ 371 (c)(1),
(2), (4) Date: Apr. 14, 2009

(87) PCT Pub. No.: WO2008/042826
PCT Pub. Date: Apr. 10, 2008

(65) Prior Publication Data
US 2010/0021900 A1    Jan. 28, 2010

Related U.S. Application Data

(60) Provisional application No. 60/848,520, filed on Sep. 29, 2006.

(51) Int. Cl.
*G01N 33/53* (2006.01)
*C07K 1/14* (2006.01)
*C07K 1/16* (2006.01)
*C07K 1/30* (2006.01)

(52) U.S. Cl. ............ 435/7.1; 435/4; 436/501; 436/502; 436/503; 530/413; 530/417; 530/418

(58) Field of Classification Search ........................ None
See application file for complete search history.

(56) References Cited

U.S. PATENT DOCUMENTS

| | | | |
|---|---|---|---|
| 6,146,849 A | 11/2000 | Pierce et al. | |
| 6,342,581 B1 | 1/2002 | Rosen et al. | |
| 6,478,825 B1 | 11/2002 | Winterbottom et al. | |
| 6,524,820 B1 * | 2/2003 | Pierce et al. | 435/69.1 |
| 6,635,255 B1 | 10/2003 | Bruck et al. | |
| 7,022,493 B2 | 4/2006 | Issakani et al. | |
| 7,312,197 B2 | 12/2007 | Gong et al. | |
| 7,550,435 B2 | 6/2009 | Gong et al. | |
| 2002/0173635 A1 | 11/2002 | Jacobs et al. | |
| 2003/0064412 A1 | 4/2003 | Fischer et al. | |
| 2003/0082533 A1 | 5/2003 | Yue et al. | |
| 2004/0044191 A1 | 3/2004 | Fischer et al. | |
| 2004/0220099 A1 | 11/2004 | Gong et al. | |
| 2005/0032166 A1 | 2/2005 | Chen et al. | |
| 2005/0112675 A1 | 5/2005 | Kochan et al. | |

FOREIGN PATENT DOCUMENTS

| | | |
|---|---|---|
| WO | 99/49033 | 9/1999 |
| WO | 99/60161 | 11/1999 |
| WO | 00/05367 | 2/2000 |
| WO | 00/66708 | 11/2000 |
| WO | 00/73454 A1 | 12/2000 |
| WO | 01/16318 | 3/2001 |
| WO | 01/68848 A2 | 9/2001 |

OTHER PUBLICATIONS http://en.wikipedia.org/wiki/Obesity; accessed on Mar. 12, 2011.*
Yang et al., "cDNA Cloning, Genomic Structure, Chromosomal Mapping, and Functional Expression of a Novel Human Alanine Aminotransferase," Genomics, Mar. 2002, 79(3), pp. 445-450.
Kashiwagi et al., "In Vitro Insulin Resistance of Human Adipocytes Isolated From Subjects with Noninsulin-Dependent Diabetes Mellitus," J. Clin. Invest., Oct. 1983, 72(4), pp. 1246-1254.
Tsuji et al., "Human Intelectin is a Novel Soluble Lectin That Recognizes Galactofuranose in Carbohydrate Chains of Bacterial Cell Wall," The Journal of Biological Chemistry, Jun. 2001, 276(26), pp. 23456-23463.
Lee et al., "Human Homologs of the Xenopus Oocyte Cortical Granule Lectin XL35," Glycobiology, 2001, 11(1), pp. 65-73.
Suzuki et al., "Molecular Cloning and Functional Expression of a Human Intestinal Lactoferrin Receptor," Biochemistry, 2001, 40, pp. 15771-15779.
Komiya et al., "Cloning of the Novel Gene Intelectin, Which is Expressed in Intestinal Paneth Cells in Mice," Biochemical and Biophysical Research Communication, 1998, 251, pp. 759-762.
Altschul et al., Gapped BLAST and PSI-BLAST: A New Generation of Protein Database Search Programs, Nucleic Acids Research, 1997, 25, pp. 3389-3402.
NCBI Database Accession No. AAS49907, May 19, 2006.
Yang et al., Identification of omentin as a novel depot-specific adipokine in human adipose tissue: possible role in modulating insulin action. *Am J Physiol Endocrinol Metab* 290: E 1253-E1261, 2006.
De Souza Batista et al., Omentin Plasma Levels and Gene Expression Are Decreased in Obesity. *Diabetes* 56:1655-1661 (2007).
Kralisch, S., et al. Adipokines and Adipocyte Targets in the Future Management of Obesity and the Metabolic Syndrome. Mini-Reviews in Medicinal Chemistry, 2007, 7:39-45.
Wurm, S., et al. Plasma levels of leptin, omentin, collagenous repeat-containing sequence of 26-kDa protein (CORS-26) and adiponectin before and after oral glucose uptake in slim adults. Cardiovascular Diabetology 2007, 6:1-7.
Sharma AM: Adipose Tissue: a mediator of cardiovascular disease. Int J Obes 26:Suppl 4:S5-S7, 2002.

(Continued)

*Primary Examiner* — Christine J Saoud
(74) *Attorney, Agent, or Firm* — Roylance, Abrams, Berdo & Goodman LLP

(57) ABSTRACT

The present invention is directed to methods of diagnosing a disease or predicting an increased risk of a disease, such as obesity, obesity-dependent subacute inflammation, atherosclerosis, cardiovascular disease and a metabolic disease, by determining the levels of omentin 1 and 2 protein in a subject, or by determining the levels of omentin 1 and 2 gene expression in a subject. The present invention is also directed to methods of disease treatment using omentin 1 protein and omentin 2 protein.

6 Claims, 24 Drawing Sheets

OTHER PUBLICATIONS

Felber JP, Golay A: Pathways from obesity to diabetes. Int J Obes 26:Suppl 2:S39-S45, 2002.

Kershaw EE, Flier JS: Adipose tissue as an endocrine organ. J Clin Endocrinol Metab 89:2548-2556, 2004.

Galuska DA, Khan LK: Obesity: a public health perspective. In Present Knowledge in Nutrition. 8th ed. Ed. International Life Sciences Institute, 2001, p. 531-542.

Bjorntorp P: Metabolic implications of body fat distribution. Diabetes Care 14:1132-1143, 1991.

Brunzell JD, Hokanson JE: Dyslipidemia of central obesity and insulin resistance. Diabetes Care 22:Suppl 3:C10-13, 1999.

Lemieux S: Contribution of visceral obesity to the insulin resistance syndrome. Can J Appl Physiol 26:273-290, 2001.

Johnson JA, Fried SK, Pi-Sunyer FX, Albu JB: Impaired insulin action in subcutaneous adipocytes from women with visceral obesity. Am J Physiol Endocrinol Metab 280:E40-E9, 2001.

Van Pelt RE, Jankowski CM, Gozansky WS, Schwartz RS, Kohrt WM: Lower-body adiposity and metabolic protection in postmenopausal women. J Clin Endocrinol Metab 90:4573-4578, 2005.

Fried SK, Ross, RJR: The biology of visceral adipose tissue. In Handbook of Obesity, 2nd edition, Edited by Bray GA, Bouchard C, James WPT, 2005, p. 589-614.

Schaffler A, Neumeier M, Hertarth H, Furst A, Scholmerich J, Buchler C: Genomin structure of human omentin, a new adipocytokine expressed in omental adipose tissue. Biochim Biophys Acta 1732:96-102, 2005.

Kralisch S, Klein J, Bluher M, Paschke R, Stumvoll M, Fasshauer M: Therapeutic perspectives of adipocytokines. Expert Opin Pharmacother 6:863-72, 2005.

Fu M, et al. Systematic analysis of omentin 1 and omentin 2 on 1q23 as candidate genes for type 2 diabetes in the Old Order Amish (Abstract). Diabetes 53: A59, 2004.

St Jean P, et al. Association between diabetes, obesity, glucose and insulin levels in the Old Older Amish and SNPs on 1q21-23. Am J Hum Genet 67:332, 2000.

Elbein SC, et al. A genome-wide search for type 2 diabetes susceptibility genes in Utah Caucasians. Diabetes 48:1175-1182, 1999.

Hanson RL, et al. An autosomal genomic scan for loci linked to type II diabetes mellitus and body-mass index in Pima Indians. Am J Hum Genet 63:1130-1138, 1998.

Vionnet N, et al. Genomewide search for type 2 diabetes-susceptibility genes in French whites: evidence for a novel susceptibility locus for early-onset diabetes on chromosome 3q27-qter and independent replication of a type 2-diabetes locus on chromosome 1q21-q24. Am J Hum Genet 67:1470-1480, 2000.

Wiltshire S, et al. A genomewide scan for loci predisposing to type 2 diabetes in a U.K. population (the Diabetes UK Warren 2 Repository): analysis of 573 pedigrees provides independent replication of a susceptibility locus on chromosome 1q. Am J Hum Genet 69:553-569, 2001.

Hsueh WC, et al. Diabetes in the Old Order Amish: Characterization and heritability analysis of the Amish Family Diabetes Study. Diabetes Care 23:595-601, 2000.

Almasy L, Blangero J: Multipoint quantitative-trait linkage analysis in general pedigrees. Am J Hum Genet 62:1198-1211, 1998.

Stothard P: The Sequence Manipulation Suite: JavaScript programs for analyzing and formatting protein and DNA sequences. Biotechniques 28:1102-1104, 2000.

Montague CT, Prins JB, Sanders L, Digby JE, O'Rahilly S: Depot- and sex-specific differences in human leptin mRNA expression: implications for the control of regional fat distribution, Diabetes 46:342-347, 1997.

Alessi MC, Peiretti F, Morange P, Henry M, Nalbone G, Juhan-Vague I: Production of plasminogen activator inhibitor 1 by human adipose tissue: possible link between visceral fat accumulation and vascular disease. Diabetes 46:860-867, 1997.

Arita Y, et al. Paradoxical decrease of an adipose-specific protein, adiponectin, in obesity. Biochem Biophys Res Commun 257:79-83, 1999.

Yang WS, et al. Weight reduction increases plasma levels of an adipose-derived anti-inflammatory protein, adiponectin. J Clin Endocrinol Metab 86:3815-3819, 2001.

Weyer C, et al. Hypoadiponectinemia in obesity and type 2 diabetes: close association with insulin resistance and hyperinsulinemia. J Clin Endocrinol Metab 86:1930-1935, 2001.

Tschritter O, et al. Plasma adiponectin concentrations predict insulin sensitivity of both glucose and lipid metabolism. Diabetes 52:239-243, 2003.

Yamauchi T, et al. The fat-derived hormone adiponectin reverses insulin resistance associated with both lipoatrophy and obesity. Nat Med 7:941-946, 2001.

McLaughlin T, Abbasi F, Kim HS, Lamendola C, Schaaf P, Reaven G: Relationship between insulin resistance, weight loss, and coronary heart disease risk in healthy, obese women. Metabolism 50:795-800, 2001.

Matsubara M, Maruoka S, Katayose S: Decreased plasma adiponectin concentrations in women with dyslipidemia. J Clin Endocrinol Metab 87:2764-2769, 2002.

Pagano C, et al. Reduced plasma visfatin/pre B-cell colony enhancing factor in obesity is not related to insulin resistance in humans. J Clin Endocrinol Metab 91:3165-3170, 2006.

Ryan AS, Nicklas BJ: Reductions in plasma cytokine levels with weight loss improve insulin sensitivity in overweight and obese postmenopausal women. Diabetes Care 27:1699-1705, 2004.

Weisberg, S. P., et al. Obesity is associated with macrophage accumulation in adipose tissue. J Clin Invest 112, 1796-808, 2003.

Fukuhara A, et al. Visfatin: a protein secreted by visceral fat that mimics the effects of insulin. Science 307 (5708):426-430, 2005.

Berndt J, et al. Plasma visfatin concentrations and fat depot-specific mRNA expression in humans. Diabetes 54 (10):2911-6, 2005.

* cited by examiner

A

B

C

D

A

B

*Traits adjusted for age and gender; Leptin ln transformed for analysis*

*Traits adjusted for age and gender Triglycerides ln transformed for analysis*

*Traits adjusted for age and gender*

| Tissue | OM1/Cyc | OM2/Cyc | OM2 vs OM1 |
|---|---|---|---|
| om fat | 1.52 | 0.92 | 50 Fold < |
| sm int | 0.07 | 6.35 | 5 Fold > |
| heart | 0.36 | 0.024 | |
| lung | 0.12 | 1.15 | |
| skm | 0.003 | 0.0003 | |
| kidney | 0.003 | 0.004 | |
| pancreas | 0.001 | 0.006 | |
| ad. gland | 0.002 | 0.0003 | |
| brain | 0.0003 | 0.006 | |
| thymus | 0.034 | 0.002 | |
| thyroid | 0.004 | 0.001 | |
| liver | 0.0001 | 0.022 | |

SEQ ID NO:9

Agttaacaggctggctcggtggttcacgcccgtaatcctagcacttgggcaagctgag
gcaggaggatcaaggtcaggagttctggagtagcctgggtaacatggggagacccccgt
ttctacagaaaagaaaagagttttttttgttttttgttttttttgagatggagtttca
ctcttgttgcccaggctggagtgcaatggtgtgatctcggctcactgcaacctccgcc
tcctggattcaggtgattctcctgcctcagcctcctgagtagctgggattacaggcat
gcaccaccacgaccggctaattttgtattttagtagagacgggtttctccatgttg
gtcaggctggtctcgatcttttgacctcagatgatccacccacctcggcctcccaaag
tgctgggattacaggcgtgagccaccgcgcccagcccaaaaaaagagttttaataat
atgatgttgataattgtactgtggttatacatgacatattcctattattagaaaacac
a (c/t) agttggccaggcatggtggcttacacctataatcccagcacttgggaggccg
aggcaggtggatcacgaggtcacgagttcaagaccagcctggccaagatggcaaaacc
ccgtatctactaaaaatacaaaaattagctgggcgtggtggtgggtgcctgtaatccc
agttactcgggaggctgagacaggagaatcacttgaacctgggaggcgggggttgcag
taagctgagaccatgccattgcactccaacctgggtgacagagtgaggctctgtgtca
aaaacaaaacaaaataaaaaaaacccatacgcatttatttaaaggtaaaagcccatg
atgtatgtaccttaccttcaaatggttcagaaaaaaattttgtgtgtgtgggtgtatt
ttatatacatatatctatatatatagagagagagagagagaacacgaaagataaag
caaatggggtgaaatattaacaatagttgaatctaggtaaagggcatatatgtggctt
tatattattgttattttttgcaacatttaataaatttcaaattgtttctaaacagagtt
aataaaacaataaaattacagcaggatacatgcaataattagtgtttggacagtgtat
agt (g/t) ggacaaaggaaggatccatcagctttgtctggtgatgggggtgtcaggga
aggcctcatagagaaattggaggaaagattggaaggatgatgtcttcttttcccattt
atttattattattattattattattttgaggtgaagtcttgctctgttgcccagg
ctggagtgcagtggagcagtcttggctcactgcaacctccacctcctgggttcaagca
gttctcctgtctcagcctccagagtagctgggattacgggtgcacgccactgcaccca
gctaaattttgtattttagtagagacagggttgcaccatgttggctggtcttgaac
tcctgacctcaggtaatccgcccacctcggcctcccaaagcgctatgattataggtgt
gagccactgtgcctggccaattattattcttaattaattaatttattttcatgaggt
gtcacctcagtctaaaaggatgatttcttgacagagttgtgtctaggggggccagggca
tctgggggaggtgggagagggagaacgcaggggaggattgtgacctatccacgaatct
gattagatactgctacattgtatggcctgccttggcaaagcaggatgcccctcctcag
atggcgacagtcacctgtgtggccaggaacacagctccctgctcctccagccagtcgc
acgtcctttctcatttccacggtcccaggctcaggtaccctcagagggaagggcttca
gagggaggggctagcagcctaggctgctcagggttgggctgggcagggctcaggtggt
ttggctctccacagctctccacataaagggaccagcacttcacccttcatcaggatcc
tctGCAGGGGAGCTCCGAGTGTCCACAGGAAGGGAACTATCAGCTCCTGGCATCTGTA
AGGATGCTGTCCATGCTGgt

Figure 28

SEQ ID NO:10

<u>ATACCTGTGGTCTATGACTTTGGTGATGCTAAGAAGACTGCATCTTATTACTCACCGTATGG
TCAACG</u>tgagtgtttgctccctaagtccagtcataaatattttcttgtactcttggagaatg
gtggcaaataacaacaattaataattgctagtatttactgagcacttaaaatgcaccagact
cttgtcttggaacttaacatgattttgtgtcatttaattaccatgagaaaactatgaagtta
gaattgctgttatccccatttcacagcacgtaatcccaggtttcttcatcaccaccttgtat
actcttataattgtggggaaaagaaaaagagatcagactgttactgtgtctatgtagaaaga
agtagacataagagactccattttggtctgtgctgagaaaaattcttctgccttgagatgct
gttaatctgtaaccctaccccaaccctgtgctcacagagacatgtgctgtgttgactcacg
gtttaatggatttagggctgtgcaggatgtgctttgttaaacaagtgcttgaaggcagcatg
cttgttaaaggtcatcaccactctctaatctcaagtacccagggacacaatacactgcggaa
ggccgcagggacctctgtctaggaaagccaggtattgtccaaggtttctccccatgtgatag
cctgagatatggcctcgtgggaagggaaagacctgactgtccccagcccgacacccacaaa
gggtctgtgctgaggaggattagtaaaagaggaaggcctctttgcagttgagataagaggaa
ggcatctgtcttctgcttatccctgggcaatggaatgttttggtgtaaaacccgattgtatg
ttctatttactgagataggagaaaaccacttagggctggaggtgagacatgctggcggcaa
tactgcttttaatgcaccgagatgtttatgtatgtgcacgtcaaaagcacagcacctttc
ttaaccttgtttatgacacagacatttgttcacatgttttcctgctgaccctctcccacta
ttaccctattgtcctgccacgtcccctctctgagatggtagagataatgatcaataaatac
tgagggaactcagagactggtgctggtgcgggtcctccttatgctgagcgccagtcccctgg
gcccacttttctttctctatactttgtcgctgtgtctctttcttttctcagtctctcgttcc
acccaacgaggaacacccacaggtgtggaggggcaggccaccccttcaataatagttaagaa
aggtgcatacaaaacattagctgggcatgatggcgcatgcctgtaatcccagctcctcggg
aggctgaggcaggagaat<u>(c/t)</u>

METHOD OF DIAGNOSING OR PREDICTING DISEASE STATES IN A SUBJECT USING OMENTIN 1 AND OMENTIN 2

CROSS REFERENCE TO RELATED CASES

This application claims the benefit of U.S. Provisional Application Ser. No. 60/848,520, filed Sep. 29, 2006, which is incorporated herein by reference in its entirety.

STATEMENT REGARDING FEDERALLY SPONSORED RESEARCH

This invention was made in part with government support by National Institutes of Health Grant Nos. DK-620931983, AG20116 and P30DK072488, and the Veterans Administration, Geriatrics Research and Education Clinical Center (GRECC). The U.S. Government has certain rights in this invention.

BACKGROUND OF THE INVENTION

Adipose tissue, once considered simply a fuel storage depot, is now recognized as an endocrine tissue that communicates actively with the central nervous system and peripheral tissues, responding to and regulating various neuronal, metabolic and hormonal signals to participate in energy storage, fatty acid metabolism and glucose homeostasis (46, 47). Adipose tissue also plays an important role in the pathogenesis of obesity and its associated diseases such as type 2 diabetes, cardiovascular disease and dyslipidemia (metabolic syndrome).

Regional distribution of adipose tissue is an independent factor for the susceptibility to obesity-associated morbidities. Numerous epidemiological studies have firmly established that central obesity, the accumulation of intraabdominal (omental) fat, as compared with subcutaneous fat, is associated with a higher degree of risk for type 2 diabetes, cardiovascular disease, hypertension, and hyperlipidemia (48, 49). Many investigations have been undertaken to try to understand the reason why abdominal fat is more pathogenic and to study differences between omental and subcutaneous fat. Studies also suggest that these two adipose tissue depots differ in important ways. Omental adipose tissue is more metabolically active with respect to lipolysis and lipogenesis (50, 51). Abdominal fat pads secrete higher pro-inflammatory cytokines such as interleukin 6 (IL-6) (52), plasminogen activator inhibitor (PAI-1) (53), angiotensinogen (54), resistin (55) and exhibit greater apoptosis (56) than that found in subcutaneous fat pads. In contrast, leptin expression is higher in subcutaneous fat tissue than omental fat tissue (57, 58). Omental fat is also less insulin sensitive but more sensitive to beta-adrenergic stimulation (50). It is thought that these depot-specific variations in metabolism may explain features of metabolic syndrome. Because the pathophysiological basis of this syndrome is likely to be complex, several tissues, gene products and pathways may participate in the disease process.

Adipose tissue is composed of a number of different cell types in addition to the adipocytes themselves, such as preadipocytes, endothelial cells, mast cells, pericytes, fibroblasts, macrophages and inflammatory cells (59). These supporting non-adipocyte cells are collectively called stromal-vascular cells (SVC), the majority of which are preadipocytes and endothelial cells. Differing ratios of stromal-vascular cells, innervation, vascularization, anatomical location and metabolic demands may all contribute to the adipose depot-specific differences that are observed.

A variety of bioactive factors that impact energy metabolism, the immune system, angiogenesis and cardiovascular health are secreted by adipose tissue. These factors include leptin, tumor necrosis factor-alpha (TNF-alpha), plasminogen activator inhibitor-1 (PAI-1), IL-6, adiponectin/ACRP30/adipoQ, vascular endothelial growth factor (VEGF), basic fibroblast growth factor (bFGF) and resistin (55, 60, 61). Alterations of the levels of cell surface receptors for cytokines could induce changes in insulin action. Adiponectin, a bioactive factor that promotes insulin sensitivity, is decreased in obesity (62, 63). Adipocytes almost exclusively produce leptin and adiponectin (57) as well as large amounts of VEGF (64) and bFGF (65). However, non-adipose stromal-vascular cells produce the majority of PAI-1 (55) and essentially all IL-6 (55), TNF-alpha (Fried, unpublished observations) and resistin (55). Thus, the non-adipocyte cells in adipose tissue significantly contribute to the secretion of bioactive factors that are attributed to this endocrine organ. (74).

In a recent study on obesity, a chronic pathological condition, obesity was associated with increased macrophage infiltration of adipose tissue and production of TNF-alpha, a pro-inflammatory cytokine that causes insulin resistance (75). Endothelial cells of the adipose tissue stromal vasculature play an important role in obesity and obesity-related insulin resistance by secreting monocyte chemoattractant protein-1 (MCP-1) which promotes macrophage infiltration. Obesity is a risk factor for type 2 diabetes and cardiovascular disease (CVD) (1-4). Several studies have shown that visceral obesity, in particular, is strongly associated with insulin resistance, hyperglycemia, dyslipidemia and hypertension. Subcutaneous fat deposition has also been associated with decreased risk of cardiovascular disease in some studies (5-9).

Recently, studies of germ-free mice focused attention on the intestine and its role in the etiology of obesity. Germ-free mice exhibited 42% lower fat mass than their conventionally raised littermates with a normal intestinal microbiota. These intestinal symbiotic bacteria can affect the regulation of energy metabolism by inducing formation of more capillaries to increase absorption, increasing monosaccharide uptake from bacterial breakdown of indigestible polysaccharides which stimulates triglyceride (TG) production and suppressing angiopoietin-like protein-4 which allows increased lipoprotein lipase activity leading to increased fat storage (67, 68, 70). Thus, the control of nutrient flux through the intestine may be the first line of defense against obesity and insulin resistance and their pathophysiological consequences.

To aid in the control of this bacterial "organ", the intestine has developed secreted factors that are part of the innate immune system such as defensins, RELMb, and RegIII that prevent bacterial invasion of the intestinal mucosa, inflammation and increased intestinal permeability (71, 72). Intestinal inflammation, often caused by increased TNF-alpha, can cause intestinal insulin resistance resulting in overproduction of intestinal apolipoprotein B48 containing TG-rich particles (73). High fructose-induced intestinal insulin resistance also caused similar elevated TG flux across the intestine to create metabolic dyslipidemia (79). Although the intestine is not classically thought of as an insulin target tissue, many recent studies have utilized oral insulin to improve intestinal health, permeability and decrease plasma triglycerides and cholesterol (80). Oral insulin administration was shown to decrease atherosclerotic lesions in ApoE knockout mice (81).

In light of the divergent pathological nature of adipose tissue accumulation, it is of great interest to resolve the molecular differences between visceral and subcutaneous adipose tissue depots. Although anatomical location and vascularization are clearly different (10), the molecular basis of differences in metabolism and secretory profile between visceral (omental) and subcutaneous adipose tissues and their impact on whole body physiology are not completely understood. Indeed, understanding the life cycle of the adipocyte, tissue dynamics or fat depot-specific differences will involve gaining more insight into the complex stromal-vascular cell interactions and paracrine/endocrine environment in adipose tissue.

In the furtherance of such studies, two adipose-specific proteins have been identified. Initially, omentin 1 was shown to be a novel secreted factor that is detectable in human plasma and has human visceral fat depot-specific expression (86; 11-13; U.S. patent application Ser. No. 10/785,720 (U.S. patent application publication no. 2004/0220099)). Omentin 1 was named for its preferential expression in visceral (omental) rather than subcutaneous adipose tissue (11). Omentin 1 has been identified in other tissues at reduced expression levels and named intelectin (14), intestinal lactoferrin receptor (15) or endothelial lectin (16). It is expressed in intestinal Paneth cells (17), endothelial cells (16), as well as visceral adipose stromal-vascular cells (11). In vitro studies have shown that omentin increases insulin signal transduction by activating the protein kinase Akt/PKB, and enhancing insulin-stimulated glucose transport in isolated human adipocytes. Thus, omentin 1 may play a paracrine or endocrine role in modulating insulin sensitivity.

Omentin 2 has 83% amino acid identity with omentin 1 (16) and is also expressed preferentially in visceral fat although at much lower levels (87). Omentin 2 expression is highest in small intestine and lung but is not detected in the plasma (87). Preliminary studies (discussed herein) of omentin genetics indicate association of omentin 2 polymorphisms with metabolic syndrome traits and impaired glucose tolerance.

The two omentin genes, omentin 1 and omentin 2, are localized adjacent to each other in the 1q22-q23 chromosomal region (18) that has been previously associated with type 2 diabetes in several populations (19-23).

Another adipokine, visfatin/preB-cell colony enhancing factor, was reported to have visceral fat-specific expression and insulin-mimetic properties (83). However recent studies in humans have shown little difference between visfatin expression in visceral and subcutaneous adipose tissue depots, elevated visceral fat expression in obesity and no correlation with measures of insulin sensitivity (84, 85). Unlike the visfatin's insulin-mimetic properties, omentin was shown to augment insulin-stimulated glucose transport in 3T3-L1 adipocytes and isolated human adipocytes, thus, acting as an insulin-sensitizer (86). These data suggested that omentin secretion from visceral fat may positively impact insulin sensitivity and glucose homeostasis.

The evidence discussed above, and further presented herein, suggests a crucial relationship between the regulation of intestinal nutrient absorption and the metabolic responsiveness, endocrine function and development of adipose tissue. Strong genetic evidence points to omentin 2 as a metabolic syndrome susceptibility gene. It is critical to understand the role of omentin 2 in the intestine and its regulation. It is also equally important to understand the relationship between omentin 1 and 2. Both of these molecules have the potential to greatly impact visceral adipose metabolism and potentially affect whole body energy metabolism. Therefore, it is of great significance to determine the effect of obesity and inflammation on omentin expression so that an understanding of the role of these unique secreted factors in the dynamics of intestinal physiology, adipose biology, obesity and insulin resistance can be obtained. Furthermore, knowledge of the regulation of an omental fat-specific gene may offer insight into specifically targeting gene therapies to this depot, and will provide fundamental knowledge of 'adipose depot-specific' gene expression.

Obesity and subacute inflammation are associated with increased risk for development of chronic disease, including type 2 diabetes and cardiovascular disease (CVD). The prevalence of obesity among American men and women has increased dramatically in the past two decades. Thus, the obesity epidemic has major implications for health of the nation, and for predicted health care costs to society for treatment of chronic disease (76). Thus, further understanding of the mechanisms by which obesity alters or is altered by intestinal function, adipose tissue metabolism/endocrine function is a particularly important research priority. Understanding the mechanisms linking obesity and inflammation to altered adipose tissue, intestinal and whole body metabolism may lead to the development of therapeutic agents or interventions that can prevent the deleterious consequences of increased adiposity or to prevent the development of obesity per se.

SUMMARY OF THE INVENTION

According to a first embodiment, the present invention is directed to methods of diagnosing disease in a subject comprising: (a) determining the amount of omentin 1 protein, omentin 2 protein, or both, in a sample from a subject, and (b) comparing the amount of omentin 1 protein, omentin 2 protein, or both, determined in (a) to a corresponding subject-matched control value determined for a population of subjects without the disease, wherein when the amount of omentin 1 protein, omentin 2 protein, or both, determined in (a) is less than the corresponding subject-matched control value, the subject is diagnosed as having the disease.

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

In a preferred embodiment, the present invention is directed to a method of diagnosing obesity, obesity-dependent subacute inflammation, atherosclerosis, cardiovascular disease or a metabolic disease in a subject comprising: (a) determining the amount of omentin 1 protein in a sample from a subject, and (b) comparing the amount of omentin 1 protein determined in (a) to a corresponding subject-matched control value determined for a population of subjects without obesity, obesity-dependent subacute inflammation, atherosclerosis, cardiovascular disease or a metabolic disease, wherein when the amount of omentin 1 protein determined in (a) is less than the corresponding subject-matched control value, the subject is diagnosed as having obesity, obesity-dependent subacute inflammation, atherosclerosis, cardiovascular disease or a metabolic disease.

In a further preferred embodiment, the present invention is directed to a method of diagnosing obesity, obesity-dependent subacute inflammation, atherosclerosis, cardiovascular disease or a metabolic disease in a subject comprising: (a) determining the amount of omentin 2 protein in a sample from a subject, and (b) comparing the amount of omentin 2 protein determined in (a) to a corresponding subject-matched control value determined for a population of subjects without obesity, obesity-dependent subacute inflammation, atherosclerosis, cardiovascular disease or a metabolic disease, wherein when the amount of omentin 2 protein determined in (a) is less than the corresponding subject-matched control value, the subject is diagnosed as having obesity, obesity-dependent subacute inflammation, atherosclerosis, cardiovascular disease or a metabolic disease.

In each of these embodiments, the sample may be one or more of a whole blood sample, a serum sample, a plasma sample, a stool sample, a small intestine tissue sample, a visceral adipose tissue sample and a subcutaneous adipose tissue sample.

In each of these embodiments, the amount of protein may be determined via chromatography, mass spectroscopy, or an immune-based assay, such as western blot analysis, ELISA or RIA.

In each of these embodiments, the difference between the amount of omentin 1 protein, omentin 2 protein, or both, determined in (a) and the corresponding subject-matched control value may be statistically significant.

In the preferred embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a second embodiment, the present invention is directed to methods of predicting an increased risk of a disease in a subject comprising: (a) determining the amount of omentin 1 protein, omentin 2 protein, or both, in a sample from a subject, and (b) comparing the amount of omentin 1 protein, omentin 2 protein, or both, determined in (a) to a corresponding subject-matched control value determined for a population of subjects without the disease, wherein when the amount of omentin 1 protein, omentin 2 protein, or both, determined in (a) is less than the corresponding subject-matched control value, the subject is predicted to have an increased risk of the disease.

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

In a preferred embodiment, the present invention is directed to a method of predicting an increased risk of obesity, obesity-dependent subacute inflammation, atherosclerosis, cardiovascular disease or a metabolic disease in a subject comprising: (a) determining the amount of omentin 1 protein in a sample from a subject, and (b) comparing the amount of omentin 1 protein determined in (a) to a corresponding subject-matched control value determined for a population of subjects without obesity, obesity-dependent subacute inflammation, atherosclerosis, cardiovascular disease or a metabolic disease, wherein when the amount of omentin 1 protein determined in (a) is less than the corresponding subject-matched control value, the subject is predicted to have an increased risk of obesity, obesity-dependent subacute inflammation, atherosclerosis, cardiovascular disease or a metabolic disease.

In a further preferred embodiment, the present invention is directed to a method of predicting an increased risk of obesity, obesity-dependent subacute inflammation, atherosclerosis, cardiovascular disease or a metabolic disease in a subject comprising: (a) determining the amount of omentin 2 protein in a sample from a subject, and (b) comparing the amount of omentin 2 protein determined in (a) to a corresponding subject-matched control value determined for a population of subjects without obesity, obesity-dependent subacute inflammation, atherosclerosis, cardiovascular disease or a metabolic disease, wherein when the amount of omentin 2 protein determined in (a) is less than the corresponding subject-matched control value, the subject is predicted to have an increased risk of obesity, obesity-dependent subacute inflammation, atherosclerosis, cardiovascular disease or a metabolic disease.

In each of these embodiments, the sample may be one or more of a whole blood sample, a serum sample, a plasma sample, a stool sample, a small intestine tissue sample, a visceral adipose tissue sample and a subcutaneous adipose tissue sample.

In each of these embodiments, the amount of protein may be determined via chromatography, mass spectroscopy, or an immune-based assay, such as western blot analysis, ELISA or RIA.

In each of these embodiments, the difference between the amount of omentin 1 protein, omentin 2 protein, or both, determined in (a) and the corresponding subject-matched control value may be statistically significant.

In the preferred embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a third embodiment, the present invention is directed to methods of diagnosing a disease in a subject comprising: (a) determining the level of omentin 1 gene expression, omentin 2 gene expression, or both, in a sample from a subject, and (b) comparing the level of omentin 1 gene expression, omentin 2 gene expression, or both, determined in (a) to a corresponding subject-matched control value determined for a population of subjects without the disease, wherein when the level of omentin 1 gene expression, omentin 2 gene expression, or both, determined in (a) is less than the corresponding subject-matched control value, the subject is diagnosed as having the disease.

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

In this embodiment, the sample may be one or more of a whole blood sample, a serum sample, a plasma sample, a stool sample, a small intestine tissue sample, a visceral adipose tissue sample and a subcutaneous adipose tissue sample.

In this embodiment, the level of gene expression is determined by RT-PCR, branched DNA assay, or array analysis.

In this embodiment, the difference between the level of omentin 1 gene expression, omentin 2 gene expression, or both, determined in (a) and the corresponding subject-matched control value may be statistically significant.

In a preferred embodiment, the present invention is directed to a method of diagnosing obesity, obesity-dependent subacute inflammation, atherosclerosis, cardiovascular disease or a metabolic disease in a subject comprising: (a) determining the level of omentin 1 gene expression in a sample from a subject, and (b) comparing the level of omentin 1 gene expression determined in (a) to a corresponding subject-matched control value determined for a population of subjects without obesity, obesity-dependent subacute inflammation, atherosclerosis, cardiovascular disease or a metabolic disease, wherein when the level of omentin 1 gene expression determined in (a) is less than the corresponding subject-matched control value, the subject is diagnosed as having obesity, obesity-dependent subacute inflammation, atherosclerosis, cardiovascular disease or a metabolic disease.

In a further preferred embodiment, the present invention is directed to a method of diagnosing obesity, obesity-dependent subacute inflammation, atherosclerosis, cardiovascular disease or a metabolic disease in a subject comprising: (a) determining the level of omentin 2 gene expression in a sample from a subject, and (b) comparing the level of omentin 2 gene expression determined in (a) to a corresponding subject-matched control value determined for a population of subjects without obesity, obesity-dependent subacute inflammation, atherosclerosis, cardiovascular disease or a metabolic disease, wherein when the level of omentin 2 gene expression determined in (a) is less than the corresponding subject-matched control value, the subject is diagnosed as having obesity, obesity-dependent subacute inflammation, atherosclerosis, cardiovascular disease or a metabolic disease.

In each of these embodiments, the sample may be one or more of a whole blood sample, a serum sample, a plasma sample, a stool sample, a small intestine tissue sample, a visceral adipose tissue sample and a subcutaneous adipose tissue sample.

In each of these embodiments, the level of gene expression is determined by RT-PCR, branched DNA assay or array analysis.

In each of these embodiments, the difference between the level of omentin 1 gene expression, omentin 2 gene expression, or both, determined in (a) and the corresponding subject-matched control value may be statistically significant.

In the preferred embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a fourth embodiment, the present invention is directed to methods of predicting an increased risk of a disease in a subject comprising: (a) determining the level of omentin 1 gene expression, omentin 2 gene expression, or both, in a sample from a subject, and (b) comparing the level of omentin 1 gene expression, omentin 2 gene expression, or both, determined in (a) to a corresponding subject-matched control value determined for a population of subjects without the disease, wherein when the level of omentin 1 gene expression, omentin 2 gene expression, or both, determined in (a) is less than the corresponding subject-matched control value, the subject is predicted to have an increased risk of the disease.

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

In a preferred embodiment, the present invention is directed to a method of predicting an increased risk of obesity, obesity-dependent subacute inflammation, atherosclerosis, cardiovascular disease or a metabolic disease in a subject comprising: (a) determining the level of omentin 1 gene expression in a sample from a subject, and (b) comparing the level of omentin 1 gene expression determined in (a) to a corresponding subject-matched control value determined for a population of subjects without obesity, obesity-dependent subacute inflammation, atherosclerosis, cardiovascular disease or a metabolic disease, wherein when the level of omentin 1 gene expression determined in (a) is less than the corresponding subject-matched control value, the subject is predicted to have an increased risk of obesity, obesity-dependent subacute inflammation, atherosclerosis, cardiovascular disease or a metabolic disease.

In a further preferred embodiment, the present invention is directed to a method of predicting an increased risk of obesity, obesity-dependent subacute inflammation, atherosclerosis, cardiovascular disease or a metabolic disease in a subject comprising: (a) determining the level of omentin 2 gene expression in a sample from a subject, and (b) comparing the level of omentin 2 gene expression determined in (a) to a corresponding subject-matched control value determined for a population of subjects without obesity, obesity-dependent subacute inflammation, atherosclerosis, cardiovascular disease or a metabolic disease, wherein when the level of omentin 2 gene expression determined in (a) is less than the corresponding subject-matched control value, the subject is predicted to have an increased risk of obesity, obesity-dependent subacute inflammation, atherosclerosis, cardiovascular disease or a metabolic disease.

In each of these embodiments, the sample may be one or more of a whole blood sample, a serum sample, a plasma sample, a stool sample, a small intestine tissue sample, a visceral adipose tissue sample and a subcutaneous adipose tissue sample.

In each of these embodiments, the level of gene expression is determined by RT-PCR, branched DNA assay or array analysis.

In each of these embodiments, the difference between the level of omentin 1 gene expression, omentin 2 gene expression, or both, determined in (a) and the corresponding subject-matched control value may be statistically significant.

In the preferred embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a fifth embodiment, the present invention is directed to methods of diagnosing a disease in a subject comprising, detecting at least one omentin 1 gene polymorphism or at least one omentin 2 gene polymorphism in a nucleic acid sample of a subject, wherein upon detection of the at least one omentin 1 gene polymorphism or the at least one omentin 2 gene polymorphism, the subject is diagnosed as having the disease.

In this embodiment, the polymorphism may be a single nucleotide polymorphism (SNP).

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a sixth embodiment, the present invention is directed to methods of diagnosing a disease in a subject comprising, detecting at least one omentin 2 gene polymorphism in a nucleic acid sample of a subject, wherein the at least one omentin 2 gene polymorphism is a SNP selected from the group consisting of Om-74938, Om-81237 and Om-81873, wherein upon detection of the at least one omentin 2 gene polymorphism, the subject is diagnosed as having the disease.

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

In a preferred embodiment, the present invention is directed to a method of diagnosing obesity, obesity-dependent subacute inflammation, atherosclerosis, cardiovascular disease or a metabolic disease in a subject comprising, detecting at least one omentin 2 gene polymorphism in a nucleic acid sample of a subject, wherein the at least one omentin 2 gene polymorphism is a SNP selected from the group consisting of Om-74938, Om-81237 and Om-81873, wherein upon detection of the at least one omentin 2 gene polymorphism, the subject is diagnosed as having obesity, obesity-dependent subacute inflammation, atherosclerosis, cardiovascular disease or a metabolic disease.

In each of these embodiments, the nucleic acid sample may be nucleic acid obtained from one or more of whole blood, serum, plasma, stool, small intestine tissue, visceral adipose tissue and subcutaneous adipose tissue from the subject. The nucleic acid may be DNA or RNA.

In the preferred embodiment, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a seventh embodiment, the present invention is directed to methods of predicting an increased risk of a disease in a subject comprising, detecting at least one omentin 1 gene polymorphism or at least one omentin 2 gene polymorphism in a nucleic acid sample of a subject, wherein upon detection of the at least one omentin 1 gene polymorphism or the at least one omentin 2 gene polymorphism, the subject is predicted to have an increased risk of the disease.

In this embodiment, the polymorphism may be a single nucleotide polymorphism (SNP).

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to an eighth embodiment, the present invention is directed to methods of predicting an increased risk of a disease in a subject comprising, detecting at least one omentin 2 gene polymorphism in a nucleic acid sample of a subject, wherein the at least one omentin 2 gene polymorphism is a SNP selected from the group consisting of Om-74938, Om-81237 and Om-81873, wherein upon detection of the at least one omentin 2 gene polymorphism, the subject is predicted to have an increased risk of the disease.

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

In a preferred embodiment, the present invention is directed to a method of predicting an increased risk of obesity, obesity-dependent subacute inflammation, atherosclerosis, cardiovascular disease or a metabolic disease in a subject comprising, detecting at least one omentin 2 gene polymorphism in a nucleic acid sample of a subject, wherein the at least one omentin 2 gene polymorphism is a SNP selected from the group consisting of Om-74938, Om-81237 and Om-81873, wherein upon detection of the at least one omentin 2 gene polymorphism, the subject is predicted to have an increased risk of obesity, obesity-dependent subacute inflammation, atherosclerosis, cardiovascular disease or a metabolic disease.

In each of these embodiments, the nucleic acid sample may be nucleic acid obtained from one or more of whole blood, serum, plasma, stool, small intestine tissue, visceral adipose tissue and subcutaneous adipose tissue from the subject. The nucleic acid may be DNA or RNA.

In the preferred embodiment, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a ninth embodiment, the present invention is directed to methods of treating a disease in a subject, comprising administering a therapeutically effective amount of omentin protein 1, omentin protein 2, or both, to a subject having a disease, thereby treating the disease in the subject.

In a related embodiment, the present invention is also directed to methods of treating a disease in a subject, comprising administering a therapeutically effective amount of a biologically active fragment of omentin protein 1, omentin protein 2, or both, to a subject having a disease, thereby treating the disease in the subject.

In these embodiments, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

In a preferred embodiment, the present invention is directed to a method of treating obesity, obesity-dependent subacute inflammation, atherosclerosis, cardiovascular disease or a metabolic disease in a subject, comprising administering a therapeutically effective amount of omentin protein 1, or a biologically active fragment thereof, to a subject having obesity, obesity-dependent subacute inflammation, atherosclerosis, cardiovascular disease or a metabolic disease, thereby treating obesity, obesity-dependent subacute inflammation, atherosclerosis, cardiovascular disease or a metabolic disease in a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of treating obesity, obesity-dependent subacute inflammation, atherosclerosis, cardiovascular disease or a metabolic disease in a subject, comprising administering a therapeutically effective amount of omentin protein 2, or a biologically active fragment thereof, to a subject having obesity, obesity-dependent subacute inflammation, atherosclerosis, cardiovascular disease or a metabolic disease, thereby treating obesity, obesity-dependent subacute inflammation, atherosclerosis, cardiovascular disease or a metabolic disease in a subject.

In each of these embodiments, the therapeutically effective amount of omentin protein 1, omentin protein 2, or the biologically active fragment, is administered systemically, to visceral adipose tissue, or to subcutaneous adipose tissue.

In the preferred embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a tenth embodiment, the present invention is directed to methods of reducing body mass index (BMI) of a subject, comprising administering a therapeutically effective amount of omentin protein 1, omentin protein 2, or both, to a subject, thereby reducing body mass index (BMI) of a subject.

In a related embodiment, the present invention is directed to methods of reducing body mass index (BMI) of a subject, comprising administering a therapeutically effective amount of a biologically active fragment of omentin protein 1, omentin protein 2, or both, to a subject, thereby reducing body mass index (BMI) of a subject.

In a preferred embodiment, the present invention is directed to a method of reducing body mass index (BMI) of a subject, comprising administering a therapeutically effective amount of omentin protein 1, or a biologically active fragment thereof, to a subject, thereby reducing body mass index (BMI) of a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of reducing body mass index (BMI) of a subject, comprising administering a therapeutically effective amount of omentin protein 2, or a biologically active fragment thereof, to a subject, thereby reducing body mass index (BMI) of a subject.

In each of these embodiments, the therapeutically effective amount of omentin protein 1, omentin protein 2, or the biologically active fragment, is administered systemically, to visceral adipose tissue, or to subcutaneous adipose tissue.

According to an eleventh embodiment, the present invention is directed to methods of reducing leptin in a subject, comprising administering a therapeutically effective amount of omentin protein 1, omentin protein 2, or both, to a subject, thereby reducing leptin in a subject.

In a related embodiment, the present invention is directed to methods of reducing leptin in a subject, comprising administering a therapeutically effective amount of a biologically active fragment of omentin protein 1, omentin protein 2, or both, to a subject, thereby reducing leptin in a subject.

In a preferred embodiment, the present invention is directed to a method of reducing leptin in a subject, comprising administering a therapeutically effective amount of omentin protein 1, or a biologically active fragment thereof, to a subject, thereby reducing leptin in a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of reducing leptin in a subject, comprising administering a therapeutically effective amount of omentin protein 2, or a biologically active fragment thereof, to a subject, thereby reducing leptin in a subject.

In each of these embodiments, the therapeutically effective amount of omentin protein 1, omentin protein 2, or the biologically active fragment, is administered systemically, to visceral adipose tissue, or to subcutaneous adipose tissue.

According to a twelfth embodiment, the present invention is directed to methods of treating insulin resistance in a subject, comprising administering a therapeutically effective amount of omentin protein 1, omentin protein 2, or both, to a subject having insulin resistance, thereby treating insulin resistance in a subject.

In a related embodiment, the present invention is directed to methods of treating insulin resistance in a subject, comprising administering a therapeutically effective amount of a biologically active fragment of omentin protein 1, omentin protein 2, or both, to a subject having insulin resistance, thereby treating insulin resistance in a subject.

In a preferred embodiment, the present invention is directed to a method of treating insulin resistance in a subject, comprising administering a therapeutically effective amount of omentin protein 1, or a biologically active fragment thereof, to a subject having insulin resistance, thereby treating insulin resistance in a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of treating insulin resistance in a subject, comprising administering a therapeutically effective amount of omentin protein 2, or a biologically active fragment thereof, to a subject having insulin resistance, thereby treating insulin resistance in a subject.

In each of these embodiments, the therapeutically effective amount of omentin protein 1, omentin protein 2, or the biologically active fragment, is administered systemically, to visceral adipose tissue, or to subcutaneous adipose tissue.

According to a thirteenth embodiment, the present invention is directed to methods of reducing inflammation in a subject, comprising administering a therapeutically effective amount of omentin protein 1, omentin protein 2, or both, to a subject, thereby reducing inflammation in a subject.

In a related embodiment, the present invention is directed to methods of reducing inflammation in a subject, comprising administering a therapeutically effective amount of a biologically active fragment of omentin protein 1, omentin protein 2, or both, to a subject, thereby reducing inflammation in a subject.

In a preferred embodiment, the present invention is directed to a method of reducing inflammation in a subject, comprising administering a therapeutically effective amount of omentin protein 1, or a biologically active fragment thereof, to a subject, thereby reducing inflammation in a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of reducing inflammation in a subject, comprising administering a therapeutically effective amount of omentin protein 2, or a biologically active fragment thereof, to a subject, thereby reducing inflammation in a subject.

In each of these embodiments, the therapeutically effective amount of omentin protein 1, omentin protein 2, or the biologically active fragment, is administered systemically, to visceral adipose tissue, or to subcutaneous adipose tissue.

In each of these embodiments, the inflammation is preferably subacute inflammation.

According to a fourteenth embodiment, the present invention is directed to methods of treating a disease in a subject, comprising administering a therapeutically effective amount of a vector comprising a polynucleotide encoding omentin protein 1, omentin protein 2, or both, to a subject having a disease, thereby treating the disease in a subject.

In a related embodiment, the present invention is directed to methods of treating a disease in a subject, comprising administering a therapeutically effective amount of a vector comprising a polynucleotide encoding a biologically active fragment of omentin protein 1, omentin protein 2, or both, to a subject having a disease, thereby treating the disease in a subject.

In this embodiment, the disease may be obesity, obesity-dependent subacute inflammation, atherosclerosis, a cardiovascular disease or a metabolic disease. In certain embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

In a preferred embodiment, the present invention is directed to a method of treating obesity, obesity-dependent subacute inflammation, atherosclerosis, cardiovascular disease or a metabolic disease in a subject, comprising administering a therapeutically effective amount of a vector comprising a polynucleotide encoding omentin protein 1, or a biologically active fragment thereof, to a subject having obesity, obesity-dependent subacute inflammation, atherosclerosis, cardiovascular disease or a metabolic disease, thereby treating obesity, obesity-dependent subacute inflammation, atherosclerosis, cardiovascular disease or a metabolic disease in a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of treating obesity, obesity-dependent subacute inflammation, atherosclerosis, cardiovascular disease or a metabolic disease in a subject, comprising administering a therapeutically effective amount of a vector comprising a polynucleotide encoding omentin protein 2, or a biologically active fragment thereof, to a subject having obesity, obesity-dependent subacute inflammation, atherosclerosis, cardiovascular disease or a metabolic disease, thereby treating obesity, obesity-dependent subacute inflammation, atherosclerosis, cardiovascular disease or a metabolic disease in a subject.

In each of these embodiments, the vector may be administered systemically, to visceral adipose tissue, or to subcutaneous adipose tissue.

In each of these embodiments, the vector further comprises a promoter sequence operably linked to the polynucleotide encoding omentin protein 1, omentin protein 2, or the biologically active fragment.

In the preferred embodiments, the cardiovascular disease may be coronary heart disease, cerebral arterial disease, peripheral vascular disease or peripheral artery disease. The metabolic disease may be a metabolic disease selected from the group consisting of pre-diabetes, type 1 diabetes, type 2 diabetes, hyperglycemia, hyperlipidemia, dyslipidemia, and hypertension.

According to a fifteenth embodiment, the present invention is directed to methods of reducing body mass index (BMI) of a subject, comprising administering a therapeutically effective amount of a vector comprising a polynucleotide encoding omentin protein 1, omentin protein 2, or both, to a subject, thereby reducing body mass index (BMI) of a subject.

In a related embodiment, the present invention is directed to methods of reducing body mass index (BMI) of a subject, comprising administering a therapeutically effective amount of a vector comprising a polynucleotide encoding a biologically active fragment of omentin protein 1, omentin protein 2, or both, to a subject, thereby reducing body mass index (BMI) of a subject.

In a preferred embodiment, the present invention is directed to a method of reducing body mass index (BMI) of a subject, comprising administering a therapeutically effective amount of a vector comprising a polynucleotide encoding omentin protein 1, or a biologically active fragment thereof, to a subject, thereby reducing body mass index (BMI) of a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of reducing body mass index (BMI) of a subject, comprising administering a therapeutically effective amount of a vector comprising a polynucleotide encoding omentin protein 2, or a biologically active fragment thereof, to a subject, thereby reducing body mass index (BMI) of a subject.

In each of these embodiments, the vector may be administered systemically, to visceral adipose tissue, or to subcutaneous adipose tissue.

In each of these embodiments, the vector further comprises a promoter sequence operably linked to the polynucleotide encoding omentin protein 1, omentin protein 2, or the biologically active fragment.

According to a sixteenth embodiment, the present invention is directed to methods of reducing leptin in a subject, comprising administering a therapeutically effective amount of a vector comprising a polynucleotide encoding omentin protein 1, omentin protein 2, or both, to a subject, thereby reducing leptin in a subject.

In a related embodiment, the present invention is directed to methods of reducing leptin in a subject, comprising administering a therapeutically effective amount of a vector comprising a polynucleotide encoding a biologically active fragment of omentin protein 1, omentin protein 2, or both, to a subject, thereby reducing leptin in a subject.

In a preferred embodiment, the present invention is directed to a method of reducing leptin in a subject, comprising administering a therapeutically effective amount of a vector comprising a polynucleotide encoding omentin protein 1, or a biologically active fragment thereof, to a subject, thereby reducing leptin in a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of reducing leptin in a subject, comprising administering a therapeutically effective amount of a vector comprising a polynucleotide encoding omentin protein 2, or a biologically active fragment thereof, to a subject, thereby reducing leptin in a subject.

In each of these embodiments, the vector may be administered systemically, to visceral adipose tissue, or to subcutaneous adipose tissue.

In each of these embodiments, the vector further comprises a promoter sequence operably linked to the polynucleotide encoding omentin protein 1, omentin protein 2, or the biologically active fragment.

According to a seventeenth embodiment, the present invention is directed to methods of treating insulin resistance in a subject, comprising administering a therapeutically effective amount of a vector comprising a polynucleotide encoding omentin protein 1, omentin protein 2, or both, to a subject having insulin resistance, thereby treating insulin resistance in a subject.

In a related embodiment, the present invention is directed to methods of treating insulin resistance in a subject, comprising administering a therapeutically effective amount of a vector comprising a polynucleotide encoding a biologically active fragment of omentin protein 1, omentin protein 2, or both, to a subject having insulin resistance, thereby treating insulin resistance in a subject.

In a preferred embodiment, the present invention is directed to a method of treating insulin resistance in a subject, comprising administering a therapeutically effective amount of a vector comprising a polynucleotide encoding omentin protein 1, or a biologically active fragment thereof, to a subject having insulin resistance, thereby treating insulin resistance in a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of treating insulin resistance in a subject, comprising administering a therapeutically effective amount of a vector comprising a polynucleotide encoding omentin protein 2, or a biologically active fragment thereof, to a subject having insulin resistance, thereby treating insulin resistance in a subject.

In each of these embodiments, the vector may be administered systemically, to visceral adipose tissue, or to subcutaneous adipose tissue.

In each of these embodiments, the vector further comprises a promoter sequence operably linked to the polynucleotide encoding omentin protein 1, omentin protein 2, or the biologically active fragment.

According to an eighteenth embodiment, the present invention is directed to methods of reducing inflammation in a subject, comprising administering a therapeutically effective amount of a vector comprising a polynucleotide encoding omentin protein 1, omentin protein 2, or both, to a subject having inflammation, thereby reducing inflammation in a subject.

In a related embodiment, the present invention is directed to methods of reducing inflammation in a subject, comprising administering a therapeutically effective amount of a vector comprising a polynucleotide encoding a biologically active fragment of omentin protein 1, omentin protein 2, or both, to a subject having inflammation, thereby reducing inflammation in a subject.

In a preferred embodiment, the present invention is directed to a method of reducing inflammation in a subject, comprising administering a therapeutically effective amount of a vector comprising a polynucleotide encoding omentin protein 1, or a biologically active fragment thereof, to a subject having inflammation, thereby reducing inflammation in a subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

In a further preferred embodiment, the present invention is directed to a method of reducing inflammation in a subject, comprising administering a therapeutically effective amount of a vector comprising a polynucleotide encoding omentin protein 2, or a biologically active fragment thereof, to a subject having inflammation, thereby reducing inflammation in a subject.

In each of these embodiments, the vector may be administered systemically, to visceral adipose tissue, or to subcutaneous adipose tissue.

In each of these embodiments, the vector further comprises a promoter sequence operably linked to the polynucleotide encoding omentin protein 1, omentin protein 2, or the biologically active fragment.

In each of these embodiments, preferably the inflammation is subacute inflammation.

According to a nineteenth embodiment, the present invention is directed to methods of inhibiting omentin 1 gene expression, omentin 2 gene expression, or both, in a subject, comprising administering to a subject in which inhibition of omentin 1 gene expression, omentin 2 gene expression, or both, is desired an effective amount of a proinflammatory cytokine, thereby inhibiting omentin 1 gene expression, omentin 2 gene expression, or both, in a subject.

In a preferred embodiment, the present invention is directed to a method of inhibiting omentin 1 gene expression in a subject, comprising administering to a subject in which inhibition of omentin 1 gene expression is desired an effective amount of a proinflammatory cytokine, thereby inhibiting omentin 1 gene expression in a subject.

In a further preferred embodiment, the present invention is directed to a method of inhibiting omentin 2 gene expression in a subject, comprising administering to a subject in which inhibition of omentin 2 gene expression is desired an effective amount of a proinflammatory cytokine, thereby inhibiting omentin 2 gene expression in a subject.

In each of these embodiments, the proinflammatory cytokine is IL-6 or TNF-alpha.

According to a twentieth embodiment, the present invention is directed to methods of increasing omentin 1 gene expression, omentin 2 gene expression, or both, in a subject, comprising administering to a subject in which an increase in omentin 1 gene expression, omentin 2 gene expression, or both, is desired an effective amount of IL-13, thereby increasing omentin 1 gene expression, omentin 2 gene expression, or both, in a subject.

In a preferred embodiment, the present invention is directed to a method of increasing omentin 1 gene expression in a subject, comprising administering to a subject in which an increase in omentin 1 gene expression is desired an effective amount of IL-13, thereby increasing omentin 1 gene expression in a subject.

In a further preferred embodiment, the present invention is directed to a method of increasing omentin 2 gene expression in a subject, comprising administering to a subject in which an increase in omentin 2 gene expression is desired an effective amount of IL-13, thereby increasing omentin 2 gene expression in a subject.

Other and further objects, features, and advantages will be apparent from the following description of the presently preferred embodiments of the invention, which are given for the purpose of disclosure.

BRIEF DESCRIPTION OF THE DRAWINGS

FIG. 24A—OM1/OM2. FIG. 24B—OM2/OM1.

FIG. 27 shows the location of the SNP Om-81237 (c/t) polymorphism and the SNP Om-81837 (g/t) polymorphism (both underlined and in bold) in relation to the translational start site (the ATG that is also underlined and in bold) of omentin 2 (SEQ ID NO:9).

FIG. 28 shows the location of the SNP Om-74938 c/t polymorphism (underlined and in bold) in relation to the end of exon 6 (SEQ ID NO: 10) of omentin 2 (in capital letters and underlined).

DETAILED DESCRIPTION OF THE INVENTION

Figure 1:
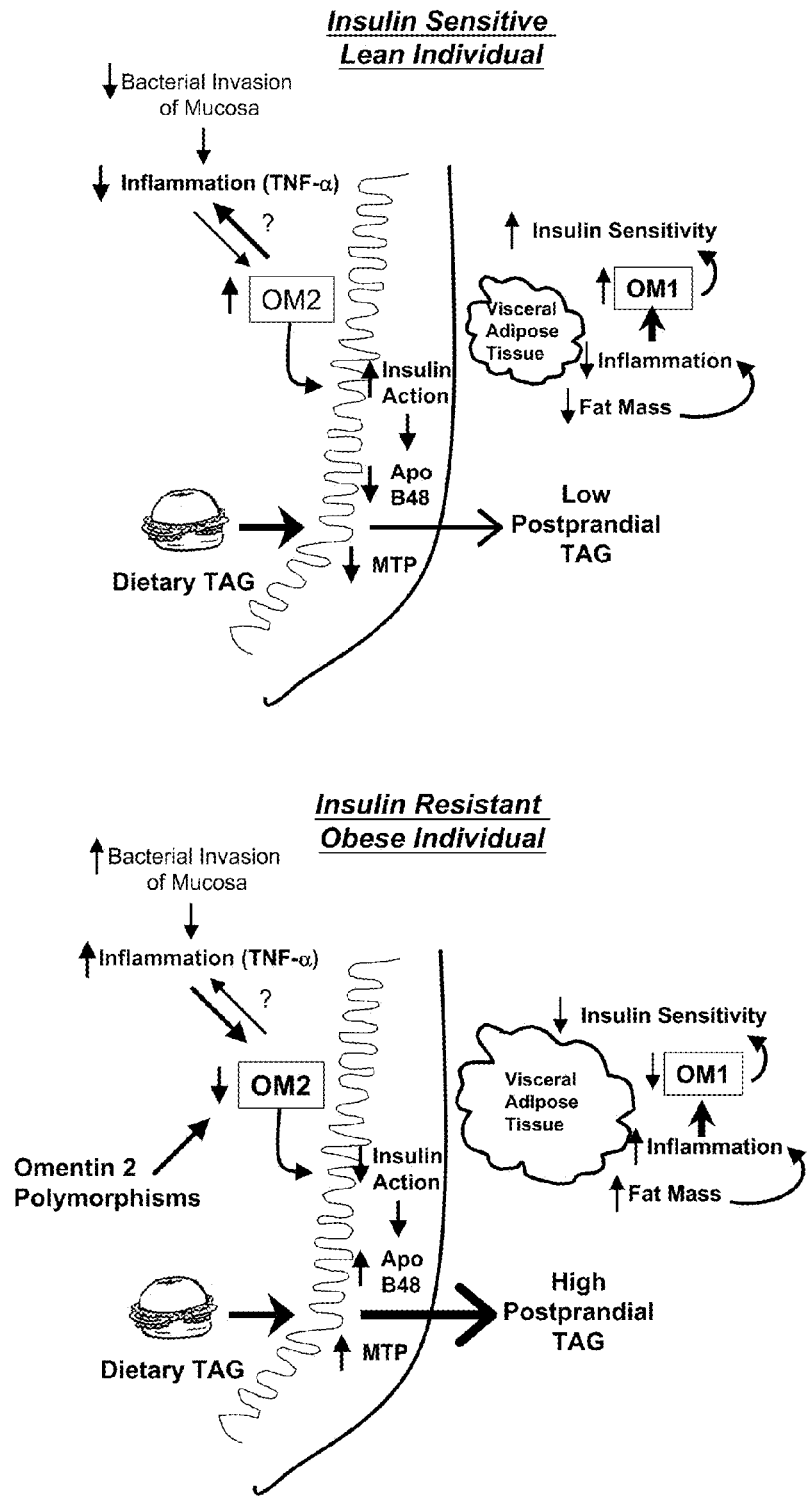
FIG. 1 is an illustration of the hypothesis that the insulin-mimetic effect of omentin 2 promotes decreased postprandial lipemia by lowering MTP (microsomal transfer protein) and production of apoB48 TG-rich lipoproteins released into the circulation.

The present invention is based on the novel findings that the polypeptides omentin 1 and omentin 2 play a role mammalian metabolism. As described in detail below and in the inventors' publication (87), the data presented herein suggests that omentin secretion from visceral fat may positively impact insulin sensitivity and glucose homeostasis. Plasma omentin 1 correlates negatively with BMI, leptin, waist circumference, fasting insulin and HOMA, and positively with adiponectin and HDL (87). Both omentin 1 and 2 gene expression are also decreased with obesity in visceral adipose tissue (87). The preliminary data also demonstrates that both omentin 1 and 2 are negatively regulated by proinflammatory cytokines in human adipose explant cultures, omental adipose stromal-vascular cell cultures and human endothelial cells. This data implies a functional role for decreased omentin levels in the inflammatory/insulin resistance actions of TNF-alpha. The preliminary data shows that omentin plasma levels are decreased in subjects with elevated subacute inflammatory status. These aspects of omentin regulation are strikingly similar to adiponectin and consistent with the positive effect on glucose metabolism.

Omentin 1 and 2 genes are next to each other on chromosome 1 in an area that has been identified to have strong genetic linkage to diabetes or impaired glucose tolerance by the Amish Family Diabetes Study (AFDS) (66). 48 single nucleotide polymorphisms (SNPs) were genotyped across the omentin 1 (OM1) and omentin 2 (OM2) genes. Three polymorphisms were identified that associated with impaired glucose tolerance, quantitative traits such as BMI, waist, leptin, cholesterol, blood pressure and high triglyceride excursions after a high fat challenge. This data strongly implicates omentin 2 as a susceptibility gene for metabolic syndrome and its composite traits.

The preliminary data further indicates that omentin 2 has insulin-mimetic activity on 3T3-L1 adipocyte glucose transport. The diagram shown in FIG. 1 illustrates the inventors' current hypothesis that the insulin-mimetic effect of omentin 2 promotes decreased postprandial lipemia by lowering MTP (microsomal transfer protein) and production of apoB48 TG-rich lipoproteins released into the circulation. If omentin 2 levels are decreased by genetic polymorphisms or by local inflammation (or bacterial invasion of the mucosa), TG flux through the intestine should increase resulting in elevated plasma lipids, increased fat deposition and obesity. Increased obesity will result in decreased visceral adipose secretion of omentin 1 and increased insulin resistance. This hypothesis is consistent with the genetic data indicating that omentin 2 polymorphisms are associated with insulin resistance, obesity and increased postprandial triglyceride excursions. Omentin 2 (like omentin 1) is a secreted protein with lectin activity similar to RegIII. Thus, omentin 2 may have a dual function and act as a bacteriocidal protein that is part of the innate immune system. The bacteriocidal function would act to decrease local inflammatory responses which would still promote decreased TG absorption and lower plasma TG.

Methods of Diagnosis and Predicting an Increased Risk of a Disease

Accordingly, the present invention is directed to methods of diagnosing disease based on the amounts omentin 1 protein, omentin 2 protein, or both, in a subject. In particular, the amount of omentin 1 protein, omentin 2 protein, or both, is determined in a sample obtained from a subject and compared to a corresponding subject-matched control value determined for a population of subjects without the disease. When the amount of omentin 1 protein, omentin 2 protein, or both proteins is less than the corresponding subject-matched control value, the subject from which the sample was obtained is diagnosed as having the disease.

In a related embodiment, the present invention is directed to methods of predicting an increased risk of a disease based on the amounts omentin 1 protein, omentin 2 protein, or both, in a subject. In particular, the amount of omentin 1 protein, omentin 2 protein, or both, is determined in a sample from a subject and compared to a corresponding subject-matched control value determined for a population of subjects without the disease. When the amount of omentin 1 protein, omentin 2 protein, or both proteins is less than the corresponding subject-matched control value, the subject is predicted to have an increased risk of the disease.

The skilled artisan will also understand that the levels of omentin 1 and omentin 2 gene expression can be used to diagnose disease in a subject. In particular, the level of omentin 1 gene expression, omentin 2 gene expression, or both, is determined in a sample obtained from a subject, and compared to a corresponding subject-matched control value determined for a population of subjects without the disease. When the level of omentin 1 gene expression, omentin 2 gene expression, or both, is less than the corresponding subject-matched control value, the subject is diagnosed as having the disease.

In a related embodiment, the present invention is directed to methods of predicting an increased risk of a disease based on the levels of omentin 1 gene expression, omentin 2 gene expression, or both, in a subject. In particular, the level of omentin 1 gene expression, omentin 2 gene expression, or both, is determined in a sample obtained from a subject, and compared to a corresponding subject-matched control value determined for a population of subjects without the disease. When the level of omentin 1 gene expression, omentin 2 gene expression, or both, is less than the corresponding subject-matched control value, the subject is predicted to have an increased risk of the disease.

The present invention also includes methods of diagnosing a disease in a subject based on the detection of a polymorphism in the omentin 1 gene or the omentin 2 gene. As used herein, a gene includes the entire polynucleotide corresponding to a particular coding region, including the coding region, upstream regulatory region, downstream regulatory region, introns, transcriptional start and stop sites, and other regions consider by those of skill in the art to be encompassed within a particular gene.

The polymorphism that may be detected include the single nucleotide polymorphisms (SNPs) shown in Table 3. As shown in Table 3, SNPs have been identified in various regions of both the omentin 1 gene and the omentin 2 gene. As further described herein, three of the omentin 2 SNPs set forth in Table 3 (Om-74938, Om-81237 and Om-81873) were found to associate with impaired glucose tolerance in AFDS subjects. One SNP in particular (Om-74938) was found to be associated with metabolic syndrome-related traits in AFDS subjects.

Thus, the present invention also includes methods of diagnosing a disease in a subject by detecting at least one omentin 1 gene polymorphism or at least one omentin 2 gene polymorphism in a subject. In a preferred embodiment, the polymorphism is a SNP. In a further preferred example, the polymorphism is 1, 2, 3, 4, 5, 6, 7, 8, 9, 10 or more of the SNPs set forth in Table 3.

In a specific embodiment, the present invention is directed to methods of diagnosing a disease in a subject comprising, detecting at least one omentin 2 gene polymorphism in a nucleic acid sample of a subject, wherein the at least one omentin 2 gene polymorphism is a SNP selected from the group consisting of Om-74938, Om-81237 and Om-81873, wherein upon detection of the at least one omentin 2 gene polymorphism, the subject is diagnosed as having the disease. In a variation on the method, two of the SNPs are detected or all three of the SNPs are detected.

In a related embodiment, the present invention includes methods of predicting an increased risk of a disease in a subject based on the detection of a polymorphism in the omentin 1 gene or the omentin 2 gene. In a preferred embodiment, the present invention is directed to methods of predicting an increased risk of a disease in a subject comprising, detecting at least one omentin 2 gene polymorphism in a nucleic acid sample of a subject, wherein the at least one omentin 2 gene polymorphism is a SNP selected from the group consisting of Om-74938, Om-81237 and Om-81873, wherein upon detection of the at least one omentin 2 gene polymorphism, the subject is predicted to have an increased risk of the disease. In a variation on the method, two of the SNPs are detected or all three of the SNPs are detected.

Methods of Treatment Using Polypeptides

The present invention is also directed to methods of treating a disease in a subject using the proteins of the present invention. In particular, the present invention is directed to methods of treating a subject having a disease by administering a therapeutically effective amount of omentin protein 1, omentin protein 2, or both, to a subject having a disease, thereby treating the disease in the subject.

In alternative embodiments, polypeptide homologs or biologically active fragments of omentin 1 or 2 can be used in these methods. For example, the present invention includes a method of treating a subject having a disease by administering a therapeutically effective amount of a polypeptide homolog of omentin 1 or omentin 2, or both, to a subject having a disease, thereby treating the disease in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of treating a subject having a disease by administering a therapeutically effective amount of a biologically active fragment of omentin 1 or omentin 2, or both, to a subject having a disease, thereby treating the disease in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

The present invention is also directed to methods of reducing body mass index (BMI) in a subject using the proteins of the present invention. In particular, the present invention is directed to methods of reducing body mass index (BMI) in a subject by administering a therapeutically effective amount of omentin protein 1, omentin protein 2, or both, to a subject, thereby the reducing body mass index (BMI) in the subject.

In alternative embodiments, polypeptide homologs or biologically active fragments of omentin 1 or 2 can be used in these methods. For example, the present invention includes a method of reducing body mass index (BMI) in a subject by administering a therapeutically effective amount of a polypeptide homolog of omentin 1 or omentin 2, or both, to a subject, thereby reducing body mass index (BMI) in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of reducing body mass index (BMI) in a subject by administering a therapeutically effective amount of a biologically active fragment of omentin 1 or omentin 2, or both, to a subject, thereby reducing body mass index (BMI) in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

The present invention is also directed to methods of reducing leptin in a subject using the proteins of the present invention. In particular, the present invention is directed to methods of reducing leptin in a subject by administering a therapeutically effective amount of omentin protein 1, omentin protein 2, or both, to a subject, thereby reducing leptin in the subject.

In alternative embodiments, polypeptide homologs or biologically active fragments of omentin 1 or 2 can be used in these methods. For example, the present invention includes a method of reducing leptin in a subject by administering a therapeutically effective amount of a polypeptide homolog of omentin 1 or omentin 2, or both, to a subject, thereby reducing leptin in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of reducing leptin in a subject by administering a therapeutically effective amount of a biologically active fragment of omentin 1 or omentin 2, or both, to a subject, thereby reducing leptin in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

The present invention is also directed to methods of treating insulin resistance in a subject having insulin resistance using the proteins of the present invention. In particular, the present invention is directed to methods of treating insulin resistance in a subject by administering a therapeutically effective amount of omentin protein 1, omentin protein 2, or both, to a subject having insulin resistance, thereby treating insulin resistance in the subject.

In alternative embodiments, polypeptide homologs or biologically active fragments of omentin 1 or 2 can be used in these methods. For example, the present invention includes a method of treating insulin resistance in a subject by administering a therapeutically effective amount of a polypeptide homolog of omentin 1 or omentin 2, or both, to a subject having insulin resistance, thereby treating insulin resistance in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of treating insulin resistance in a subject by administering a therapeutically effective amount of a biologically active fragment of omentin 1 or omentin 2, or both, to a subject having insulin resistance, thereby treating insulin resistance in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

The present invention is also directed to methods of reducing inflammation in a subject using the proteins of the present invention. In particular, the present invention is directed to methods of reducing inflammation in a subject by administering a therapeutically effective amount of omentin protein 1, omentin protein 2, or both, to a subject, thereby reducing inflammation in the subject.

In alternative embodiments, polypeptide homologs or biologically active fragments of omentin 1 or 2 can be used in these methods. For example, the present invention includes a method of reducing inflammation in a subject by administering a therapeutically effective amount of a polypeptide homolog of omentin 1 or omentin 2, or both, to a subject, thereby reducing inflammation in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of reducing inflammation in a subject by administering a therapeutically effective amount of a biologically active fragment of omentin 1 or omentin 2, or both, to a subject, thereby reducing inflammation in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

Methods of Treatment Using Vectors

The present invention is also directed to methods of treating a disease in a subject using vectors comprising a polynucleotide encoding the proteins of the present invention. In particular, the present invention is directed to methods of treating a subject having a disease by administering a therapeutically effective amount of a vector comprising a polynucleotide encoding omentin protein 1, omentin protein 2, or both, to a subject having a disease, thereby treating the disease in the subject.

In alternative embodiments, vectors comprising polynucleotides encoding polypeptide homologs or biologically active fragments of omentin 1 or 2 can be used in these methods. For example, the present invention includes a method of treating a subject having a disease by administering a therapeutically effective amount of vector comprising a polynucleotide encoding a polypeptide homolog of omentin 1 or omentin 2, or both, to a subject having a disease, thereby treating the disease in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of treating a subject having a disease by administering a therapeutically effective amount of vector comprising a polynucleotide encoding a biologically active fragment of omentin 1 or omentin 2, or both, to a subject having a disease, thereby treating the disease in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

The present invention is also directed to methods of reducing body mass index (BMI) in a subject using vectors comprising polynucleotides encoding the proteins of the present invention. In particular, the present invention is directed to methods of reducing body mass index (BMI) in a subject by administering a therapeutically effective amount of vector comprising a polynucleotide encoding omentin protein 1, omentin protein 2, or both, to a subject, thereby the reducing body mass index (BMI) in the subject.

In alternative embodiments, vectors comprising polynucleotides encoding polypeptide homologs or biologically active fragments of omentin 1 or 2 can be used in these methods. For example, the present invention includes a method of reducing body mass index (BMI) in a subject by administering a therapeutically effective amount of vector comprising a polynucleotide encoding a polypeptide homolog of omentin 1 or omentin 2, or both, to a subject, thereby reducing body mass index (BMI) in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of reducing body mass index (BMI) in a subject by administering a therapeutically effective amount of vector comprising a polynucleotide encoding a biologically active fragment of omentin 1 or omentin 2, or both, to a subject, thereby reducing body mass index (BMI) in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

The present invention is also directed to methods of reducing leptin in a subject using vectors comprising polynucleotides encoding the proteins of the present invention. In particular, the present invention is directed to methods of reducing leptin in a subject by administering a therapeutically effective amount of vector comprising a polynucleotide encoding omentin protein 1, omentin protein 2, or both, to a subject, thereby reducing leptin in the subject.

In alternative embodiments, vectors comprising polynucleotides encoding polypeptide homologs or biologically active fragments of omentin 1 or 2 can be used in these methods. For example, the present invention includes a method of reducing leptin in a subject by administering a therapeutically effective amount of vector comprising a polynucleotide encoding a polypeptide homolog of omentin 1 or omentin 2, or both, to a subject, thereby reducing leptin in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of reducing leptin in a subject by administering a therapeutically effective amount of vector comprising a polynucleotide encoding a biologically active fragment of omentin 1 or omentin 2, or both, to a subject, thereby reducing leptin in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

The present invention is also directed to methods of treating insulin resistance in a subject having insulin resistance using vectors comprising polynucleotides encoding the proteins of the present invention. In particular, the present invention is directed to methods of treating insulin resistance in a subject by administering a therapeutically effective amount of vector comprising a polynucleotide encoding omentin protein 1, omentin protein 2, or both, to a subject having insulin resistance, thereby treating insulin resistance in the subject.

In alternative embodiments, vectors comprising polynucleotides encoding polypeptide homologs or biologically active fragments of omentin 1 or 2 can be used in these methods. For example, the present invention includes a method of treating insulin resistance in a subject by administering a therapeutically effective amount of vector comprising a polynucleotide encoding a polypeptide homolog of omentin 1 or omentin 2, or both, to a subject having insulin resistance, thereby treating insulin resistance in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of treating insulin resistance in a subject by administering a therapeutically effective amount of vector comprising a polynucleotide encoding a biologically active fragment of omentin 1 or omentin 2, or both, to a subject having insulin resistance, thereby treating insulin resistance in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

The present invention is also directed to methods of reducing inflammation in a subject using vectors comprising polynucleotides encoding the proteins of the present invention. In particular, the present invention is directed to methods of reducing inflammation in a subject by administering a therapeutically effective amount of vector comprising a polynucleotide encoding omentin protein 1, omentin protein 2, or both, to a subject, thereby reducing inflammation in the subject.

In alternative embodiments, vectors comprising polynucleotides encoding polypeptide homologs or biologically active fragments of omentin 1 or 2 can be used in these methods. For example, the present invention includes a method of reducing inflammation in a subject by administering a therapeutically effective amount of vector comprising a polynucleotide encoding a polypeptide homolog of omentin 1 or omentin 2, or both, to a subject, thereby reducing inflammation in the subject. Preferably, the polypeptide homologs are homologs of omentin 1 or omentin 2 having at least 90%, 91%, 92%, 93%, 94%, 95%, 96%, 97%, 98% or 99% identity to the reference polypeptide.

In a further variation, the present invention includes a method of reducing inflammation in a subject by administering a therapeutically effective amount of vector comprising a polynucleotide encoding a biologically active fragment of omentin 1 or omentin 2, or both, to a subject, thereby reducing inflammation in the subject. Preferably, the biologically active fragment of omentin protein 1 is TTRGWSTDEANTYFC (SEQ ID NO:5), SQQGSKAVYPEGDGC (SEQ ID NO:6), GSAEAATSDDYKNPC (SEQ ID NO:7), or VPNKSPMQHWRNSSC (SEQ ID NO:8).

Methods of Inhibiting Omentin Gene Expression

The present invention also includes methods of inhibiting omentin 1 and 2 gene expression in a subject by administering a proinflammatory cytokine to a subject.

In a preferred embodiment, the present invention is directed to a method of inhibiting omentin 1 or 2 gene expression, or both, in a subject, comprising administering to a subject in which inhibition of omentin 1 or 2 gene expression, or both, is desired an effective amount of a proinflammatory cytokine, thereby inhibiting omentin 1 or 2 gene expression, or both, in the subject. In these embodiments, the proinflammatory cytokine is IL-6 or TNF-alpha.

Methods of Inhibiting Omentin Gene Expression

The present invention further includes methods of increasing omentin 1 or 2 gene expression in a subject by administering IL-13 to a subject.

In a preferred embodiment, the present invention is directed to a method of increasing omentin 1 or 2 gene expression, or both, in a subject, comprising administering to a subject in which an increase in omentin 1 or 2 gene expression, or both, is desired an effective amount of IL-13, thereby increasing omentin 1 or 2 gene expression, or both, in the subject.

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternative are mutually exclusive, although the disclosure supports a definition that refers to only alternatives and "and/or."

Omentin 1 of the present invention comprises the amino acid sequence set forth in SEQ ID NO:1 (313 amino acids), and is encoded by the nucleic acid sequence set forth in SEQ ID NO:2 (1284 nucleotides). Omentin 2 comprises the amino acid sequence set forth in SEQ ID NO:3 (325 amino acids), and is encoded by the nucleic acid sequence set forth in SEQ ID NO:4 (1150 nucleotides).

In each of the methods of the present invention, the disease that is diagnosed or treated, or the disease for which an increased risk is predicted, may be polycystic ovary disease, Crohn's disease, celiac disease, obesity, obesity-dependent subacute inflammation, atherosclerosis, a cardiovascular disease, inflammation, or a metabolic disease. Cardiovascular diseases include coronary heart disease, cerebral arterial disease, peripheral vascular disease and peripheral artery disease. Metabolic diseases include pre-diabetes, type 1 diabetes, type 2 diabetes, hyperglycemia, hyperlipidemia, dyslipidemia, and hypertension. Inflammation includes subacute inflammation.

In each of the methods of the present invention, the sample from which the amount of omentin protein is determined may be any biological fluid, tissue or material containing protein from the subject. Preferably, the sample is one or more of a whole blood sample, a serum sample, a plasma sample, a stool sample, a small intestine tissue sample, a visceral adipose tissue sample, a subcutaneous adipose tissue sample, or other bodily fluids that may reflect a specific disorder, such as urine, saliva, or cerebro-spinal fluid.

In each of the methods of the present invention, the nucleic acid sample from which polymorphisms may be detected may be DNA or RNA from any biological fluid, tissue or material from the subject that contains nucleic acids. Preferably, the nucleic acid sample from which polymorphisms may be detected is DNA or RNA isolated from a cell present in whole blood, serum, plasma, stool, small intestine tissue, visceral adipose tissue, subcutaneous adipose tissue, urine, saliva, or cerebro-spinal fluid.

As used herein, the "subject" refers to a mammal, such as a human, in need treatment for a disease as defined herein. In a preferred embodiment, the disease is obesity, obesity-dependent subacute inflammation, atherosclerosis, cardiovascular disease or a metabolic disease.

As used herein, the subject-matched control value is a value obtained from a population of subjects that does not have the particular disease for which the subject is being screened, but has at least one characteristic in common with the subject selected from age, sex, obesity status, diabetes status, cancer status and inflammation status. The population of subjects in the control group may comprise one subject or more than one subject, such as 10, 20, 30, 40, 50, 100, or more subjects. The obesity status of a subject is selected from: (a) lean (BMI<25 kg/m$^2$), (b) overweight (25 kg/m$^2$≦BMI<30 kg/m$^2$), and (c) obese (BMI≧30.0 kg/m$^2$). The inflammation status of a subject is selected from: (a) normal, and (b) a sub-acute inflammatory state.

In a preferred embodiment, the subject is matched to a subject-matched control value where there are two or more characteristics in common. For example, the amount of omentin protein (or level of omentin gene expression) in a sample from a subject who is being screened for a disease or the risk of developing a disease is compared to the amount of omentin protein (or level of omentin gene expression) determined from a sample from the same biological source from a population of subjects that does not have the disease, but that shares at least two of the following characteristics with the subject: age, sex, obesity status, diabetes status, cancer status and inflammation status.

When the amount of protein (or level of gene expression) in a sample from a subject is compared to the subject-matched control value, the amount of protein (or level of gene expression) in the sample from the subject is determined to be less than the subject-matched control value when there is a difference of at least 0.5%, 1%, 2%, 3%, 4%, 5%, 6%, 7%, 8%, 9%, 10%, or more. The amount of protein (or level of gene expression) in a sample from a subject is also determined to be less than the subject-matched control value when the difference between the two values is statistically significant as determined, for example, by the Mann-Whitney unpaired t test or a Spearman correlation.

As used herein, an increased risk of a disease means an increased risk versus the risk of developing the same disease among the population of people living in the same geographic area or country. In a particular embodiment, the increased risk of a disease means an increased risk versus the risk of developing the same disease among the population of people living in the same country, having the same gender, and being within five years in age of the subject. An increased risk may be an increase of 0.5%, 1%, 2%, 3%, 4%, 5%, 6%, 7%, 8%, 9%, 10%, 15%, 20%, or more, versus the risk of the populations described above.

The skilled artisan will understand that many different means can be used to quantify the amount of omentin protein in the methods of the present invention. Both methods that permit a determination of a particular amount (e.g., weight versus volume; weight versus weight) of omentin protein in a sample, and those that provide a non-quantitative comparison, may be used. Exemplary means include proteomics, chromatography, such as HPLC, mass spectroscopy, and an immune-based assays, such as western blot analysis, ELISA (enzyme-linked immunosorbant assay) and RIA (radioimmunoassay). In one embodiment, proteins in a sample may be separated by two-dimensional gel electrophoresis followed by western blot analysis to determine the amount of omentin protein in a sample using, for example, a monoclonal or polyclonal antibody that binds to omentin 1, omentin 2, or both. In preferred example, the antibody is a monoclonal antibody that specifically binds to omentin 1, omentin 2, or both. The 3G1B3 antibody described herein may be used. In another embodiment, the proteins in a sample may be separated by SDS-PAGE and visualized using a protein stain, such as Sypro Ruby fluorescent protein stain (Bio-Rad, Hercules, Calif.) as described herein. The amount of protein in the gel may be quantified using a chemiluminescent/fluorescent imager.

The skilled artisan will also understand that many different means may be used to determine the levels of gene expression in the methods of the present invention. For example, the amount of omentin 1 and omentin 2 mRNA may be determined by real time quantitative PCR (QRT-PCR) or real time non-quantitative PCR(RT-PCR) as described herein, as well as other gene expression analytical tools and array analyses, such as branched DNA analysis. In one embodiment, commercially available PCR primers (omentin 1—Hs00214137_m1; omentin 2—Hs00365614_m1; Applied Biosystems, Foster City, Calif.) may be used.

The skilled artisan will further understand that many different methods may be used in the detection of a single nucleotide polymorphism in a gene of the present invention. For example, the particular region in which the polymorphism is known to be present may be sequenced to determine if the polymorphism is present.

The present invention includes polypeptide homologs of omentin 1 and 2 for use in the methods of the present invention. The polypeptide homologs of the present invention have sufficient homology as compared to a reference polypeptide to permit the polypeptide homolog to perform the same basic function and have equivalent activity as the corresponding reference polypeptide.

The polypeptide homologs of the present invention include those having least about 80%, 85%, 90%, 91%, 92%, 93%, 94%, 95%, 96%, 97%, 98% or 99% sequence identity to a reference polypeptide sequence over its entire length. The polypeptide homologs of the present invention further include those having least about 80%, 85%, 90%, 91%, 92%, 93%, 94%, 95%, 96%, 97%, 98% or 99% sequence similarity to a reference polypeptide sequence over its entire length. "Sequence similarity" means an amino acid sequence which differs only by conservative amino acid substitutions, for example, substitution of one amino acid for another of the same class (e.g., hydrophobic, non-polar, etc.).

The present invention further includes polynucleotide homologs of the polynucleotides encoding omentin 1 (SEQ ID NO:2) and 2 (SEQ ID NO:4) for use in the methods of the present invention. The polynucleotides homologs encode proteins having sufficient homology as compared to a reference polypeptide to permit the encoded polypeptide to perform the same basic function and have equivalent activity as the corresponding reference polypeptide. The polynucleotides homologs of the present invention include those having least about 80%, 85%, 90%, 91%, 92%, 93%, 94%, 95%, 96%, 97%, 98% or 99% sequence identity to a reference polynucleotide sequence over its entire length.

Homology may be measured using sequence analysis software (e.g., Sequence Analysis Software Package of the Genetics Computer Group, University of Wisconsin Biotechnology Center, 1710 University Avenue, Madison, Wis. 53705, or the NCBI BLAST program). Such software matches similar sequences by assigning degrees of homology to various substitutions, deletions, substitutions, and other modifications.

The present invention includes biologically active fragments of omentin 1 and 2 for use in the methods of the present invention. The biologically active fragments perform the same basic function and have equivalent activity as the corresponding reference polypeptide. The biologically active fragments may comprise about 25, 50, 75, 100, 150, 200, 225, 250, 275, 300, 301, 302, 303, 304, 305, 306, 307, 308, 309, 310, 311 or 312 contiguous amino acids of omentin 1, or about 25, 50, 75, 100, 150, 200, 225, 250, 275, 300, 310, 311, 312, 313, 314, 315, 316, 317, 318, 319, 320, 321, 322, 323 or 324 contiguous amino acids of omentin 2.

The biologically active fragments of omentin 1 of the present invention include the following four peptide fragments, each of which contains a carboxy terminal cysteine residue in addition to the amino acids of omentin 1:

```
Residues 13-26:
TTRGWSTDEANTYFC        (SEQ ID NO: 5)

Residues 102-115:
SQQGSKAVYPEGDGC        (SEQ ID NO: 6)

Residues 124-137:
GSAEAATSDDYKNPC        (SEQ ID NO: 7)

Residues 152-165:
VPNKSPMQHWRNSSC        (SEQ ID NO: 8)
```

The present invention also includes fragments of the polynucleotides encoding omentin 1 and 2 for use in the methods of the present invention. These fragments encode biologically active peptides that perform the same basic function and have equivalent activity as the corresponding reference polypeptide. The fragments may comprise those of about 5, 10, 12, 14, 16, 18, 20, 22, 24, 26, 28, 30, 32, 34, 36, 38, 40, 42, 75, 150, 225, 300, 450, 600, 675, 750, 825, 900, 903, 906, 909, 912, 915, 918, 921, 924, 927, 930, 933, 934, 935 or 936 contiguous nucleotides of the polynucleotide encoding omentin 1 (SEQ ID NO:2), or those of about 5, 10, 12, 14, 16, 18, 20, 22, 24, 26, 28, 30, 32, 34, 36, 38, 40, 42, 75, 150, 225, 300, 450, 600, 675, 750, 825, 900, 9300, 933, 936, 939, 942, 945, 948, 951, 954, 957, 960, 963, 966, 969, 970, 971 or 972 contiguous nucleotides of the polynucleotide encoding omentin 2 (SEQ ID NO:4).

The present invention further includes polynucleotides, the complement of which binds to SEQ ID NO:2 (encoding omentin 1) or SEQ ID NO:4 (encoding omentin 2), as well as the polypeptide encoding by such hybridizing polynucleotides, for use in the methods of the present invention. Such hybridizing polynucleotides encode biologically active polypeptides that perform the same basic function and have equivalent activity as the polypeptide encoded by the omentin polynucleotide used in the screening process.

The hybridizing polynucleotides can be isolated using standard hybridization techniques with probes of at least about 7 nucleotides, more preferably 15 nucleotides, in length (but can be as much as the full coding sequence). Homologous polynucleotide sequences can be identified using degenerate oligonucleotides based on the sequences disclosed herein which are capable of hybridization at moderate or greater stringency. The term, "capable of hybridization" as used herein means that the subject nucleic acid molecules (whether DNA or RNA) anneal to an oligonucleotide of 15 or more contiguous nucleotides of one of the polynucleotide sequences disclosed herein.

The choice of hybridization conditions will be evident to one ordinarily skilled in the art and will generally be guided by the purpose of the hybridization, the type of hybridization (DNA-DNA or DNA-RNA), and the level of desired relatedness between the sequences. Methods for hybridization are well established in the literature. One of ordinary skill in the art realizes that the stability of nucleic acid duplexes decrease with an increased number and location of mismatched bases. As a result, the stringency of hybridization can be used to maximize or minimize the stability of such duplexes. Hybridization stringency can be altered, for example, by adjusting the temperature of hybridization, adjusting the percentage of helix-destabilizing agents (e.g., formamide) in the hybridization mix, and adjusting the temperature and salt concentration of the wash solutions. In general, the stringency of hybridization is adjusted during post-hybridization washes by varying the salt concentration and/or the temperature, which results in progressively higher stringency conditions.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. Optimal conditions will vary depending on the particular hybridization reaction involved, and can be determined empirically. Conditions of high stringency are preferably used for the hybridization of the probe of interest.

Vectors

The methods of the present invention include the use of recombinant vectors, both for the delivery of a polynucleotide, such as a polynucleotide encoding omentin 1 or 2, or a homolog or fragment thereof, as well as for the expression of omentin 1 or 2, or a homolog or fragment thereof.

The recombinant vectors of the present invention can be constructed in a variety of forms well-known in the art. Preferred recombinant vectors are recombinant expression vectors such as plasmids and cosmids. Expression vectors commonly include one or more fragments of a particular polynucleotide, or gene, and or the full length gene. Such an expression vector can be used to transfect or transform a cell to produce a protein of the present invention.

Preferably the recombinant expression vector includes both the protein coding region and one or more regulatory sequences required for expression of the polypeptide encoded by the protein coding region. Examples of such regulatory regions include promoter binding sites, enhancer elements, ribosome binding sites, and the like. Those of ordinary skill in the art will be able to select regulatory sequences and incorporate them into the recombinant expression vectors described herein without undue experimentation. For example, suitable regulatory sequences for use in various eukaryotic and prokaryotic systems are described in Ausubel, et al., *Short Protocols in Molecular Biology*, 3rd ed., John Wiley & Sons, Inc, New York, 1997, which is hereby incorporated by reference in its entirety.

In a preferred example, the recombinant expression vectors of the present invention may comprise the entire omentin 1 gene or the entire omentin 2 gene. As used herein, the entire gene is that sequence of DNA that includes both the protein coding region and all naturally occurring regulatory regions associated with the protein coding region. In an equally preferred embodiment, commercially available recombinant expression vectors may be used to obtain expression of omentin 1 or 2 inside of a cell, whether in vitro or in vivo. Such vectors commonly include a multiple cloning site into which a cDNA of interest may be inserted and all of the regulatory elements required for expression of the polypeptide encoded by the cDNA. Suitable expression vectors include pcDNA3 (Invitrogen, Carlsbad, Calif.).

A recombinant virus may also be used as an expression vector. Exemplary viruses include the adenoviruses, adeno-associated viruses, lentivirus, herpes viruses, vaccinia, CMV, BLUESCRIPT (Stratagene, San Diego, Calif.), baculovirus, or an RNA virus such as a retrovirus or an alphavirus. Preferably, the retroviral vector is a derivative of a murine or avian retrovirus. The alphavirus vector is preferably derived from Sindbis or Semliki Forest Virus.

The viral vector can be made target specific by inserting one or more sequences of interest into the viral vector, along with another gene which encodes the ligand for a receptor on a specific target cell. For example, retroviral vectors can be made target specific by inserting a polynucleotide encoding a sugar, a glycolipid, or a protein. Preferred targeting is accomplished by using an antibody to target the retroviral vector, such as to the vicinity of a mucosal inductor site, using a MALT-specific antibody. Those of skill in the art will know of, or can readily ascertain without undue experimentation, specific polynucleotide sequences which can be inserted into the retroviral genome to allow target specific delivery of the retroviral vector containing the polynucleotides of interest.

In some instances, it can be preferable to use a selectable marker to identify cells or organisms that contain the expression vector and the DNA of interest. Selectable markers are generally introduced into the cells or organisms along with the cloned DNA molecules and include genes that confer resistance to drugs such as ampicillin, neomycin, hygromycin, and methotrexate. Selectable markers can also complement auxotrophies in the host cell, or can provide for detectable signals, such as beta-galactosidase, green fluorescent protein, or yellow fluorescent protein, to identify cells or organisms containing the cloned DNA molecules.

Construction of suitable expression vectors containing desired coding, non-coding, and control sequences employ standard ligation techniques. Isolated plasmids or DNA fragments are cleaved, tailored, and re-ligated in the form desired to construct the required plasmids. To confirm correct sequences in the plasmids constructed, the ligation mixtures can be used, for example, to transform a host cell and successful transformants selected by antibiotic resistance where appropriate. Plasmids from the transformants are prepared, analyzed by restriction and/or sequenced by, for example, by the method disclosed in Messing, et al. (*Nucleic Acids Res.*, 9:309 (1981)), Maxam, et al. (*Methods in Enzymology* 65:499 (1980)), or other suitable methods which will be known to those skilled in the art. Size separation of cleaved fragments can be performed using conventional gel electrophoresis as described, for example, by Maniatis, et al. (Molecular Cloning, pp. 133-134 (1982)).

Host cells can be transformed with the expression vectors described herein and cultured in conventional nutrient media modified as is appropriate for inducing promoters, selecting transformants, or amplifying genes. The culture conditions, such as temperature, pH and the like, are those previously used with the host cell selected for expression, and will be apparent to the ordinarily skilled artisan.

Antisense

Antisense nucleotide sequences can be used to block expression of omentin 1 or 2. Suitable antisense oligonucleotides are at least 11 nucleotides in length and can include untranslated (upstream) and associated coding sequences. Complements of the fragments of SEQ ID NOs:2 and 4, as described herein, may be used as antisense oligonucleotides. As known by those of skill in the art, the optimal length of an antisense oligonucleotide depends on the strength of the interaction between the antisense oligonucleotide and the complementary mRNA, the temperature and ionic environment in which translation takes place, the base sequence of the antisense oligonucleotide, and the presence of secondary and tertiary structures in the mRNA and/or in the antisense oligonucleotide. Suitable target sequences for antisense oligonucleotides include promoter regions, ribosome binding sites, and sites that interfere with ribosome progression.

Antisense oligonucleotides can be prepared, for example, by inserting a DNA molecule containing the target DNA sequence into a suitable expression vector such that the DNA molecule is inserted downstream of a promoter in a reverse orientation as compared to a particular gene of this invention. The expression vector can then be transduced, transformed, or transfected into a cell (prokaryotic and/or eukaryotic) suitable for expressing the antisense oligonucleotides. Alternatively, antisense oligonucleotides can be synthesized using standard manual or automated synthesis techniques. These synthesized oligonucleotides are introduced into suitable cells by a variety of means including electroporation, calcium phosphate precipitation, and microinjection. The selection of a suitable antisense oligonucleotide administration method would be evident to one of ordinary skill in the art.

With respect to synthesized oligonucleotides, the stability of antisense oligonucleotide-mRNA hybrids is advantageously increased by the addition of stabilizing agents to the oligonucleotide. One example of a stabilizing agent includes intercalating agents that are covalently attached to either or both ends of the oligonucleotide. In preferred embodiments, the oligonucleotides are made resistant to nucleases by modifications to the phosphodiester backbone by the introduction of phosphotriesters, phosphonates, phosphorothioates, phosphoroselenoates, phosphoramidates, phosphorodithioates, or morpholino rings.

Purification

Various aspects of protein isolation and purification are discussed in detail in Cooper, T. G., "The Tools of Biochemistry," John Wiley & Sons, New York, 1977, which is hereby incorporated by reference in its entirety. As the techniques of protein isolation and purification are notoriously well known in the art, this disclosure will refrain from discussing them in detail. Nevertheless, elements of the cited reference are summarized and discussed below.

Solubilization is required of most proteins that are to be purified, as most isolation procedures commonly used operate in aqueous solutions. In some cases, solubilization can be achieved by merely lysing a host cell within which a desired protein has been expressed. In other situations, additional steps, such as extracting the desired protein from a subcellular organelle, may be required. Osmotic lysis, grinding, the use of blenders, ultrasonic waves, presses, and other well known techniques of protein solubilization can be used with the methods disclosed herein.

There are a variety of techniques available that are well known in the art for the isolation and concentration of the proteins of this invention. These techniques include, but are not limited to, (1) differential solubility, (2) ion exchange chromatography, (3) absorption chromatography, (4) molecular sieve techniques, (5) affinity chromatography, (6) electrophoresis, and (7) electrofocusing. Each of these techniques can also be useful in the purification of a protein of this invention.

Stabilizing and maintaining a purified protein product in a functional state may warrant attention to a number of different conditions such as (1) pH, (2) degree of oxidation, (3) heavy metal concentration, (4) medium polarity, (5) protease concentration, and (6) temperature. One of ordinary skill in the art would readily know which of the available techniques to use to maintain purified protein in an active form without undue experimentation.

Formulations

The polypeptides and vectors described herein can be formulated in a variety of useful formats for administration by a variety of routes. Concentrations of the polypeptides and vectors described will be such that an effective dose of the polypeptides and vectors is included in the formulation. Determination of such a concentration would be readily apparent to those of ordinary skill in the art.

In one embodiment, the polypeptides and vectors of the present invention may be formulated, for example, for oral, sublingual, intranasal, intraocular, rectal, transdermal, mucosal, topical or parenteral administration. Parenteral modes of administration include, without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

In another embodiment, administration of the polypeptides and vectors can be to mucosal tissues by nasal application, by inhalation, ophthalmically, orally, rectally, vaginally, or by any other mode that results in the polypeptides and vectors contacting mucosal tissues.

Formulations for parenteral administration can be in the form of aqueous or non-aqueous isotonic sterile injection solutions, suspensions or fat emulsions. The parenteral form used for injection must be fluid to the extent that easy syringability exists. These solutions or suspensions can be prepared from sterile concentrated liquids, powders or granules.

Excipients useful in parenteral preparations also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Injectable preparations include sterile aqueous solutions or dispersions and powders, which may be diluted or suspended in a sterile environment prior to use. Carriers such as solvents or dispersion media containing water, ethanol polyols, vegetable oils and the like may also be added to the compositions described herein. Coatings such as lecithins and surfactants may be used to maintain the proper fluidity of the composition. Isotonic agents such as sugars or sodium chloride may be added, as well as products intended to delay absorption of the active compounds, such as aluminum monostearate and gelatin. Sterile injectable solutions are prepared according to methods well known to those of skill in the art and can be filtered prior to storage and/or use. Sterile powders may be vacuum or freeze dried from a solution or suspension. Sustained-release preparations and formulations are also contemplated. Any material used in the compositions described herein should be pharmaceutically acceptable and substantially non-toxic in the amounts employed. Antimicrobial compounds may optionally be added to the preparations.

Parenteral formulations may also use hydrophobic carriers including, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

Alternatively, the unit dosage of the polypeptides and vectors of the present invention can be in a concentrated liquid, powder or granular form for ex tempore reconstitution in the appropriate pharmaceutically acceptable carrier at the time of delivery, and dilution where appropriate. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

In intravenous (IV) use, a sterile formulation of the polypeptides and vectors of the present invention and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose or Ringer's™ solution.

In intramuscular preparations, a sterile formulation of the polypeptides and vectors of the present invention can be prepared and administered in a pharmaceutical diluent such as Water-for-Injection (WFI), physiological saline or 5% dextrose.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, micro-crystalline cellulose, cornstarch, sodium starch glycolate, and alginic acid. Tablet binders that may be used include acacia, methylcellulose, sodium carboxymethylcellulose, polyvinylpyrrolidone, hydroxypropyl methylcellulose, sucrose, starch, and ethylcellulose. Lubricants that may be used include magnesium stearates, stearic acid, ailicone fluid, talc, waxes, oil, and colloidal silica.

In one embodiment of the present invention, the polypeptides and vectors exists as an atomized dispersion for delivery by inhalation. The atomized dispersion of the polypeptides and vectors typically contains carriers common for atomized or aerosolized dispersions, such as buffered saline and/or other compounds well known to those of skill in the art. The delivery of the polypeptides and vectors via inhalation has the effect of rapidly dispersing the polypeptides and vectors to a large area of mucosal tissues as well as quick absorption by the blood for circulation of the polypeptides and vectors. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

The polypeptides and vectors described herein can also be formulated in the form of a rectal or vaginal suppository. Typical carriers used in the formulation of the inactive portion of the suppository include polyethylene glycol, glycerine, cocoa butter, and/or other compounds well known to those of skill in the art. Although not wishing to be bound by theory, delivery of polypeptides and vectors via a suppository is hypothesized to have the effect of contacting a mucosal surface with the polypeptides and vectors for release to proximal mucosal tissues. Distal mucosal tissues also receive the polypeptides and vectors by diffusion. Other suppository formulations suitable for delivery of the polypeptides and vectors encompassed by the present invention are also contemplated.

Additionally, the polypeptides and vectors of the present invention may also be formulated in a liquid form. The liquid can be for oral dosage, for ophthalmic or nasal dosage as drops, or for use as an enema or douche. When the polypeptides and vectors are formulated as a liquid, the liquid can be either a solution or a suspension of the polypeptides and vectors. There is a variety of suitable formulations for the solution or suspension of the polypeptides and vectors that are well know to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Delivery of the described polypeptides and vectors in liquid form via oral dosage exposes the mucosa of the gastrointestinal and urogenital tracts to the polypeptides and vectors. A suitable dose, stabilized to resist the pH extremes of the stomach, delivers the polypeptides and vectors to all parts of the gastrointestinal tract, especially the intestines. Any method of stabilizing the polypeptides and vectors in a liquid oral dosage such that the effective delivery of the composition is distributed along the gastrointestinal tract are contemplated for use with the polypeptides and vectors described herein.

Delivery of the described polypeptides and vectors in liquid form via ophthalmic drops exposes the mucosa of the eyes and associated tissues to the polypeptides and vectors. A typical liquid carrier for eye drops is buffered and contains other compounds well known and easily identifiable to those of skill in the art.

Delivery of the described polypeptides and vectors in liquid form via nasal drops exposes the mucosa of the nose and sinuses and associated tissues to the polypeptides and vectors. Liquid carriers for nasal drops are typically various forms of buffered saline.

Injectable formulations of the polypeptides and vector compositions may contain various carriers such as vegetable oils, dimethylacetamide, dimethylformaamide, ethyl lactate, ethyl carbonate, isopropyl myristate, ethanol, polyols (glycerol, propylene glycol, and liquid polyethylene glycol) and the like. For intravenous injections, water soluble versions of the polypeptides and vector compositions may be administered by the drip method, whereby a pharmaceutical formulation containing an antifungal agent and/or a physiologically acceptable excipient is infused. Physiologically acceptable excipients may include, for example, 5% dextrose, 0.9% saline, Ringer's solution or other suitable excipients. Intramuscular preparations of the polypeptides and vector (e.g., a sterile formulation of a suitable soluble salt form of the composition) can be administered in a pharmaceutical excipient such as Water-for-Injection, 0.9% saline, or 5% glucose solution. A suitable insoluble form of the composition may be prepared and administered as a suspension in an aqueous base or a pharmaceutically acceptable oil base, such as an ester of a long chain fatty acid (e.g., ethyl oleate).

In addition to naked DNA in the case of the vectors and unassociated protein in the case of the polypeptides of the present invention, a colloidal dispersion system may be used for targeted delivery of the polypeptides and vectors of the present invention. Colloidal dispersion systems include macromolecule complexes, nanocapsules, microspheres, beads, and lipid-based systems including oil-in-water emulsions, micelles, mixed micelles, and liposomes. A preferred colloidal system is a lipid preparation including unilamaller and multilamellar liposomes.

Liposomes are artificial membrane vesicles that are useful as delivery vehicles in vitro and in vivo. It has been shown that large unilamellar vesicles (LUV), which range in size from 0.2-4.0 μm, can encapsulate a substantial percentage of an aqueous buffer containing large macromolecules. RNA, DNA, and intact virions can be encapsulated within the aqueous interior and can be delivered to cells in a biologically active form (Fraley, et al., *Trends Biochem. Sci.* 6:77 (1981)). In order for a liposome to be an efficient expression vector transfer vehicle, the following characteristics should be present: (1) encapsulation of the expression vector encoding the polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:682 (1988)). In addition to such LUV structures, multilamellar and small unilamellar lipid preparations that incorporate various cationic lipid amphiphiles can also be mixed with anionic polynucleotides to form nucleolipidic particles which are often also referred to as liposomes. (Felgner, et al., *Proc Natl. Acad. Sci. U.S.A.* 84 (21): 7413 (1987)). These nucleophilic particles can be used to deliver the nucleic acids into cells.

The composition of the liposome is usually a combination of phospholipids, preferably high-phase-transition-temperature phospholipids, usually in combination with steroids, preferably cholesterol. However, other phospholipids or other lipids may also be used. The physical characteristics of the liposomes depend on pH, ionic strength, and the presence of divalent cations. The appropriate composition and preparation of cationic lipid amphiphile:polynucleotide formulations are known to those skilled in the art, and a number of references which provide this information are available (e.g., Bennett, et al, *J. Liposome Res.* 6(3):545).

Examples of lipids useful in liposome production include, but are not limited to phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, preferably from 16-18 carbon atoms, and is saturated. Illustrative phospholipids include egg phosphatidylcholine, dipalmitoylphosphatidylcholine, and distearoylphosphatidylcholine. Examples of cationic amphiphilic lipids useful in formulation of nucleolipid particles for polynucleotide delivery include the monovalent lipids DOTAP, DOTMA, and DC-Chol, the polyvalent lipids LipofectAMINE, DOGS, Transfectam, and other amphiphilic polyamines. These agents may be prepared with helper lipids (such as Dioleoyl Phosphatidyl Ethanolamine) or with various carrier compositions, including various adjuvants such as cholera-derived molecules including cholera toxin.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs that contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used to join the lipid chains to the targeting ligand.

Administration

Administration of the formulations discussed above can be practiced in vitro or in vivo. When practiced in vitro, any sterile, non-toxic route of administration may be used. When practiced in vivo, systemic administration of the formulations discussed above may be achieved advantageously by subcutaneous, intravenous, intramuscular, intraocular, oral, transmucosal, or transdermal routes, such as, for example, by injection or by means of a controlled release mechanism. Examples of controlled release mechanisms include polymers, gels, microspheres, liposomes, tablets, capsules, suppositories, pumps, syringes, ocular inserts, transdermal formulations, lotions, creams, transnasal sprays, hydrophilic gums, microcapsules, inhalants, and colloidal drug delivery systems.

While the polypeptides and vectors of the present invention may be administered systemically in the manners discussed above, in equally preferred embodiments of each of the methods set forth herein the polypeptides and vectors may be administered in a targeted fashion to a particular location in the subject, such as directly to the interior of the intestine or to the tissues of the intestine, to visceral adipose tissue or to subcutaneous adipose tissue.

As used herein, the terms "effective amount" or "therapeutically effective amount" are interchangeable and refer to an amount that results in an improvement or remediation of the symptoms of the disease or condition. Those of skill in the art understand that the effective amount may improve the patient's or subject's condition, but may not be a complete cure of the disease and/or condition.

The polypeptides and recombinant vectors are administered in pharmaceutically acceptable formulations and in substantially non-toxic quantities. Thus, the present invention also includes pharmaceutical compositions comprising a polypeptide or vector of the present invention, including the polypeptide homologs and biologically active fragments, and a pharmaceutically acceptable carrier or diluent.

The therapeutically effective amount of the polypeptides of the present invention varies depending upon the physical characteristics of the patient, the severity of the patient's symptoms, the disease or condition to be treated or inhibited, and the formulation and the means used to administer the polypeptides. The specific dose for a given subject is usually set by the judgment of the attending physician. However, a therapeutically effective amount of the polypeptides of the present invention is typically between about 0.5 mg/kg body weight to 500 mg/kg body weight, preferably from 1 to 100 mg/kg, more preferably from 3 to 50 mg/kg, 3 to 30 mg/kg or 3 to 15 mg/kg, regardless of the formulation. In equally preferred embodiments, a therapeutically effective amount is about 0.5, 1, 3, 5, 10, 15, 20, 25, 30, 35, 40, 45 or 50 mg/kg body weight, regardless of the formulation. In some situations, a dose less than 0.5 mg/kg body weight may be effective.

The therapeutically effective amount of the vectors of the present invention also varies depending upon the physical characteristics of the patient, the disease or condition to be treated or inhibited, the severity of the patient's symptoms, and the formulation and the means used to administer the vectors. The specific dose for a given subject is usually set by the judgment of the attending physician. However, a therapeutically effective amount of the vectors of the present invention is typically between about 0.5 mg/kg body weight to 500 mg/kg body weight, preferably from 1 to 100 mg/kg, more preferably from 3 to 50 mg/kg, 3 to 30 mg/kg or 3 to 15 mg/kg, regardless of the formulation. In equally preferred embodiments, a therapeutically effective amount is about 0.5, 1, 3, 5, 10, 15, 20, 25, 30, 35, 40, 45 or 50 mg/kg body weight, regardless of the formulation. In some situations, a dose less than 0.5 mg/kg body weight may be effective.

When the vector is a viral vector, the therapeutically effective amount of the viral vector will also vary depending upon the physical characteristics of the patient, the disease or condition to be treated or inhibited, the severity of the patient's symptoms, and the formulation and the means used to administer the vectors. The specific dose for a given subject is usually set by the judgment of the attending physician. However, a therapeutically effective amount of a viral vector of the present invention is typically between about $10^5$ to $10^{20}$ viral particles, preferably $10^8$ to $10^{18}$ viral particles, more preferably from $10^{10}$ to $10^{15}$ viral particles, regardless of the formulation.

Suitable frequencies for administering a polypeptide or vector of the invention to a subject may also vary based on the severity of the patient's symptoms, the disease or condition to be treated or inhibited, and the formulation and the means used to administer the polypeptide or vector. However, administration frequencies include 4, 3, 2 or once daily, every other day, every third day, every fourth day, every fifth day, every sixth day, once weekly, every eight days, every nine days, every ten days, bi-weekly, monthly and bi-monthly, yearly, and less frequent doses including a single dose.

The doses may be administered at the normal rate selected for a particular means of administration, or the doses may be administered at a slower rate, such as over a period of minutes, hours or days. Particular periods of administration include, 5, 10, 15, 20, 25, 50, 40, 50 or 60 minutes, and 1, 2, 3, 4, 5, 6, 7, 8, 9, 10 or more hours.

As used herein, the term "metabolic disease" is used interchangeably with "metabolic syndrome" and refers to a disease or condition resulting from obesity and/or insulin resistance, such as pre-diabetes, type 1 diabetes, type 2 diabetes, hyperglycemia, hyperlipidemia, dyslipidemia or hypertension.

The term "morbidity" as used herein is the state of being diseased. Yet further, morbidity can also refer to the disease rate or the ratio of sick subjects or cases of disease in to a given population.

The terms "preventing" and "prevention" as used herein refers to minimizing, reducing or suppressing: (i) the risk of developing a disease state or condition, (ii) parameters relating to a disease state or condition, and (iii) progression of a disease state or condition. As used herein, the prevention lasts at least one week, two weeks, three weeks, one month, two months, three, months, four months, five months, six months, seven months, eight months, nine months, ten months, eleven months, one year, two years, three years, four years, five years, six years, seven years or more, or indefinitely.

The terms "treating" and "treatment" as used herein refer to administering to a subject a therapeutically effective amount of a composition so that the subject has an improvement in the disease or condition. The improvement is any observable or measurable improvement, in the symptoms of the disease or condition and/or in the underlying physical basis of the disease or condition. One of skill in the art will understand that a treatment may improve the subject's condition, but may not be a complete cure of the disease. Each of the methods of treatment of the present invention can be practiced in a subject that does not yet have a particular disease or condition as a means for inhibiting the development of the particular disease or condition in the subject.

Preferably, treatment results in a measurable improvement where the improvement is a decrease of about 100%, 99%, 98%, 97%, 96%, 95%, 90%, 80%, 70%, 60%, 50%, 40%, 30%, 20%, 10%, 5% or 1% in the symptoms of the disease or condition and/or in the underlying physical basis of the disease or condition. The treatment may begin prior to, concurrent with, or after the onset of clinical symptoms of the disease or condition. Treatment may also comprise treating subjects at risk of developing a disease and/or condition.

As used herein, the term "bi-weekly" refers to a frequency of every 13-15 days, the term "monthly" refers a frequency of every 28-31 days and "bi-monthly" refers a frequency of every 58-62 days.

While the foregoing specification teaches the principles of the present invention, with examples provided for the purpose of illustration, it will be appreciated by one skilled in the art from reading this disclosure that various changes in form and detail can be made without departing from the true scope of the invention.

EXAMPLE I

Several studies have shown that visceral obesity is highly associated with risks for type 2 diabetes, cardiovascular disease, hypertension, and hyperlipidemia (1-4). Expression of adipose-derived factors such as leptin (27), PAI-1 (28) and adiponectin (29, 30) are modulated by obesity. Therefore, the following studies of circulating omentin levels in an obese insulin-resistant Old Order Amish population were undertaken to delineate the regulation of omentin in this pathophysiological state.

1. Subjects.

All studies involved healthy volunteers. Subjects that had malignant disease, diabetes, major renal, hepatic and/or thyroid dysfunction or were on hormonal replacement therapy were excluded. The study protocols were approved by the Institutional Review Boards for Human Subjects Research at all involved institutions. Written informed consent was obtained from all subjects.

Effect of Obesity on Omentin Gene Expression.

Human visceral (omental) adipose tissues were obtained from 21 subjects (M/F=3/18) over a range of age (24-73 years old) and BMI (21.5-66.6 kg/m²) undergoing intra-abdominal surgery at the University of Maryland Medical Center or The Johns Hopkins Bayview Medical Center. Tissue was immediately frozen in liquid nitrogen after excision and stored at −80° C. for subsequent RNA extraction and quantitative RT-PCR analysis. In a subgroup of these subjects (n=15, M/F=3/12) over a range of age (24-50 years old) and BMI (38.1-66.6 kg/m2), blood samples were collected after overnight fasting on visit prior to the day of the surgery. Plasma was separated and stored at −80° C. for subsequent quantification of omentin levels.

Effect of Obesity on Human Plasma Omentin Levels.

Subjects included 100 healthy volunteers (54 women and 46 men) comprising 50 age- (within 5 years) and sex-matched BMI discordant (>3.0 kg/m2 difference) sib pairs selected among those that participated in the previously described Amish Family Diabetes Study (AFDS) (24). The BMI-discordant sib pair design was chosen to maximize the power to detect association with BMI. Seven individuals did not fall within the detection limits of the assay and were excluded, for a final total of 93 participants (54 women and 39 men), including 46 sib pairs. For additional analyses, the participants were divided in three groups: (a) lean (n=41; BMI<25 kg/m2), (b) overweight (n=30; 25 kg/m≦BMI<30 kg/m$^2$), and (c) obese (n=22; BMI≧30.0 kg/m$^2$).

2. Identification of Omentin 1 and Omentin 2 in Human Plasma by Two-Dimensional Gel Electrophoresis.

Since two highly homologous isoforms of omentin/intelectin exist (16, 18) and may contribute to total circulating immunologically detectable omentin levels, human plasma samples, purified omentin 1 (11) and omentin 2 were separated by two-dimensional gel electrophoresis, followed by western blotting with anti-omentin monoclonal antibodies, to determine specificity of the 3G1B3 monoclonal antibody (11) as well as the relative abundance of omentin1/2 in plasma.

Omentin 2 cDNA was first subcloned into pcDNA3 (Invitrogen, Carlsbad, Calif.) and transfected into HEK-293A cells using Lipofectamine Plus (Invitrogen, Carlsbad, Calif.). Stably transfected cells were selected with 300 µg/mL G418. Omentin 2-expressing cells were cultured in 10% FBS/DMEM until 80% confluent and then switched to serum-free for 5 days. Conditioned media containing omentin 2 was then harvested and concentrated using Centricon centrifugal concentrators (Millipore, Billerica, Mass.).

Plasma samples, omentin 1 purified from conditioned media (11) and/or omentin 2 were diluted in rehydration buffer (Bio-Rad, Hercules, Calif.). First-dimensional isoelectric focusing was conducted using immobilized pH gradient strips (pH 3-10, 11 cm, Bio-Rad, Hercules, Calif.) in a Bio-Rad IEF Cell at 8000V for 20000 Voltage-hours. After focusing, strips were equilibrated using standard buffers (Bio-Rad, Hercules, Calif.) and were run on 10% SDS-PAGE in a Criterion apparatus for the second dimension (Bio-Rad, Hercules, Calif.). After that, proteins were transferred to Immobilon-PVDF membrane (Millipore, Billerica, Mass.), blocked with Starting Block Solution (Pierce, Rockford, Ill.) plus 0.1% Tween 20 (Pierce, Rockford, Ill.) and incubated with 3G1B3, a human omentin-specific monoclonal primary antibody (11), followed by horseradish peroxidase-conjugated anti-mouse secondary antibody (KPL, Gaithersburg, Md.). Immunoreactive spots were visualized by chemiluminescent detection with the Femto-West kit (Pierce, Rockford, Ill.) on a Fluorchem 8000 chemilumenescent/fluorescent imager (Alpha Innotech, San Leandro, Calif.).

Figure 2:
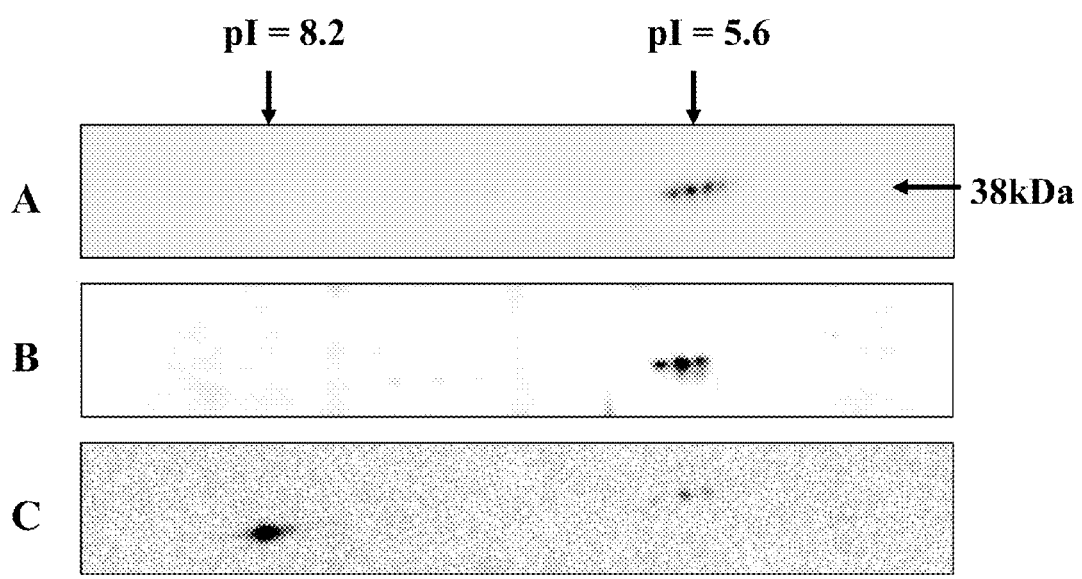
FIG. 2 depicts the identification of omentin 1 as the major omentin isoform in human plasma. Purified omentin 1 (A), human plasma (B) and human plasma plus exogenous omentin 2 (C) were subjected to two-dimensional gel electrophoresis and western blotting with anti-human omentin monoclonal antibody. Spots indicate immunoreactive omentin 1 and 2 with pIs of approximately 5.6 and 8.2, respectively. These data help validate the identity of omentin 1 as the major immunoreactive species quantitated on one-dimensional gel western blots.

Omentin 1 resolved three spots with pI≅5.6 and an apparent molecular weight of 38 kDa (FIG. 2A). All immunoreactive species, most likely resulting from post-translational modification, were confirmed to be omentin 1 by MALDI-TOF mass spectrometry analysis. A similar pattern was observed when human plasma samples were loaded (FIG. 2B). However, when omentin 2 conditioned media was analyzed, only one spot with a slightly lower molecular weight and a pI of 8.2 was observed. When omentin 2 was added to human plasma, three spots with pI≅5.6 plus one spot with pI≅8.2 were observed in a similar molecular weight range (FIG. 2C). The experimentally determined pIs were identical to the predicted pI values for omentin 1 and 2 based on amino acid sequence (26).

These data suggest that omentin 2 levels in human plasma were either below the limit of detection of the quantitative western blotting assay or absent in plasma. Additionally, the dual specificity of the 3G1B3 antibody for omentin 1 and 2 was confirmed based on these observations. Based on the crossreactivity of the 3G1B3 antibody and the differing pIs between omentin 1 and 2, omentin 1 was shown to be the major circulating form in plasma. Other apparent cross reactive species were not observed in the same molecular weight range of the omentins, thus validating the specificity of the monoclonal antibody 3G1B3 for omentin in human plasma by two-dimensional gel electrophoresis and its utility in the quantitative western blotting assay.

3. Quantification of Human Plasma Omentin Levels.

Quantification of Purified Omentin 1 Levels.

Purified omentin 1 (11) was used as a standard for the quantification of plasma omentin levels in the samples. Purified omentin 1 and standard purified bovine serum albumin (BSA, Pierce, Rockford, Ill.) were electrophoresed in duplicate on 10% SDS-PAGE gels (Criterion Pre-Cast, Bio-Rad, Hercules, Calif.). After electrophoresis, gels were stained with Sypro Ruby fluorescent protein stain (Bio-Rad, Hercules, Calif.). Fluorescent band intensities were visualized by 305 nm UV light and quantified on a Fluorchem 8000 chemilumenescent/fluorescent imager (Alpha Innotech, San Leandro, Calif.). A standard curve was constructed using the log transformed BSA concentrations versus the band intensities.

Quantification of Omentin 1 Levels in the "Standard Plasma" Samples.

Figure 3:
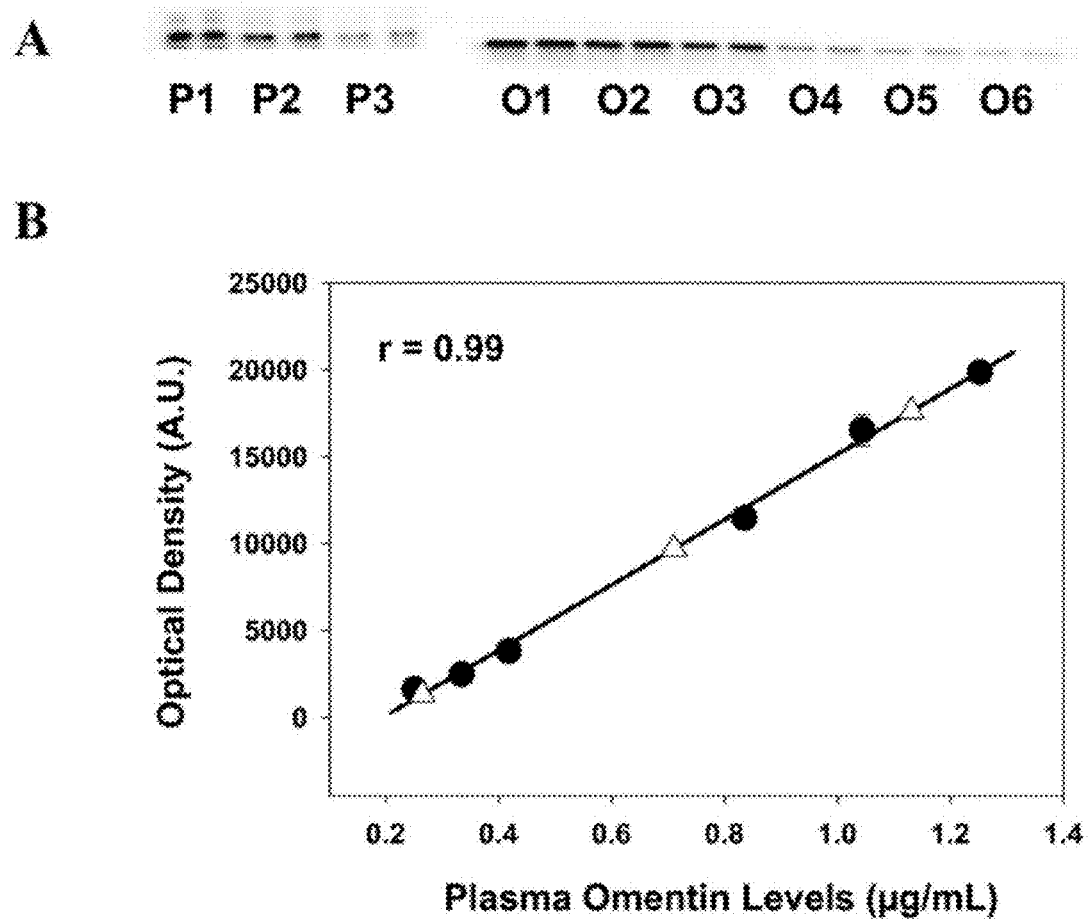
FIG. 3 depicts the quantification of omentin 1 levels in human plasma samples. (A) Plasma samples ("standard plasmas") from human subjects (marked P1, P2 and P3) and purified omentin at six different concentrations (marked O1 through O6) were electrophoresed in duplicate on 10% SDS-PAGE gel followed by western blotting with anti-omentin antibodies. (B) The standard curve was constructed by plotting known omentin concentrations (●) versus their optical densities in arbitrary units. Omentin concentrations in plasma (Δ) were extrapolated from this standard curve.

Due to the limited quantity of purified omentin, a subset of plasma samples were analyzed by quantitative western blotting using purified omentin 1 as a standard. These quantified plasma samples exhibiting a wide range of omentin content were used as "standard plasma" to quantify additional plasma samples. The "standard plasma" samples and purified omentin 1 were electrophoresed in duplicate on 10% SDS-PAGE gels (Criterion Pre-Cast, Bio-Rad, Hercules, Calif.). After electrophoresis, proteins were transferred to Immobilon-PVDF membrane (Millipore, Billerica, Mass.), and the same procedure for western blotting described above was followed. Immunoreactive bands were visualized and quantified by chemiluminescent detection with the Femto-West kit (Pierce, Rockford, Ill.) on a Fluorchem 8000 chemilumenescent/fluorescent imager (Alpha Innotech, San Leandro, Calif.). A standard curve was constructed using the purified omentin concentrations versus the optical densities (FIG. 3).

Quantification of Omentin 1 Levels in the Plasma Samples.

Human plasma omentin 1 levels were measured by quantitative western blotting using "standard plasma" samples to generate standard curves. Plasma samples from the subjects and previously quantified "standard plasmas" were electrophoresed in duplicate on 10% SDS-PAGE gels (Criterion Pre-Cast, Bio-Rad, Hercules, Calif.). After that, the same procedure used for the quantification of the "standard plasma" samples was followed for the subjects' samples. A standard curve was constructed using the "standard plasma" concentrations versus the optical densities.

Human Plasma Omentin 1 Levels Decrease with Obesity.

Metabolic and demographic characteristics of the AFDS subjects are presented in Table 1. Subjects were divided into lean (BMI<25 kg/m$^2$), overweight (25 kg/m2≦BMI<30 kg/m$^2$), and obese groups (BMI≧30.0 kg/m$^2$). Data are means±SE. P values are for the differences between the three groups by one-way ANOVA and post hoc comparisons. *P<0.05 vs. lean group. Four outliers were observed and consequently removed from the analyses. Plasma omentin 1 levels, determined by quantitative western blotting, were significantly higher in the leaner members of the BMI-discordant sib pairs than in their heavier siblings (paired t-test, n=44 sib pairs, P=0.002).

TABLE 1

| Variable | Lean | Overweight | Obese |
|---|---|---|---|
| n | 41 | 30 | 22 |
| Gender (M/F) | 18/23 | 13/17 | 8/14 |
| Age (years) | 43 ± 2 | 43 ± 2 | 46 ± 2 |
| BMI (kg/m2) | 21.9 ± 0.3 | 27.1 ± 0.3* | 32.6 ± 0.5* |
| Waist Circumference (cm) | 82.4 ± 1.3 | 91.5 ± 1.5* | 100.2 ± 1.4* |
| Insulin (μU/mL) | 9.0 ± 0.4 | 10.4 ± 0.9 | 12.4 ± 1.2* |
| Glucose (mg/dL) | 88.2 ± 1.3 | 90.8 ± 1.7 | 91.5 ± 1.5 |
| HOMA index | 1.9 ± 0.1 | 2.5 ± 0.2* | 2.8 ± 0.3* |
| Triglycerides (mmol/L) | 60.1 ± 4.6 | 77.5 ± 6.1 | 89.8 ± 7.0* |
| Total cholesterol (mmol/L) | 207.7 ± 6.9 | 206.0 ± 6.8 | 210.3 ± 9.1 |
| HDL cholesterol (mmol/L) | 59.0 ± 2.2 | 49.0 ± 2.4* | 46.7 ± 2.5* |
| LDL cholesterol (mmol/L) | 136.8 ± 6.5 | 141.3 ± 6.0 | 145.6 ± 8.5 |
| SBP (mmHg) | 113.9 ± 2.4 | 121.8 ± 2.4 | 122.9 ± 2.9 |
| DBP (mmHg) | 74.8 ± 1.2 | 78.7 ± 1.8 | 79.0 ± 1.6 |
| Adiponectin (μg/mL) | 19.0 ± 1.2 | 12.2 ± 0.9* | 12.4 ± 1.2* |
| Leptin (ng/mL) | 4.5 ± 0.5 | 9.1 ± 1.1* | 18.0 ± 2.4* |

Figure 4:
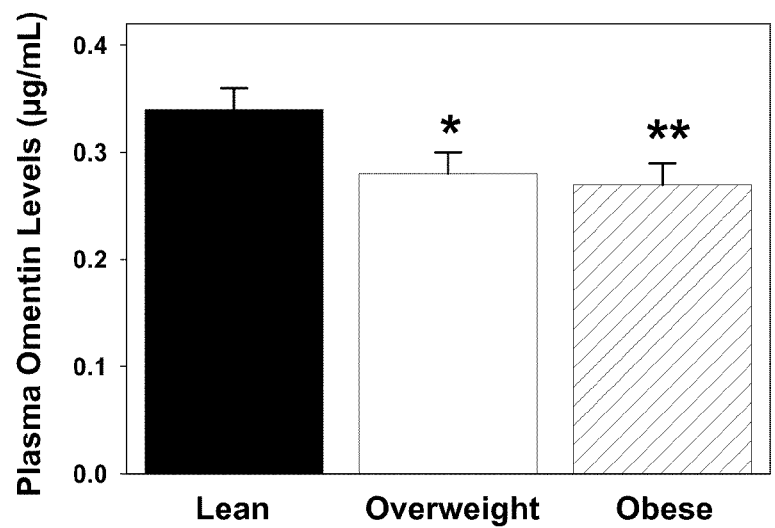
FIG. 4 shows circulating omentin 1 levels are decreased with obesity. Data are means±SE. P values are for the differences between the three groups by variance components analysis adjusted for age, sex and family structure. (A) Plasma omentin 1 levels were significantly higher in lean (black) than in overweight (white; *P=0.002) and obese subjects (striped; **P=0.002). (B) Plasma omentin 1 levels were higher in the female lean group compared with the overweight (ovw; *P=0.004) and obese groups (P=0.006). Plasma omentin 1 concentrations were significantly different between lean and obese males (*P=0.01), but not between lean and overweight males. Plasma omentin 1 levels were higher in lean females than in lean males (†P=0.04).
Figure 4:
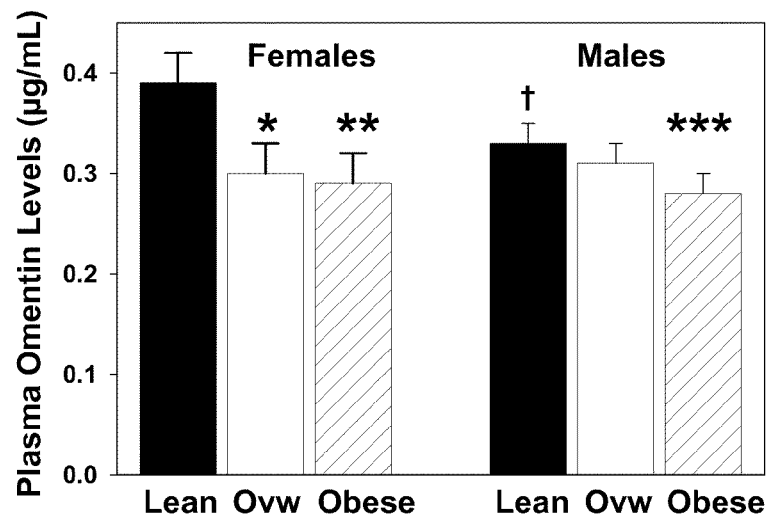

After regrouping subjects into established BMI categories, a variance component analysis, adjusted for age, sex and family structure, was performed to study the differences between lean and overweight, and lean and obese subjects. Plasma omentin 1 levels were shown to be significantly higher in lean (0.34±0.02 μg/mL, n=41) than in overweight (0.28±0.02 μg/mL, n=30, P=0.002) and obese groups (0.27±0.02 μg/mL, n=22, P=0.002) (FIG. 4A). Interestingly, females alone exhibited the same pattern. In females, plasma omentin 1 levels were higher in the lean group (0.39±0.03 μg/mL, n=23) than in the overweight (0.30±0.03 μg/mL, n=17, P=0.004) and obese groups (0.29±0.03 μg/mL, n=14, P=0.006) (FIG. 4B). In males, plasma omentin 1 concentrations were significantly different between lean (0.33±0.02 μg/mL, n=18) and obese subjects (0.28±0.02 μg/mL, n=8, P=0.01), but not between lean and overweight subjects (0.31±0.02 μg/mL, n=13, P=0.23, FIG. 4B). A notable sex difference in circulating omentin 1 levels is clear when comparing lean females with lean males (0.39±0.03 μg/mL vs. 0.33±0.02 μg/mL, P=0.04, FIG. 4B).

4. Human Plasma Omentin 1 Levels Correlate Negatively with Obesity and Insulin Resistance Markers.

Figure 5:
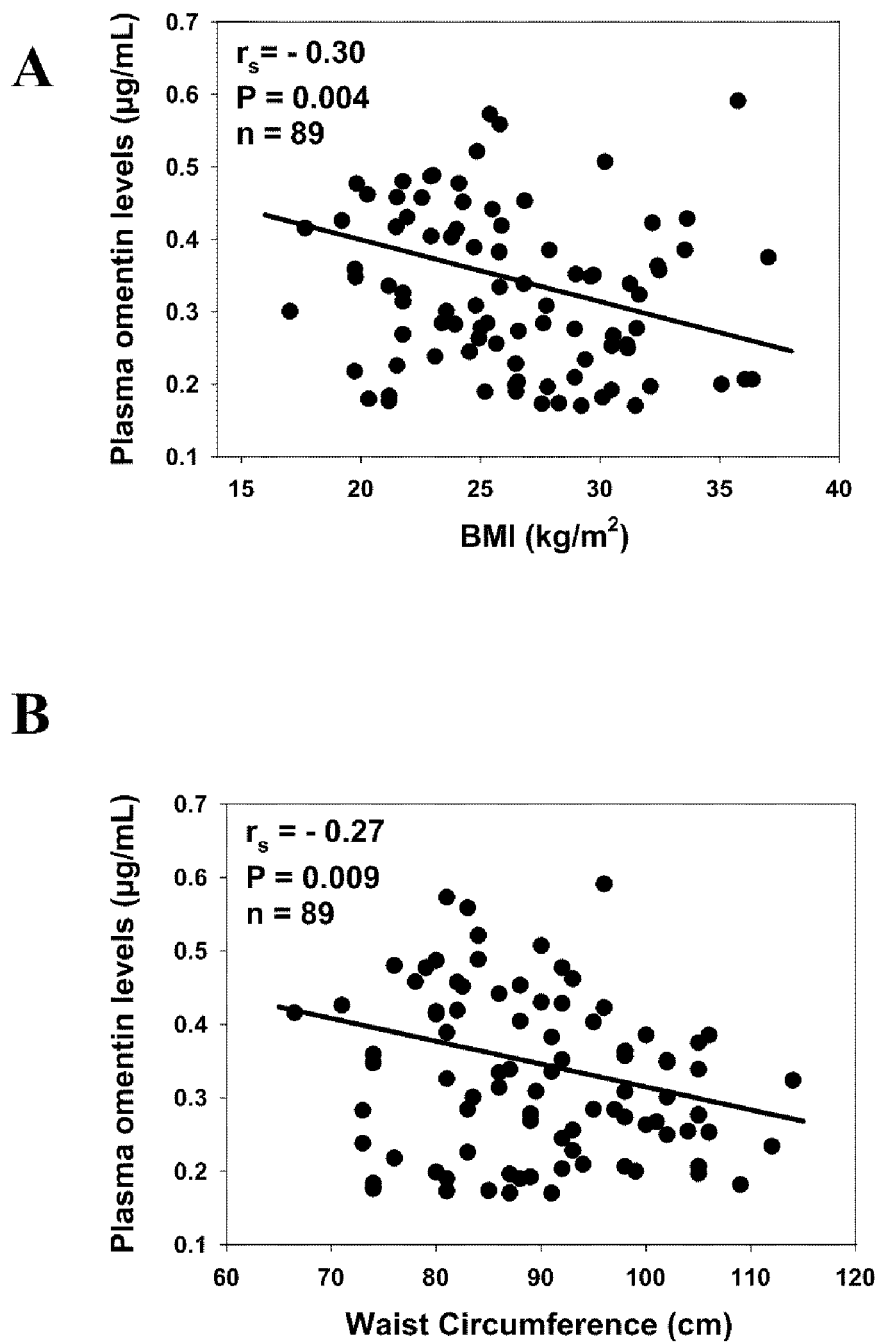
FIG. 5 shows circulating plasma omentin 1 levels correlate negatively with obesity and insulin resistance markers. Plasma omentin 1 levels correlate significantly with (A) BMI; (B) waist circumference; (C) HOMA; and (D) plasma adiponectin; Spearman rank correlations adjusted for sex and age.
Figure 5:
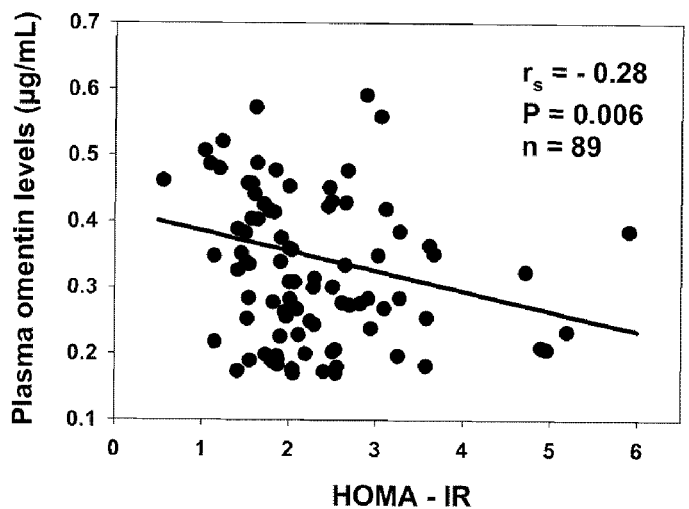
Figure 5:
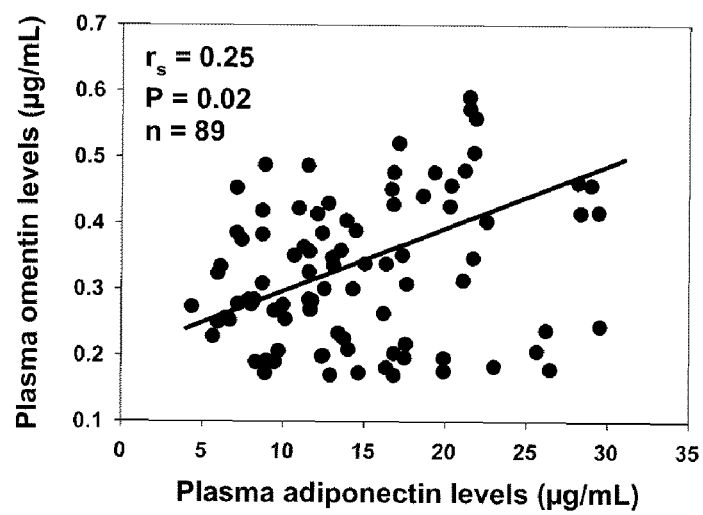

Significant Spearman rank correlation coefficients, adjusted for sex and age, were found between plasma omentin 1 levels and BMI ($r_s$=−0.30, P=0.004), waist circumference ($r_s$=−0.27, P=0.009), HOMA ($r_s$=−0.28, P=0.006), leptin ($r_s$=−0.39, P=0.0001), and adiponectin levels ($r_s$=0.25, P=0.02) (FIG. 5).

Further confirming these results, using a variance components analysis, adjusted for sex, age and family structure (Table 2), omentin 1 levels exhibited a significant negative correlation with BMI (β=−0.05, P=0.01), HOMA (β=−0.06, P=0.008), waist circumference (β=−0.03, P=0.002), and leptin levels (β=−0.04, P=0.006).

TABLE 2

| Covariate | β | SE | P |
|---|---|---|---|
| BMI (kg/m²) | −0.05 | 0.02 | 0.01 |
| Adiponectin (μg/mL) | 0.05 | 0.02 | 0.004 |
| Leptin (ng/mL) | −0.04 | 0.01 | 0.006 |
| HOMA Index | −0.06 | 0.02 | 0.008 |
| HDL cholesterol (mmol/L) | 0.02 | 0.007 | 0.02 |
| Waist Circumference (cm) | −0.03 | 0.009 | 0.002 |
| LDL cholesterol (mmol/L) | −0.002 | 0.002 | 0.45 |
| Triglycerides (mmol/L) | −0.03 | 0.02 | 0.13 |
| Total Cholesterol (mmol/L) | −0.0005 | 0.002 | 0.86 |
| Insulin (μU/mL) | −0.03 | 0.03 | 0.19 |
| Glucose (mg/dL) | 0.009 | 0.01 | 0.51 |
| SBP (mmHg) | −0.01 | 0.008 | 0.15 |
| DBP (mmHg) | −0.005 | 0.01 | 0.63 |

These data also indicated that plasma omentin 1 levels correlated positively with adiponectin (β=0.05, P=0.004) and HDL levels (β=0.02, P=0.02). When the variance components analysis was adjusted for sex, age, family structure and BMI, only adiponectin and leptin levels retained their correlations with omentin 1 levels (β=0.04, P=0.04, and β=−0.05, P=0.02, respectively). When waist circumference was included in the analysis instead of BMI, all correlations were statistically non-significant.

Adiponectin levels were determined in fasting plasma samples using a commercial radioimmunoassay kit (Linco Research, Saint Louis, Mo.). The samples were diluted at 1:500 and analyzed in duplicate. The gamma counts were measured on an automated Packard Cobra-II Auto Gamma counter (Perkin-Elmer, Wellesley, Mass.). The measurements with counts differing by >10% were rejected and the samples retested. The samples that did not fall within the detection limits of the assay were excluded.

5. Omentin Gene Expression Correlates Negatively with Body Mass Index.

Figure 6:
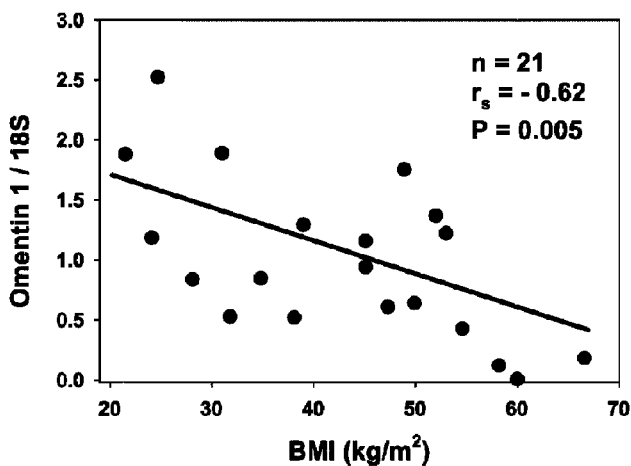
FIG. 6 shows visceral adipose omentin 1 and 2 gene expression levels are decreased with BMI. Visceral adipose omentin 1 and 2 mRNA/18S RNA ratio, measured by quantitative RT-PCR, were negatively correlated with BMI (Spearman correlations adjusted for sex and age, A and B, respectively). There was a significant positive correlation between omentin 1 and 2 gene expression levels (Spearman rank correlation adjusted for sex and age, C).
Figure 6:
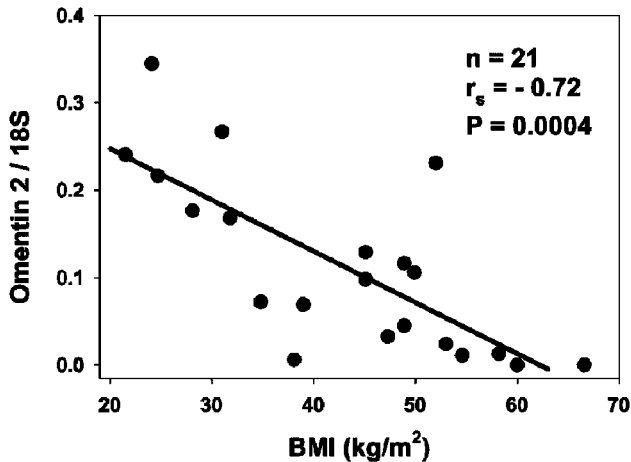
Figure 6:
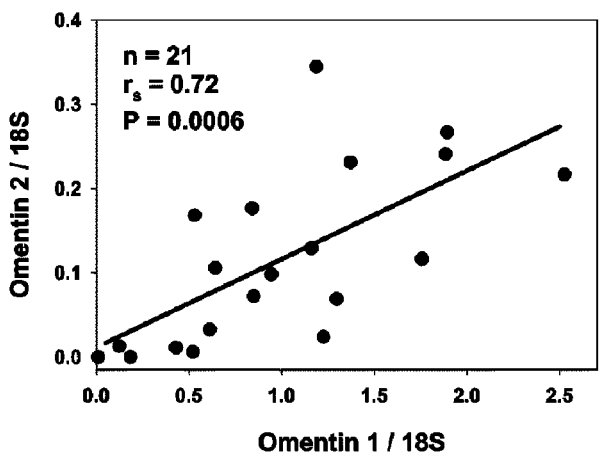

Omentin 1 and omentin 2 mRNA levels were measured in visceral fat from surgical subjects by real time QRT-PCR. Using Spearman regression analysis adjusted for sex and age, significant negative correlations between BMI and omentin 1 (n=21, $r_s$=−0.62, P=0.005) and omentin 2 mRNA levels ($r_s$=−0.72, P=0.0004) were found (FIGS. 6A and 6B). Additionally, when comparing omentin 1 and omentin 2 gene expression, a highly significant positive correlation was observed (n=21, $r_s$=0.72, P=0.0006, FIG. 6C).

Omentin 1 and omentin 2 mRNA levels were measured by real time quantitative RT-PCR (QRT-PCR) in a LightCycler 480 (Roche Applied Science, Indianapolis, Ind.). Total RNA was extracted from omental adipose tissue samples with Trizol (Invitrogen, Carlsbad, Calif.). Total RNA was reverse transcribed using the Roche Transcriptor cDNA kit. cDNA was quantified using LightCycler 480 Probes Master kit (Roche Applied Science, Indianapolis, Ind.) and Taqman probe/primer sets (omentin 1—Hs00214137_m1; omentin 2—Hs00365614_m1; 18S RNA—Hs999999_s1; Applied Biosystems, Foster City, Calif.). 18S mRNA was used as an internal control for normalization. Each sample was run in duplicate. Duplicates exhibiting standard deviations of more than 0.25 CT were repeated. Normalized gene expression values were obtained using LightCycler Relative Quantification software (LightCycler 480—Roche Applied Science, Indianapolis, Ind.).

6. Omentin 1 Gene Expression Correlates Positively with Omentin 1 Plasma Levels.

Figure 7:
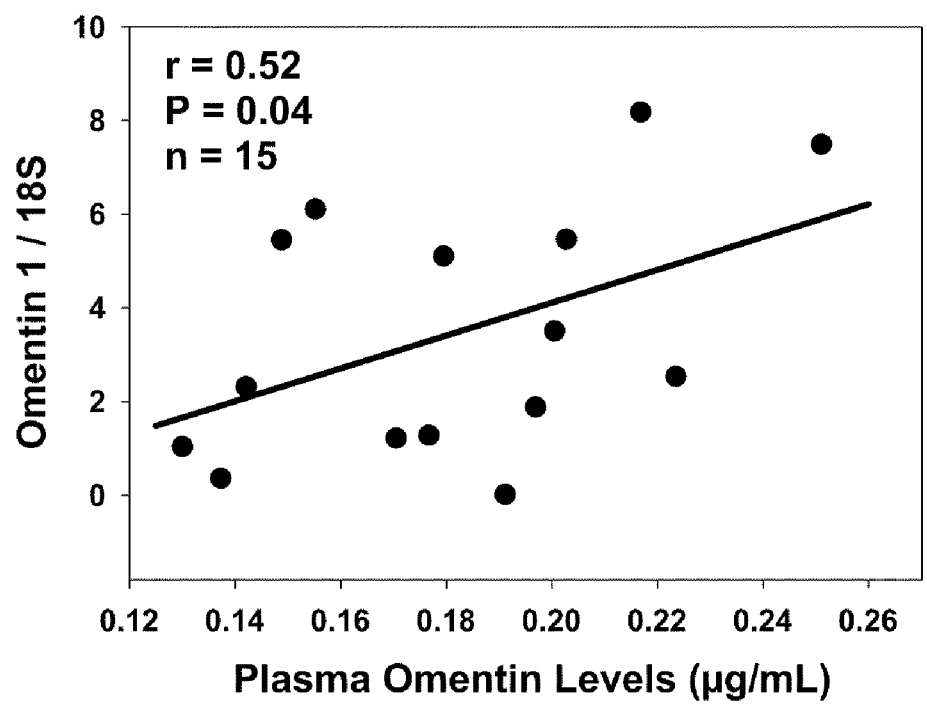
FIG. 7 shows omentin 1 mRNA levels were positively correlated with human plasma omentin 1 concentrations. Visceral omentin 1 mRNA/18S RNA ratio, measured by quantitative RT-PCR, were positively correlated with human plasma omentin 1 levels (Spearman rank correlation).

To determine if a linear relationship exists between omentin gene expression and plasma omentin levels, visceral adipose gene expression of omentin was compared to plasma omentin levels from a subgroup of the surgical subjects. Omentin 1 mRNA levels were positively correlated with omentin 1 plasma levels (n=15, $r_s$=0.52, P=0.04, FIG. 7), thus, illustrating a positive relationship between omentin gene regulation and omentin levels in the circulation.

7. Statistical Analysis.

Data are expressed as means±SE. Initially differences within BMI-discordant sib pairs were evaluated using the paired t-test. Differences in metabolic characteristics between lean, overweight and obese subjects were evaluated using one-way Pos-hoc Tukey pairwise comparisons were performed for variables that were significantly different by one-way ANOVA. Data were tested for normality of distribution by the Shapiro-Wilk test. In consequence, HOMA, leptin, and triglyceride levels were log transformed to obtain a normal distribution. Spearman rank correlations were used to estimate relationships between omentin and other quantitative variables. In order to adjust for family structure, variance components analysis as implemented in SOLAR, which allows the inclusion of a kinship matrix to allow for residual intra-pair correlations between relatives, was used to confirm all analyses involving Amish subjects (25). Other analyses were performed using SAS 9.1 software package (SAS, Cary, N.C.).

8. Discussion.

As previously reported (11), visceral fat is the tissue exhibiting the highest level of omentin 1 expression. However, compared with omentin 1, omentin 2 is expressed in considerably lower levels in visceral fat and in higher levels in the intestine. Luminal release of omentin 2 and the difference in visceral fat expression of the two isoforms may explain why circulating levels of omentin 2 were not detected in human plasma. Although omentin 1 and omentin 2 exhibit a different pattern of tissue expression, they may share some similar regulation by obesity as evidenced by the negative correlations between the gene expression of both isoforms and BMI, and the positive correlation with each other in visceral adipose tissue.

Plasma omentin 1 levels were measured in a well characterized genetically homogeneous population of Old Order Amish of Lancaster County who have been recruited for the Amish Family Diabetes Study conducted at the University of Maryland School of Medicine (24). As expected for a visceral depot-specific adipocytokine that may affect positively insulin sensitivity, higher plasma omentin 1 levels were observed in lean versus obese and overweight subjects independent of sex. Further evidence to suggest that omentin 1 may be involved in some aspect of insulin sensitivity is the negative correlation between omentin 1 plasma levels and measurements of insulin resistance (HOMA). Moreover, negative correlations between plasma omentin 1 levels and BMI, waist circumference and leptin values were observed. These data suggest that obesity negatively regulates omentin expression and release into the circulation.

Additionally, plasma omentin 1 levels were positively correlated with HDL levels. Negative correlations without statistical significance were found between omentin 1 and triglycerides, and LDL (Table 2). These results indicate that higher omentin 1 levels are associated with a healthy lipid profile and taken in light of the previous data suggest that high omentin 1 levels may be associated with a lower risk of metabolic syndrome.

It is interesting to note that this pattern of results for omentin 1 is similar to adiponectin, an insulin sensitizer and cardio-protective adipokine (31-36). In fact, circulating plasma adiponectin levels were positively correlated with plasma omentin 1 values in this study. The inverse relationship between obesity and both omentin and adiponectin may suggest similar regulation. It is also possible that regulation of omentin may be dependent on adiponectin or vice versa. Visfatin, the proposed insulin-mimetic adipokine, also shows negative correlations between plasma levels and BMI (37).

A striking difference in plasma omentin 1 levels between lean females and males was observed. Epidemiological studies have shown that women have a relatively lower risk of cardiovascular disease than men (38, 39). Thus, without being bound by any theory, higher omentin 1 levels in women may be associated with this lower risk. Future studies will be required to address this apparently divergent regulation of omentin between males and females.

When plasma omentin is adjusted for BMI in the covariate analysis, a loss of significance is observed with most significant traits except plasma leptin and adiponectin. Additionally, if waist circumference is adjusted in the analysis instead of BMI, then all correlations are statistically non-significant. Thus, these results reinforce the concept that plasma omentin 1 levels are highly regulated by obesity and lose significant associations with obesity-dependent variables when adjusted by BMI or waist circumference.

To extend the relationship between plasma omentin and obesity to omentin gene expression, omentin 1 and 2 mRNA levels were measured in visceral and subcutaneous adipose tissue from surgical subjects. Neither omentin 1 nor 2 shows significant levels of expression in subcutaneous adipose tissue. Similar to plasma omentin levels, visceral adipose omentin gene expression for both isoforms, omentin 1 and omentin 2, is lower in the obese state than in the lean one, as evidenced by negative correlations between gene expression and BMI. In fact, mRNA levels for omentin 1 and 2 are highly correlated with each other in omental adipose tissue. In contrast with omentin and adiponectin which show obesity-dependent decreases in gene expression, visfatin was shown to have obesity-dependent increases in visceral fat gene expression (37, 40, 41).

Correlation between omentin 1 mRNA and plasma omentin 1 levels was also observed, suggesting that the regulation of omentin 1 gene expression in visceral fat can predict the circulating levels of omentin 1.

Although the data clearly supports regulation of omentin by obesity, omentin may also be regulated by inflammation. Other studies have shown that omentin 1/intelectin 1 expression is altered in inflammatory states (12, 42). Obesity itself is associated with low levels of chronic inflammation, which may contribute to the regulation in the role of omentin in human physiology (43-45). Consequently, weight loss and different inflammatory states could be seen as potential modulators of omentin expression and function.

In summary, plasma omentin 1 and both omentin 1 and 2 mRNAs were found to be inversely related to obesity. Females have higher levels of circulating omentin 1 and a larger range of variation with BMI. Plasma omentin 1 correlates negatively with BMI, leptin, waist circumference and HOMA and positively with adiponectin and HDL. Association with these metabolic indices suggests that a higher omentin levels may be seen as a marker for leanness or as a positive factor that opposes the obese state and its pathophysiological consequences.

EXAMPLE II

Additional studies were undertaken to develop a further understanding of the biology of ometin 1 and 2 which are described as follows.

1. Omentin is a Secretory Protein.

Figure 8:
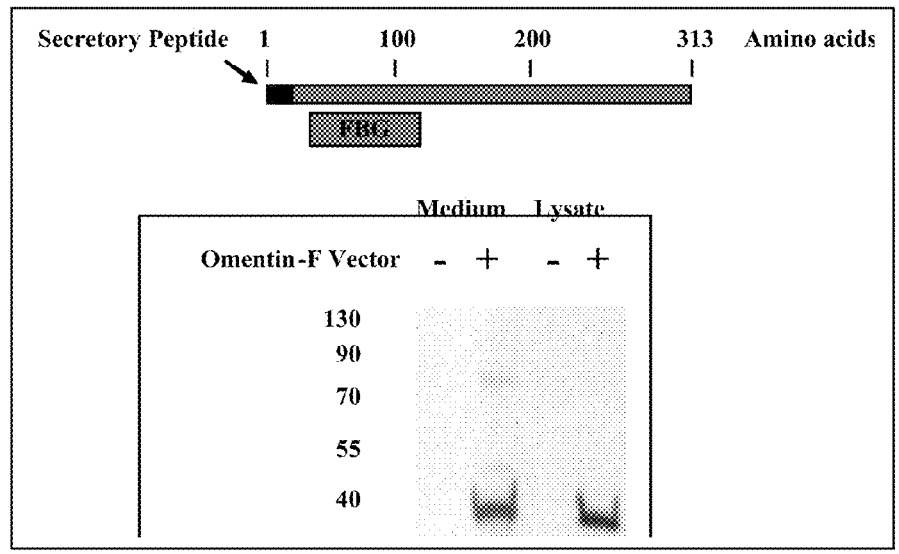
FIG. 8 shows a map of the FLAG-tagged omentin 1 protein, and a western blot analysis demonstrating the presence of omentin 1 protein in both cell lysates and culture media.

In order to obtain soluble omentin protein for functional analysis and to test whether omentin is secreted from cells as suggested from sequence analysis, the Flag peptide sequence was attached to the coding region of omentin (omentin-F) at the carboxy-terminus by PCR. The coding region of omentin was then subcloned into a CMV (Cytomegalovirus) promoter-driven mammalian expression vector, pcDNA3 (Invitrogen) (same for omentin 2—data not shown). The resultant plasmid (omentin-F) was confirmed by sequencing and used to transiently transfect into HEK-293T cells using Lipofectamine Plus (Life technology). The cells were cultured in DMEM with 10% FBS. The culture medium was collected and cells were lysed 48 hours after transfection for immunoblotting. In brief, the fractions were immunoblotted with rabbit polyclonal serum directed to omentin. As a result, omentin-F was detected in both culture media and cell lysate from the cells transfected with omentin-F plasmid, but not from empty vector-transfected control cells (FIG. 8). This data established that omentin is a secretory protein.

2. Omentin Secretion is Depot-Specific in Human Adipose Tissue Explant Culture.

Figure 9:
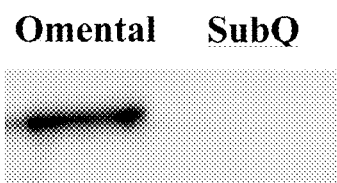
FIG. 9 depicts an immunoblot of serum-free media (500 ul) from Day 8 adipose tissue explant culture that was concentrated and immunoblotted with monoclonal anti-omentin antiserum.

Omental and subcutaneous (SubQ) adipose tissue fragments were placed in explant culture for up to 8 days as previously described (77). A total of ~5 g of each depot (subcutaneous and omental) was used. The explant culture medium used was serum-free M199 supplemented with 25 mM HEPES and bicarbonate supplement with insulin (7 nM). Cultures (0.4 g/15 ml) were kept in petri dishes at 37° C. under 5% $CO_2$ and media was replenished every second day. Concentrated media from day 8 explant culture was immunoblotted with monoclonal anti-omentin antibodies. This data is representative of several independent experiments with different subject's tissue cultured for 1-8 days. Depot specificity of secretion was always evident under all culture conditions. Omentin 2 is 50× lower and quantifiable only by 2D gel/western (FIG. 9).

3. Omentin1-F Increases Insulin-Stimulated 2-Deoxyglucose (2-DG) Transport in 3T3-L1 Adipocytes.

Figure 10:
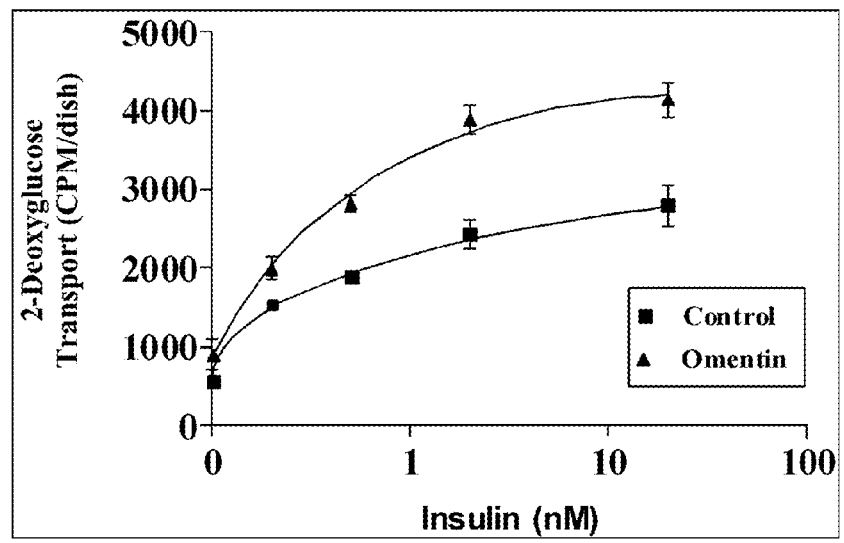
FIG. 10 demonstrates that omentin 1 increases insulin-stimulated 2-DG transport. Mean±SEM. (n=3) are shown from three independent experiments. Each measurement was conducted in triplicate.

Many adipose factors modulate glucose, fat metabolism and insulin sensitivity in vitro or in vivo. Whether omentin affects insulin action in 3T3-L1 adipocytes was examined using 2-DG transport assay (78). To obtain a considerable amount of omentin, HEK-293T cell lines were established that were stably transfected with the plasmid omentin-F/pcDNA3 or empty vector pcDNA3. Conditioned serum-free media from this stable cell line was used for stimulation. 3T3-L1 adipocytes were stimulated with serum-free conditioned medium from empty vector-transfected (Control) or omentin-F-transfected HEK-293T cells with increasing concentrations of insulin. Omentin 1 was found to increase insulin-stimulated 2-DG transport (FIG. 10). Mean±SEM. (n=3) are shown from three independent experiments. Each measurement was conducted in triplicate. The estimated omentin concentration is about 400 ng/ml.

4. Purified Omentin 1 Enhances Insulin-Stimulated Glucose Transport in Human Fat Cells.

Figure 11:
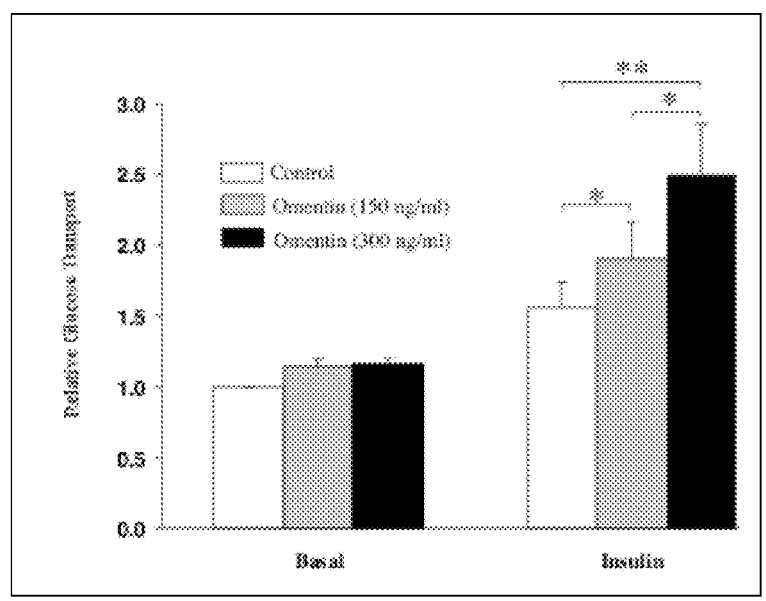
FIG. 11 shows that omentin 1 augments insulin-stimulated glucose transport in isolated human subcutaneous fat cells. Purified omentin-F (grey and black bar) was added or not 1 hour prior to insulin-stimulation (60 pM). Transport assays were performed in triplicate, averaged and normalized to the amount of lipid in each fat cell sample.

To confirm the results in mouse 3T3-L1 adipocytes, insulin-stimulated glucose transport into freshly isolated human fat cells was measured in the presence or absence of purified omentin (88). Fat cell suspensions were preincubated with purified omentin-F (150 ng/ml or 300 ng/ml final) for 1 hour prior to addition of 60 pM insulin and labeled glucose for another hour. After separation in silicone oil, fat cell-associated radioactivity was measured in a liquid scintillation counter (Beckman LS6500). Purified omentin augmented insulin-stimulated glucose transport in subcutaneous adipocytes from four subjects (FIG. 11). Similar results were obtained in visceral fat cells (data not shown). This result is of particular relevance since purified human omentin was shown to affect human fat cell insulin action similarly in murine 3T3-L1 adipocytes.

5. Omentin 2 Stimulates Basal Glucose Transport in 3T3-L1 Adipocytes.

Figure 12:
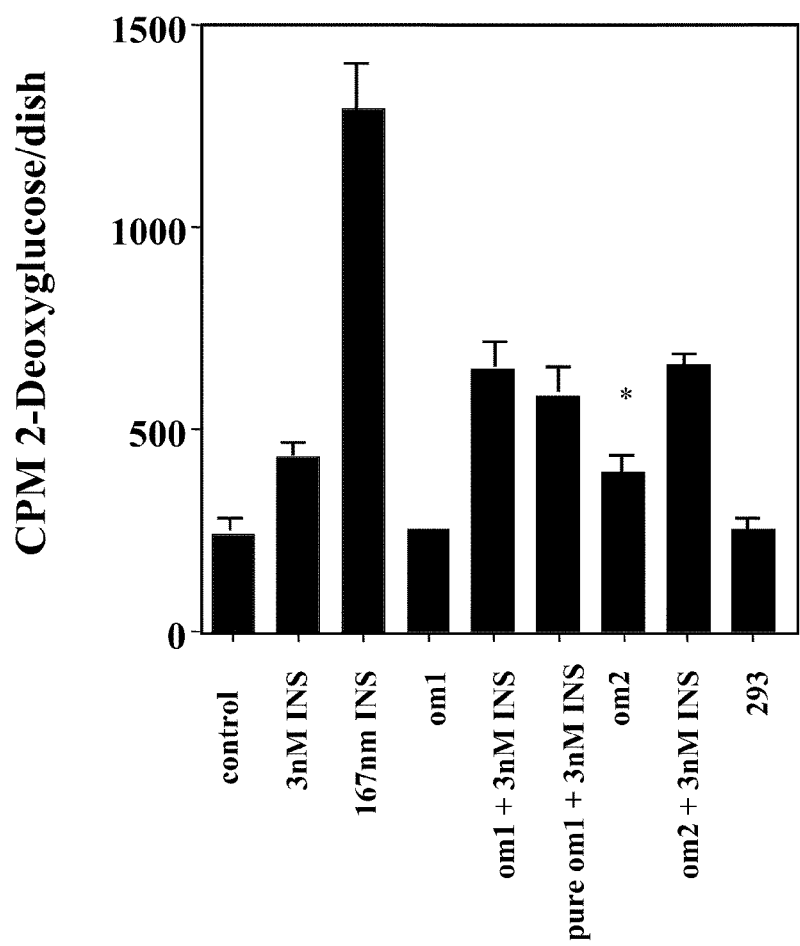
FIG. 12 shows that omentin 2 stimulates basal glucose transport in 3T3-L1 adipocytes. Omentin 1 treatment 400 ng/ml ("om1") and omentin 2~100 ng/ml ("om2"). 293 cell conditioned medium alone ("293"). n=2 independent experiments.

3T3-L1 adipocytes were stimulated with purified omentin 1, omentin 1 or omentin 2 conditioned media. In contrast to omentin 1, which acts as an insulin sensitizer, omentin 2 acted to raise basal glucose transport to the level of 3 nM insulin alone suggesting that it may have insulin-mimetic activity (FIG. 12). Omentin 2 alone should be compared to basal control ("control") or 293 conditioned media without omentin ("293").

6. Omentin 1/2 is Expressed in the Stromal-Vascular Cell Fraction of Visceral Adipose Tissue.

Figure 13:
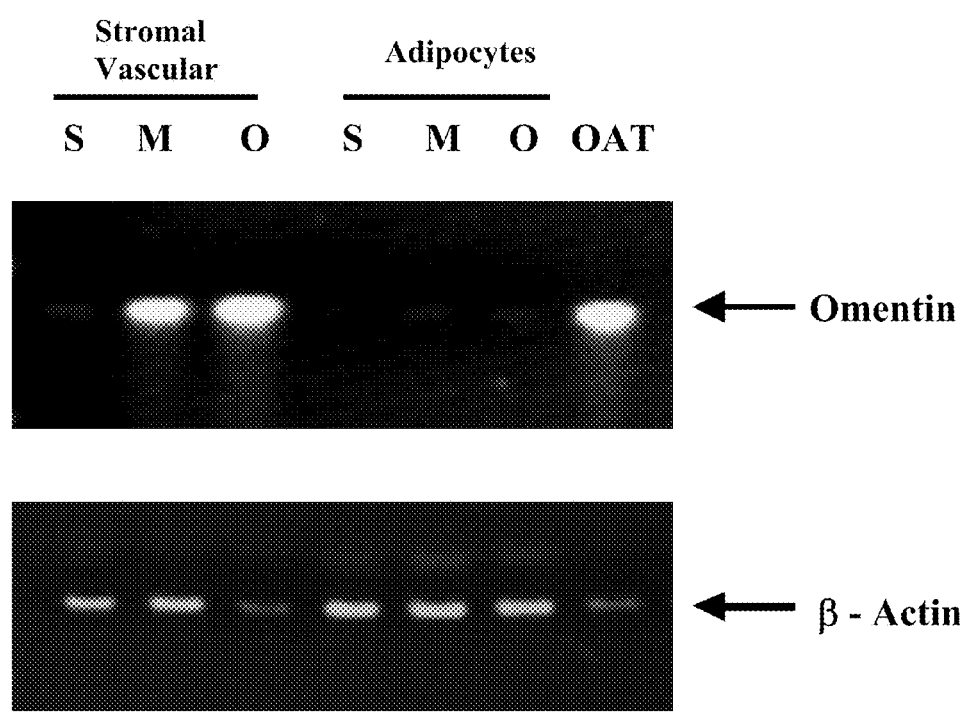
FIG. 13 depicts the results of omentin RT-PCR of stromal vascular cells and adipocytes isolated from human subcutaneous (S), mesenteric (M) and omental (O) fat depots. Intact omental adipose tissue RNA was used as a positive control for omentin RNA (OAT). Omentin mRNA is only detected in visceral fat stromal vascular cells (M and O) and not in adipocytes (S, M, O) or subcutaneous stromal vascular cells. Actin RT-PCR was done in parallel RNA samples.

Immunofluorescence localization of omentin in adipose tissue sections suggested that omentin may not be localized in the adipocyte itself but potentially in the extracellular matrix and the surrounding stromal cells. To test this hypothesis, human subcutaneous (S), mesenteric (M) and omental (O) adipose tissue were collagenase digested. Stromal-vascular cells (SV) were separated from adipocytes by floatation/centrifugation (69). Total RNA was isolated from both SV cells and adipocytes using the Trizol reagent (Life Technologies). Single step non-quantitative RT-PCR was performed using both actin and omentin-specific primers (Titan Single-Step RT-PCR, Roche). This primer set recognizes both omentin 1 and omentin 2. The RT-PCR results in FIG. 13 confirm the visceral fat-specific expression of omentin that had previously been demonstrated by whole tissue northern blot (data not shown) and immunofluorescence. Strikingly, stromal-vascular cells from visceral depots (M and O) exhibited strong expression of omentin. Moreover, no omentin expression was detected in any adipocyte RNA. Thus, it was concluded that the visceral fat expression and secretion of omentin occurs in the stromal-vascular cells, not the adipocytes.

7. Omentin 1 Gene Expression in Human Omental/Subcutaneous Adipose Tissue and Isolated Visceral Stromal-Vascular Cells (SVC).

Figure 14:
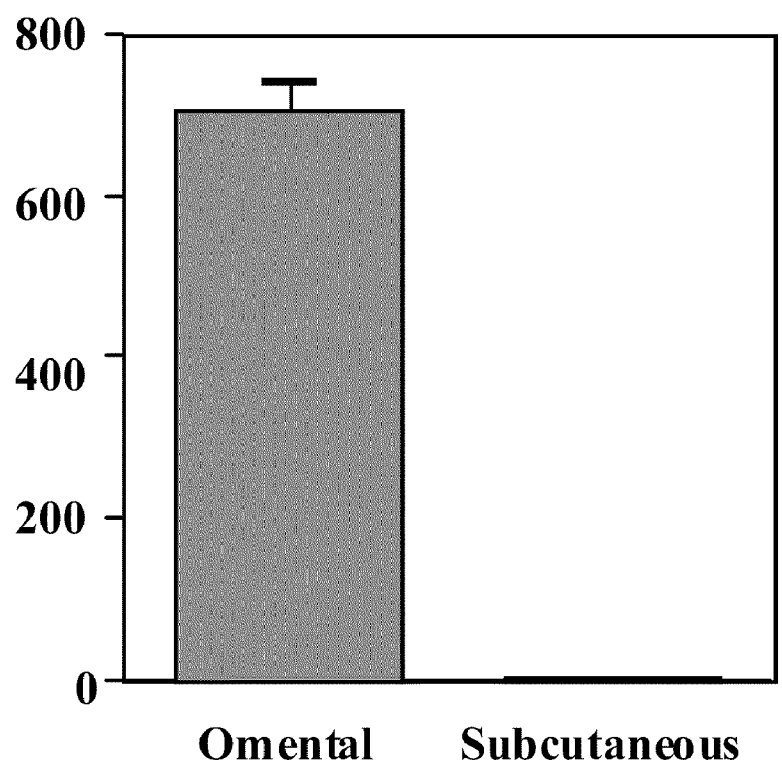
FIG. 14 depicts the results of real time quantitation of omentin mRNA in human adipose tissue ("omental" or "subcutaneous"). Omentin 1 gene expression was normalized to ribosomal protein gene, 36B4 gene expression. AU (arbitrary units)

Omentin mRNA levels were determined by quantitative RT-PCR (Q-RT-PCR) using the Lightcycler (Roche Diagnostics). Ribosomal protein gene, 36B4 expression was used as a reference "house keeping" gene. Total RNA (0-100 ng) isolated from omental, subcutaneous fat and confluent visceral SVC treated with TNF-alpha (10 ng/ml) for 8 or 24 hrs was subjected to a "hot start" one-step RT-PCR(RT-30 min. at 61° C.) reaction using the Lightcycler-RNA Master w/SYBR Green 1 (Roche Diagnostics). Primers used were (5'-3') CTCCAGACACTGGGACATA (Forward), TGACCCTCATTCCAGCACA (Reverse) for omentin (56° C.-annealing) and CGACCTGGAAGTCCAACTAC (Forward), ATCTGCTGCATCTGCTTG (Reverse) for 36B4 (53° C.-annealing). Omentin Q-RT-PCR exhibited PCR efficiency of greater than 1.91 (2.0 is perfect) and melting curve analysis revealed a single amplicon peak at 85° C. Endothelial cell (EC) gene expression was determined using Taqman probes purchased from ABI. EC gene expression was normalized to 36B4 expression (see methods below). Omentin mRNA levels were shown to be 500 fold higher than subcutaneous adipose tissue (FIG. 14) which confirms earlier non-quantitative data indicating essentially no expression of omentin in non-visceral fat.

Figure 15:
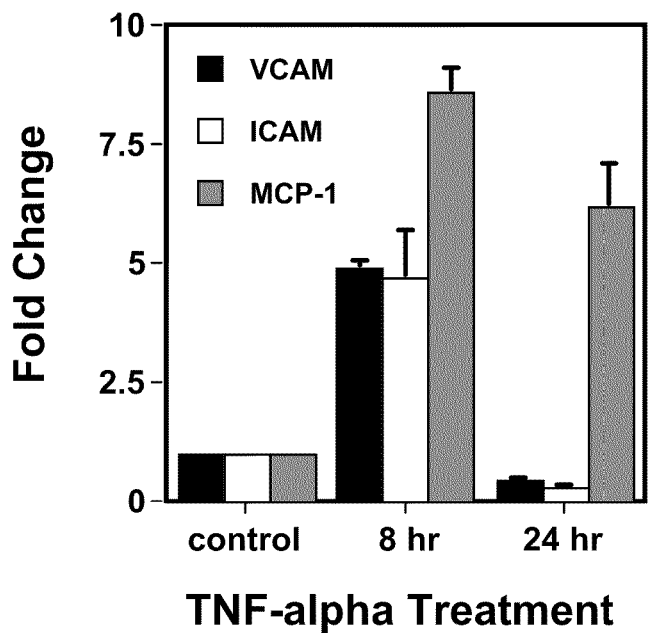
FIG. 15 depicts omentin (A) and endothelial cell (B) gene expression in SVC culture after 5 ng/ml TNF-alpha treatment. TNF experiments are expressed as fold change from untreated control. Gene expression was normalized to Cyclophilin A expression for endothelial cell genes.
Figure 15:
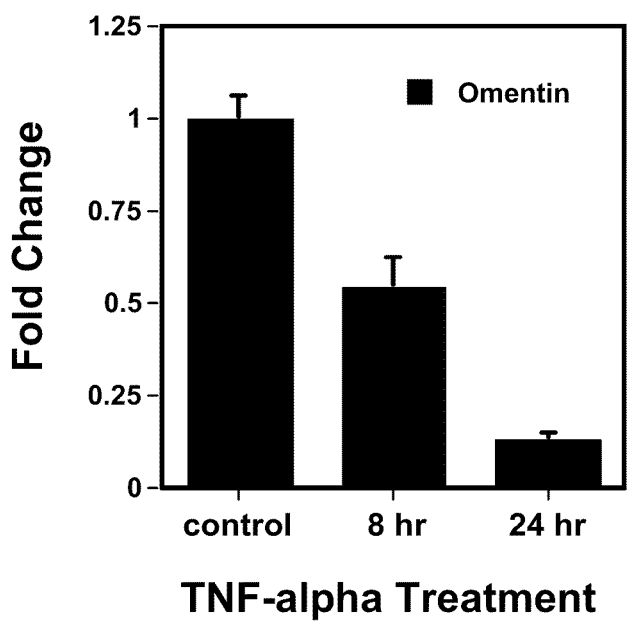

The up-regulation of adhesion molecules VCAM and ICAM, as well as the monocyte chemoattractant MCP-1 in response to TNF-alpha stimulation, illustrates the normal physiological responsiveness of cultures containing visceral EC (69) to this cytokine (FIG. 15A). In the same SVC cultures, omentin gene expression exhibited a time-dependent decrease (87% after 24 hr) in response to TNF-alpha treatment (FIG. 15B). This data indicated that omentin 1 is expressed and negatively regulated by TNF-alpha, an insulin resistance-promoting cytokine, in visceral SVC culture.

8. Omentin Protein Expression Increased in Overweight Versus Obese Adipose Tissue.

Figure 16:
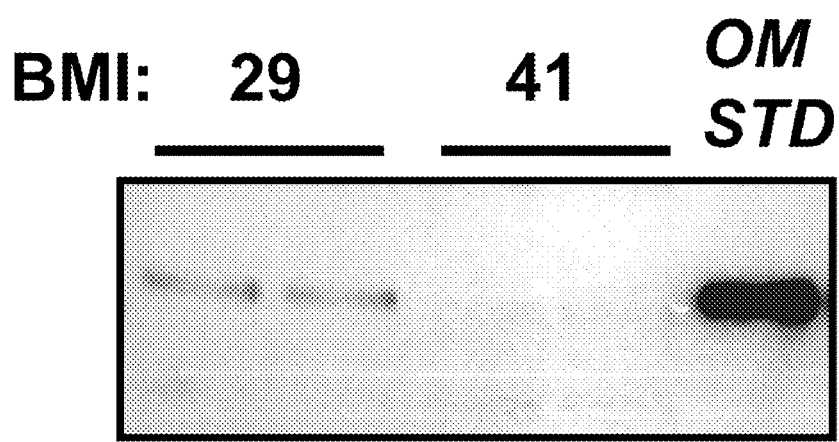
FIG. 16 shows a western blot of omental adipose tissue lysates from one overweight (BMI=29) and one obese patient (BMI=41), versus an omentin standard.

A western blot analysis was performed on omental adipose tissue lysates from derived from one overweight (BMI=29) and one obese patient (BMI=41). The results in FIG. 16 illustrate the BMI-dependent variation in tissue omentin protein previously seen by gene expression and plasma omentin (87).

9. Omentin 1 and 2 SNPs

Figure 17:
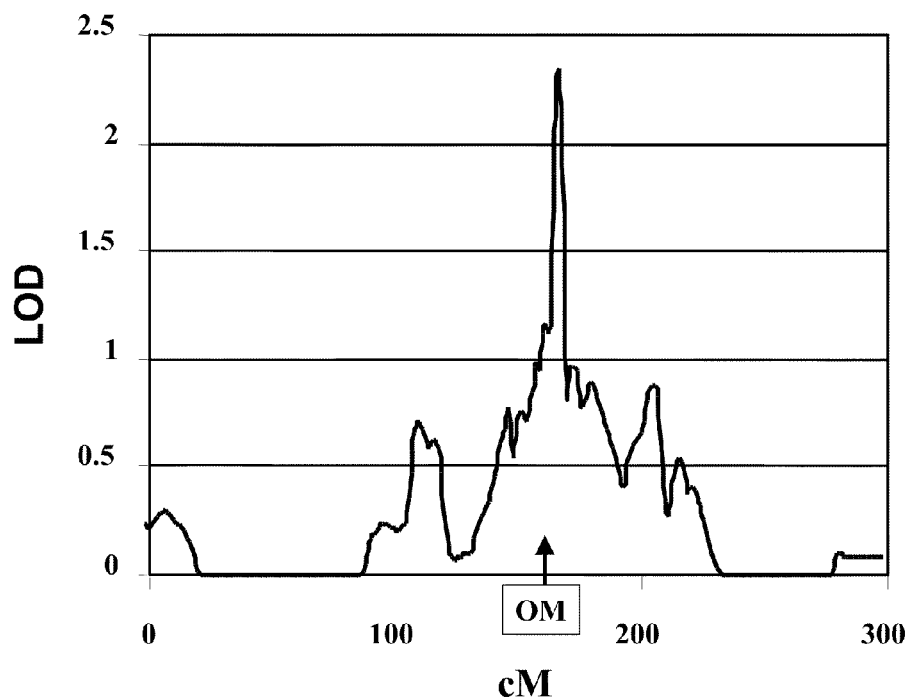
FIG. 17 shows a genetic linkage peak on chromosome 1 for the trait diabetes/impaired glucose tolerance. This area has been identified by Alan Shuldiner's genome wide scan of the Amish as a strong candidate gene area for diabetes susceptibility genes. The omentin genes are found under the largest linkage peak.

Omentin 1 and 2 genes are next to each other on chromosome 1 in an area that has been identified to have strong genetic linkage to diabetes or impaired glucose tolerance by the Amish Family Diabetes Study (AFDS) (66) (FIG. 17). 48 single nucleotide polymorphisms (SNPs) were genotyped across the omentin 1 (OM1) and omentin 2 (OM2) genes. A partial list (Table 3) illustrates association of three SNPs with impaired glucose tolerance (bold).

TABLE 3

Omentins SNPs in AFDS subjects with impaired glucose tolerance (n = 148, IGT), and normal glucose tolerance (n = 358, NGT).

| SNP name | Location | Major/Minor alele | IGT vs. NGT† Odds ratio | p-value |
|---|---|---|---|---|
| Rs4656955 | Om1 intron 7 | G/A | NS | 0.975 |
| Rs3766356 | Om1 intron 7 | C/T | NS | 0.940 |
| Rs3820094 | Om1 intron 7 | G/A | 0.876 | 0.919 |
| Rs2274906 | Om1 intron 6 | G/A | 1.405 | 0.102 |
| Om-7296 | Om1 intron 5 | C/T | NS | 0.481 |
| Rs2236515 | Om1 intron 5 | C/T | NS | 0.385 |
| Rs2297559 | Om1 intron 2 | A/G | NS | 0.824 |
| Om-72386 | Om2 intron 7 | T/C | NS | 0.578 |
| Om-73721 | Om2 intron 7 | T/C | 0.637 | 0.357 |
| Rs1556519 | Om2 intron 6 | A/G | 0.454 | 0.005 |
| Om-74938 | Om2 intron 6 | C/T | 1.684 | 0.006 |
| Om-74965 | Om2 intron 6 | T/C | 1.012 | 0.919 |
| Om-76859 | Om2 exon 5 | C/T | NS | 0.242 |
| Rs3829790 | Om2 intron 4 | G/A | NS | 0.387 |
| Rs6680969 | Om2 exon 4 | T/C | NS | 0.455 |
| Rs4656971 | Om2 intron 3 | G/T | NS | 0.580 |
| Rs2252389 | Om2 intron 2 | C/T | NS | 0.645 |
| Rs4596920 | Om2 intron 2 | C/T | NS | 0.539 |
| Om-79443 | Om2 intron 2 | CCCAG/— | 0.273 | 0.017 |
| Om-80082 | Om2 intron 2 | A/G | NS | 0.919 |
| Om-81237 | Om2 promoter | C/T | 0.418 | 0.012 |
| Om-81739 | Om2 promotor | —/TAA | NS | 0.611 |
| Om-81873 | Om2 promotor | G/T | 0.302 | 0.001 |

Figure 18:
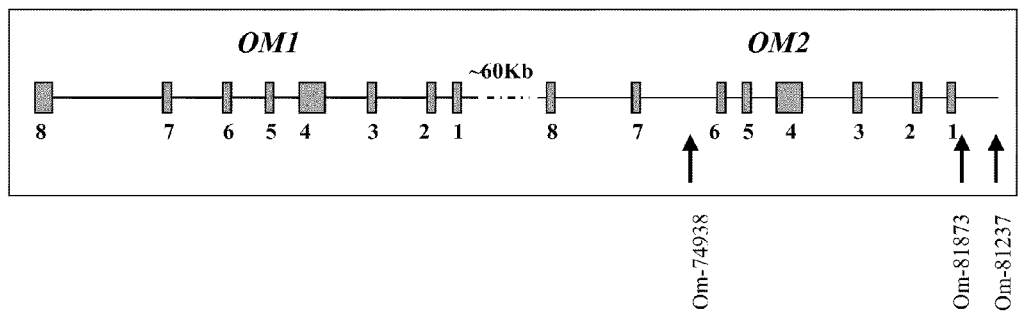
FIG. 18 shows a map of the omentin 1 and 2 genes, with arrows depicting two SNPs in the proximal promoter of omentin 2 (within 1 Kb of transcription start site) and one in intron 6 of omentin 2. Om-74938-0.30 allele freq., Om-81237-0.1 allele freq., Om-81873-0.1 allele freq.

Two SNPs of particular interest were found in the proximal promoter of omentin 2 (within 1 Kb of transcription start site). FIG. 27 shows the location of the SNP Om-81237 c/t polymorphism and the SNP Om-81837 g/t polymorphism (underlined and in bold) in relation to the translational start site (the ATG that is also underlined and in bold) of omentin 2. One SNP of particular interest in intron 6 of omentin 2 is the OM-74938 c/t polymorphism. FIG. 28 shows the location of the SNP Om-74938 c/t polymorphism (underlined and in bold) in relation to the end of exon 6 of omentin 2 (in capital letters and underlined). See also the arrows in FIG. 18 for the location of these three SNPs in relation to the chromosomal map. The major allele of an additional SNP in intron 6 was associated with IGT. These data implicate omentin 2 as the disease associated gene at this locus.

Figure 19:
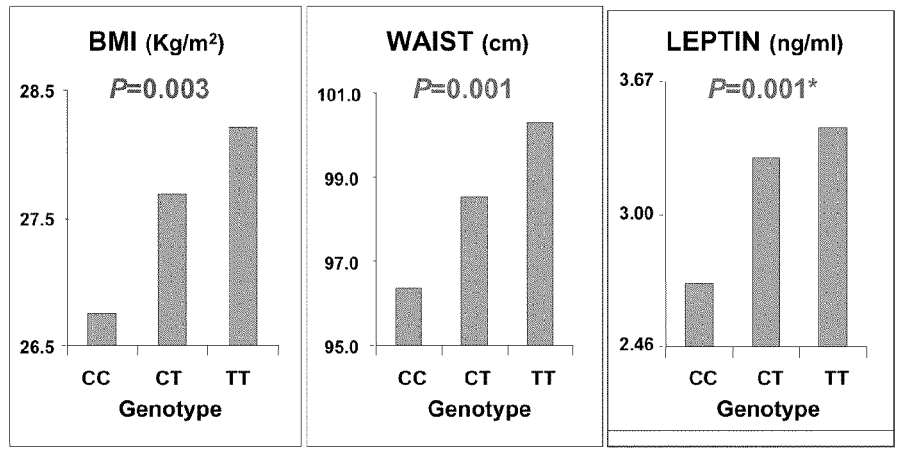
FIG. 19 shows omentin 2 intron 6 SNP associates with metabolic syndrome-related traits in Amish Family Diabetes Study (AFDS) (n=867). The rare allele (frequency=0.3) associates with BMI-dependent quantitative traits just as plasma omentin 1 and visceral adipose omentin 1 gene expression do (87).
Figure 19:
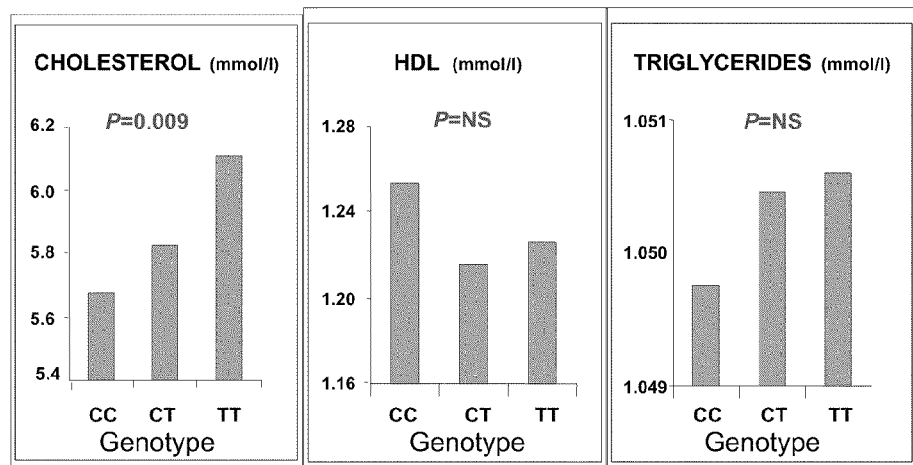
Figure 19:
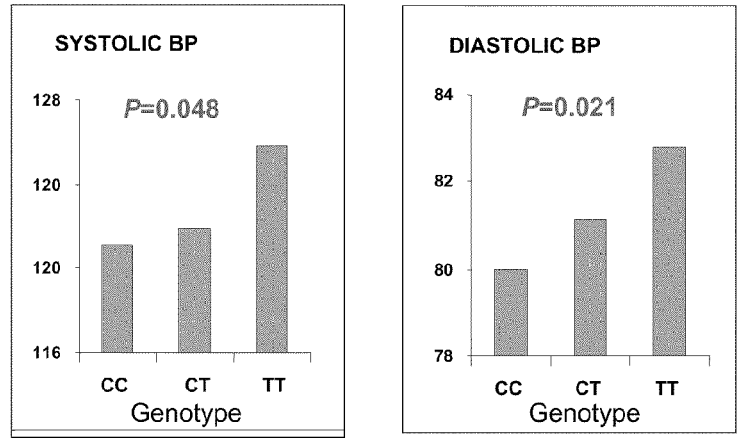
Figures 20, 21:
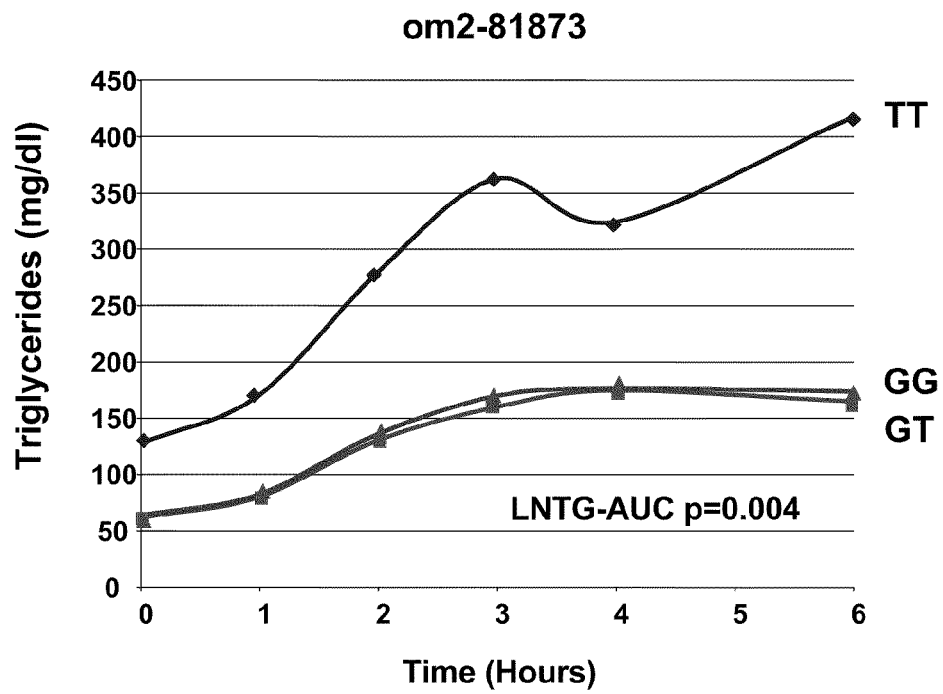
FIG. 20 shows omentin 2 promoter SNP-om2-81873 TT allele associates with high TG excursion. Amish subjects enrolled in the HAPI (Heredity and Phenotype Intervention) study were challenged with a high fat meal (n=432) and monitored for triglyceride excursions over 6 hours. This data is consistent with the hypothesis that decreases in omentin 2 will cause intestinal overproduction of TG rich lipoprotein particles.
FIG. 21 shows omentin 1 and 2 tissue distribution by QRT-PCR. Gene expression of omentin 1 (OM1) and omentin 2 (OM2) are normalized to cyclophilin. OM2 is 50 fold lower in omental fat than OM1. In contrast, OM2 is 5 fold higher in small intestine than OM1. Direct comparisons between OM1 and OM2 levels in this table cannot be made unless gene expression is converted to copy number (data not shown).

The three omentin 2 polymorphisms were also identified as associating with impaired glucose tolerance, quantitative traits such as BMI, waist, leptin, cholesterol, blood pressure (FIG. 19) and high triglyceride excursions after a high fat challenge (FIG. 20). This data strongly implicates omentin 2 as a susceptibility gene for metabolic syndrome and its composite traits.

10. Omentin 1 and 2 Tissue Distribution by QRT-PCR

FIG. 21 shows omentin 1 and 2 tissue distribution by QRT-PCR. Gene expression of omentin 1 (OM1) and omentin 2 (OM2) are normalized to cyclophilin. OM2 is 50 fold lower in omental fat than OM1. In contrast, OM2 is 5 fold higher in small intestine than OM1. Direct comparisons between OM 1 and OM2 levels in this table cannot be made unless gene expression is converted to copy number (data not shown).

11. Plasma Omentin 1 Levels are Reduced in Subjects with Elevated Inflammation.

Figure 22:
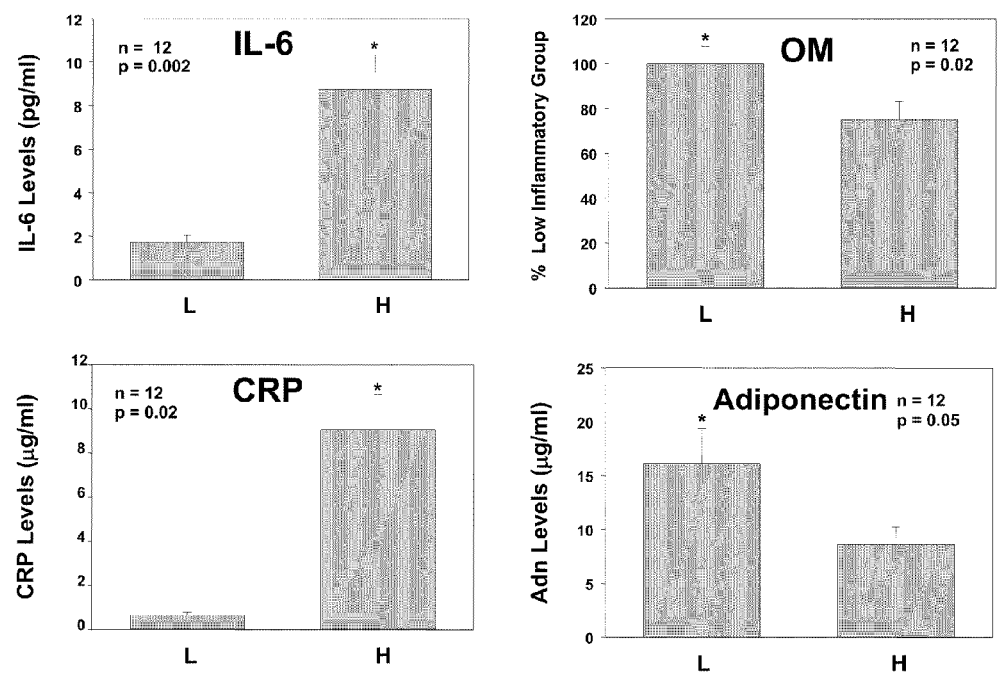
FIG. 22 shows the results of measurement of omentin, adiponectin, IL-6 and CRP in the plasma of 12 subjects with high (H) or low (L) subacute inflammatory states. Experimental means were analyzed by Mann-Whitney.

Plasma samples were obtained from Dr. Alan Shuldiner's Amish Family Genetic Studies and quantitated for omentin levels and inflammatory markers as described above. Premenopausal Amish females were grouped by moderately high and low inflammatory status using IL-6 and CRP as markers. As it was hypothesized, plasma omentin levels are significantly reduced with elevated systemic inflammation even in this small unpaired group (FIG. 22). There are striking similarity between omentin and adiponectin since adiponectin levels also decrease in parallel to omentin just as they did with obesity (above preliminary data).

12. Modulation of Omentin 1/2 Gene Expression by Inflammatory Mediators in Visceral Adipose.

Figure 23:
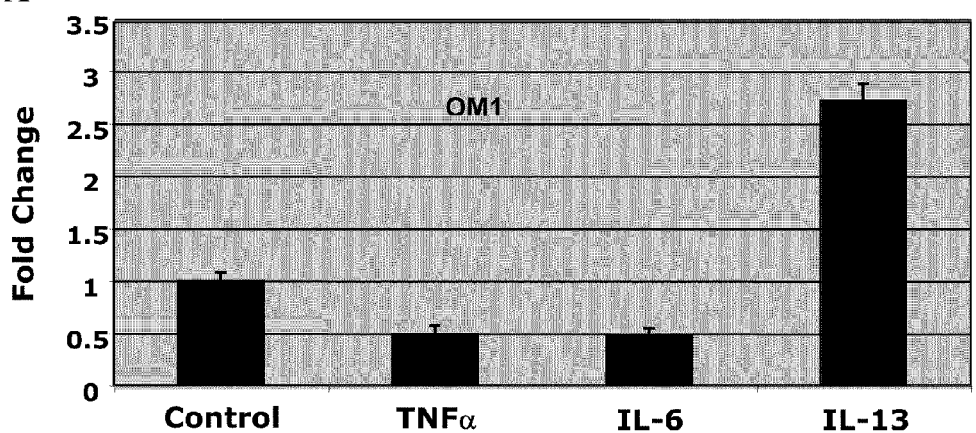
FIG. 23 shows omentin gene expression (A: omentin 1 ("OM1"); B: omentin 2 ("OM2"); in adipose explant culture after 24 hour treatment with cytokines. Omental adipose tissue from three surgical subjects was cultured as described. Gene expression assays were done in triplicate. p<0.05 for all comparisons.
Figure 23:
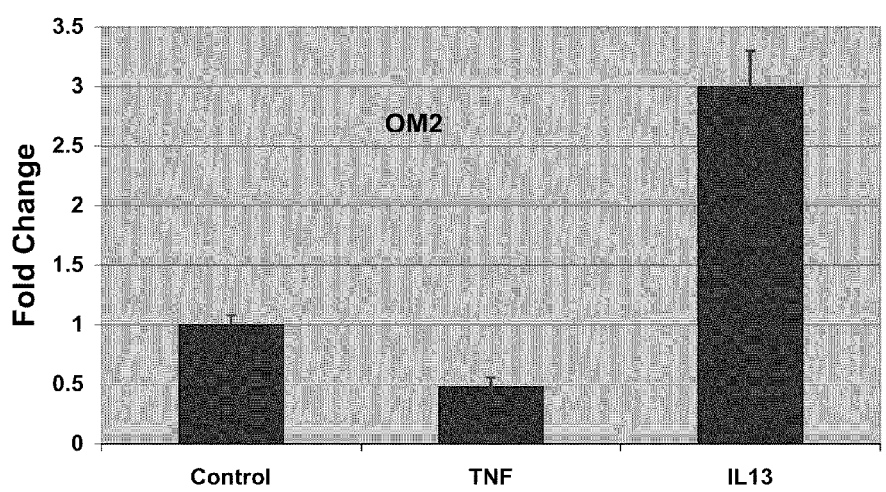

Omental adipose tissue was cultured for 24 hours in the absence or in the presence of 5 ng/ml TNF-alpha, 10 ng/ml IL-6 or 10 ng/ml IL-13. Total RNA was extracted from explant tissue and subjected to QRT-PCR as discussed previously. As would be predicted from the effect of TNF-alpha on omentin in cultured stromal-vascular cells, the proinflammatory cytokines, TNF-alpha and IL-6, decreased omentin gene expression 50% in adipose explant culture (FIGS. 23A & B). In contrast, the anti-inflammatory cytokine, IL-13, increased omentin gene expression 2.5 to 3 fold over untreated cultures (FIGS. 23A & B). In light of the antagonistic effects of IL-13 on macrophage TNF-alpha production (82), it is theorized that a reduction of the inflammatory environment (TNF-alpha or IL-6) by IL-13 would positively affect omentin gene expression. In addition, omentin expression in untreated explants may be low due to an elevated inflammatory state that may be exacerbated by additional TNF-alpha.

13. Human Aortic Endothelial Cells (HAEC) and Caco-2 Cells Express Omentin 1/2 Appropriately to Study Transcription Analysis In Vitro.

Figure 24:
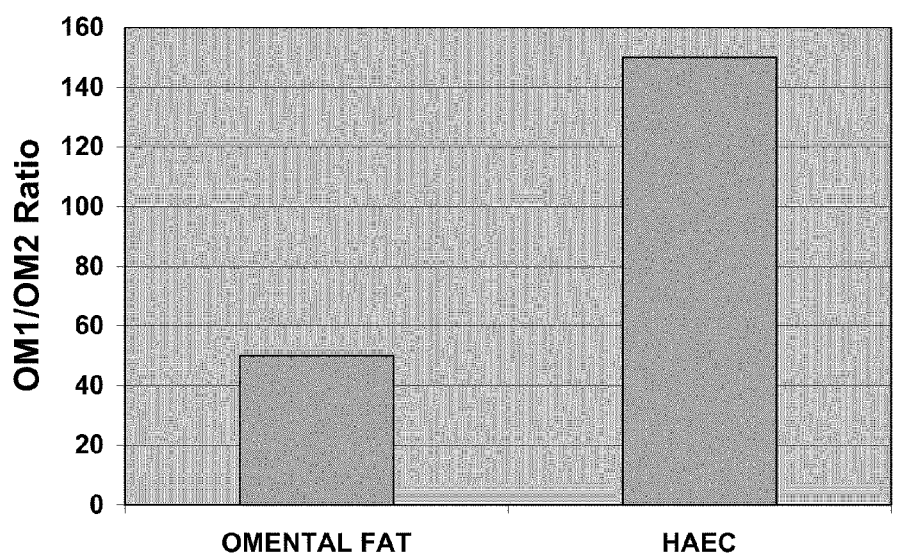
FIG. 24 shows the relative gene expression ratios of omentin 1 and 2 in human aortic endothelial cells (HAEC) (FIG. 24A) and Caco-2 cells (FIG. 24B), versus the noted tissues.
Figure 24:
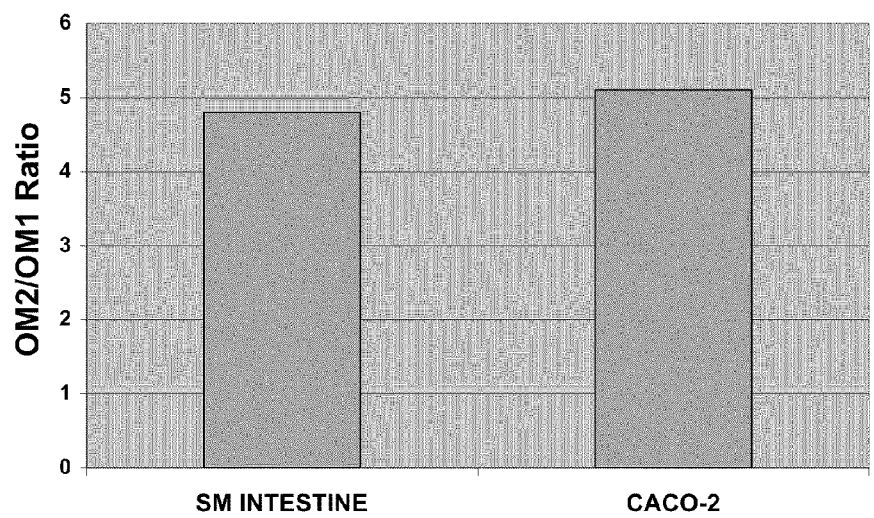

Caco-2 (human intestinal adenocarcinoma) and primary HAEC cells (commercially available, Clonetics) were found to exhibit an inverse ratio of omentin 2 to omentin 1 compared to intact intestine or visceral fat/heart (FIG. 24). Ratios of normalized quantitative RT-PCR data indicate that the cell types proposed to study the transcriptional regulation of tissue and cell specificity of omentin 1 and 2 are appropriate since the divergence between the two isoforms is preserved. FIG. 24A—OM1/OM2: FIG. 24B—OM2/OM1.

14. HAEC Cells Transactivate the Omentin 1 Promoter and Respond to Pro-Inflammatory Cytokines.

Figure 25:
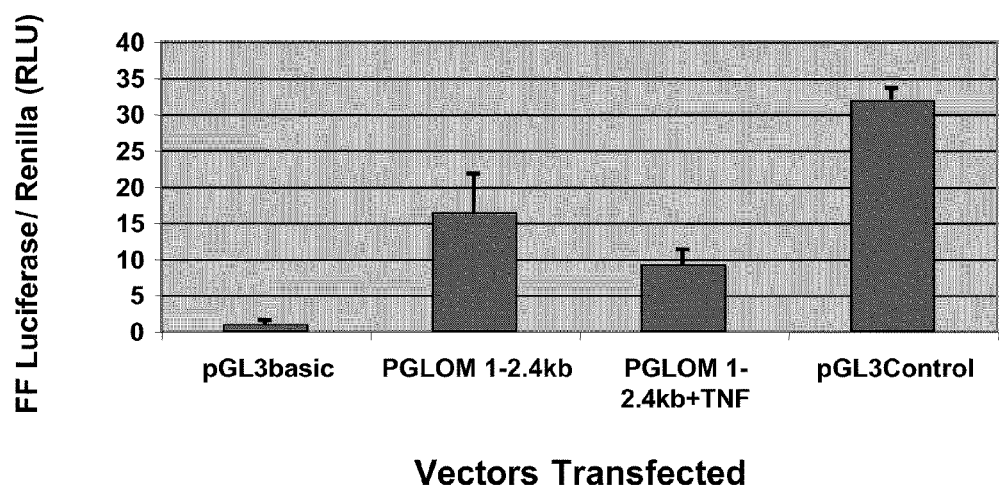
FIG. 25 demonstrates that HAECs transactivate the 2.4 Kb omentin 1 promoter. Primary human aortic endothelial cells transfected with 2.4 kb omentin 1 promoter exhibited 50% transcriptional activation of the control SV40 promoter and also decreased activation after 24 hour treatment with 5 ng/ml TNF-alpha.

Preliminary data shows that HAEC cells transactivate the omentin 1 promoter and respond to pro-inflammatory cytokines. In particular, the results shown in FIG. 25 demonstrate that HAECs transactivate the 2.4 kb omentin 1 promoter. Primary human aortic endothelial cells were transfected with the 2.4 kb omentin 1 promoter and were found to exhibit 50% transcriptional activation of the control SV40 promoter and also decreased activation after 24 hour treatment with 5 ng/ml TNF-alpha.

Figure 26:
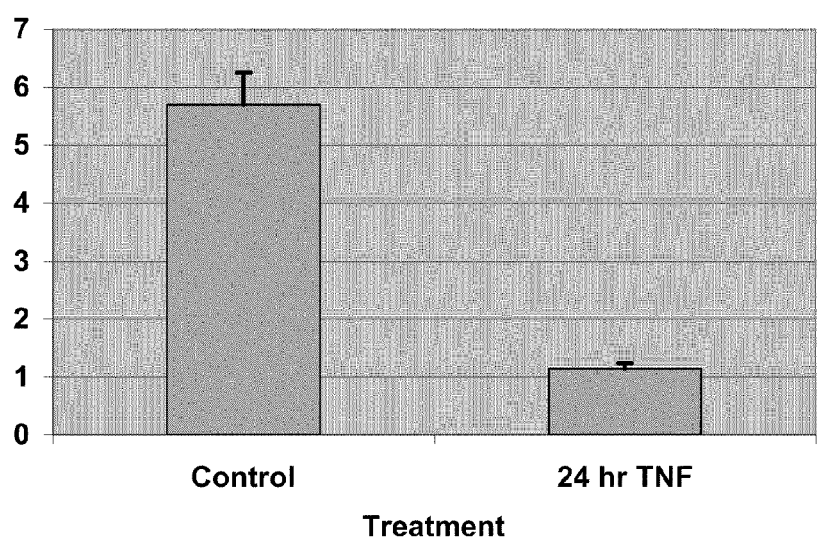
FIG. 26 demonstrates that TNF-alpha decreases omentin gene expression in HAEC. Primary human aortic endothelial cells were treated with 5 ng/ml TNF-alpha for 24 hours. QRT-PCR of omentin 1 was normalized to cyclophilin A and expressed as arbitrary units (AU).

Furthermore, the results shown in FIG. 26 demonstrate that TNF-alpha decreases omentin gene expression in HAECs. Primary human aortic endothelial cells were treated with 5 ng/ml TNF-alpha for 24 hours. QRT-PCR of omentin 1 was normalized to cyclophilin A and expressed as arbitrary units (AU).

While the invention has been described with reference to certain particular embodiments thereof, those skilled in the art will appreciate that various modifications may be made without departing from the spirit and scope of the invention. The scope of the appended claims is not to be limited to the specific embodiments described.

All patents, patent applications, patent application publications, journal articles, books, manuals and other documents referred to herein are incorporated by reference in their entirety. Each of the following references has been cited in this application:

REFERENCES

1. Sharma A M: Adipose Tissue: a mediator of cardiovascular disease. *Int J Obes* 26:Suppl 4:S5-S7, 2002
2. Felber J P, Golay A: Pathways from obesity to diabetes. *Int J Obes* 26:Suppl 2:S39-S45, 2002
3. Kershaw E E, Flier J S: Adipose tissue as an endocrine organ. *J Clin Endocrinol Metab* 89:2548-2556, 2004
4. Galuska D A, Khan L K: Obesity: a public health perspective. In *Present Knowledge in Nutrition*. 8th ed. Ed. International Life Sciences Institute, 2001, p. 531-542
5. Bjorntorp P: Metabolic implications of body fat distribution. *Diabetes Care* 14:1132-1143, 1991
6. Brunzell J D, Hokanson J E: Dyslipidemia of central obesity and insulin resistance. *Diabetes Care* 22:Suppl 3:C10-13, 1999
7. Lemieux S: Contribution of visceral obesity to the insulin resistance syndrome. *Can J Appl Physiol* 26:273-290, 2001
8. Johnson J A, Fried S K, Pi-Sunyer F X, Albu J B: Impaired insulin action in subcutaneous adipocytes from women with visceral obesity. *Am J Physiol Endocrinol Metab* 280:E40-E9, 2001
9. Van Pelt R E, Jankowski C M, Gozansky W S, Schwartz R S, Kohrt W M: Lower-body adiposity and metabolic protection in postmenopausal women. *J Clin Endocrinol Metab* 90:4573-4578, 2005
10. Fried S K, Ross, R J R: The biology of visceral adipose tissue. In *Handbook of Obesity*, 2nd edition, Edited by Bray G A, Bouchard C, James W P T, 2005
11. Yang R Z, Lee M J, Hu H, Pray J, Wu H B, Hansen B C, Shuldiner A R, Fried S K, McLenithan J C, Gong D W: Identification of omentin as a novel depot-specific adipokine in human adipose tissue: possible role in modulating insulin action. *Am J Physiol Endocrinol Metab* 290:E1253-E1261, 2006
12. Schaffler A, Neumeier M, Herfarth H, Furst A, Scholmerich J, Buchler C: Genomin structure of human omentin, a new adipocytokine expressed in omental adipose tissue. *Biochim Biophys Acta* 1732:96-102, 2005
13. Kralisch S, Klein J, Bluher M, Paschke R, Stumvoll M, Fasshauer M: Therapeutic perspectives of adipocytokines. *Expert Opin Pharmacother* 6:863-72, 2005
14. Tsuji S, Uehori J, Matsumoto M, Suzuki Y, Matsuhisa A, Toyoshima K, Seya T: Human intelectin is a novel soluble lectin that recognizes galactofuranose in carbohydrate chains of bacterial cell wall. *J Biol Chem* 276:23456-23463, 2001
15. Suzuki Y A, Shin K, Lonnerdal B: Molecular cloning and functional expression of a human intestinal lactoferrin receptor. *Biochemistry* 40:15771-15779, 2001
16. Lee J K, Schnee J, Pang M, Wolfert M, Baum L G, Moremen K W, Pierce M: Human homologs of the Xenopus oocyte cortical granule lectin XL35. *Glycobiology* 11:65-73, 2001
17. Komiya T, Tanigawa Y, Hirohashi S: Cloning of the novel gene intelectin, which is expressed in intestinal Paneth cells in mice. *Biochem Biophys Res Commun* 251:759-762, 1998
18. Fu M, Gong D W, Damcott C, Sabra M, Yang R Z, Pollin T I, Tanner K, Ott S, McLenithan J C, Fried S K, O'Connell J R, Mitchell B D, Shuldiner A R: Systematic analysis of omentin 1 and omentin 2 on Iq23 as candidate genes for type 2 diabetes in the Old Order Amish (Abstract). *Diabetes* 53: A59, 2004
19. St Jean P, Husueh W C, Mitchell B, Ehm M, Wanger M, Burns D, and Shuldiner A R: Association between diabetes, obesity, glucose and insulin levels in the Old Older Amish and SNPs on 1q21-23. *Am J Hum Genet* 67:332, 2000.
20. Elbein S C, Hoffman M D, Teng K, Leppert M F, Hasstedt S J: A genome-wide search for type 2 diabetes susceptibility genes in Utah Caucasians. *Diabetes* 48:1175-1182, 1999
21. Hanson R L, Ehm M G, Pettitt D J, Prochazka M, Thompson D B, Timberlake D, Foroud T, Kobes S, Baier L, Burns D K, Almasy L, Blangero J, Garvey W T, Bennett P H, Knowler W C: An autosomal genomic scan for loci linked to type II diabetes mellitus and body-mass index in Pima Indians. *Am J Hum Genet* 63:1130-1138, 1998
22. Vionnet N, Hani El H, Dupont S, Gallina S, Francke S, Dotte S, De Matos F, Durand E, Lepretre F, Lecoeur C, Gallina P, Zekiri L, Dina C, Froguel P: Genomewide search for type 2 diabetes-susceptibility genes in French whites: evidence for a novel susceptibility locus for early-onset diabetes on chromosome 3q27-qter and independent replication of a type 2-diabetes locus on chromosome 1q21-q24. *Am J Hum Genet* 67:1470-1480, 2000
23. Wiltshire S, Hattersley A T, Hitman G A, Walker M, Levy J C, Sampson M, O'Rahilly S, Frayling T M, Bell J I, Lathrop G M, Bennett A, Dhillon R, Fletcher C, Groves C J, Jones E, Prestwich P, Simecek N, Rao P V, Wishart M, Foxon R, Howell S, Smedley D, Cardon L R, Menzel S, McCarthy M I: A genomewide scan for loci predisposing to type 2 diabetes in a U.K. population (the Diabetes UK Warren 2 Repository): analysis of 573 pedigrees provides independent replication of a susceptibility locus on chromosome 1 q. *Am J Hum Genet* 69:553-569, 2001
24. Hsueh W C, Mitchell B D, Aburomia, R, Pollin T I, Sakul H, Ehm M G, Michelsen B K, Wagner M J, St Jean P L, Knowler W C, Burns D K, Bell C J, Shuldiner A R: Diabetes in the Old Order Amish: Characterization and heritability analysis of the Amish Family Diabetes Study. *Diabetes Care* 23:595-601, 2000
25. Almasy L, Blangero J: Multipoint quantitative-trait linkage analysis in general pedigrees. *Am J Hum Genet* 62:1198-1211, 1998
26 Stothard P: The Sequence Manipulation Suite: JavaScript programs for analyzing and formatting protein and DNA sequences. *Biotechniques* 28:1102-1104, 2000
27. Montague C T, Prins J B, Sanders L, Digby J E, O'Rahilly S: Depot- and sex-specific differences in human leptin mRNA expression: implications for the control of regional fat distribution, *Diabetes* 46:342-347, 1997

28. Alessi M C, Peiretti F, Morange P, Henry M, Nalbone G, Juhan-Vague I: Production of plasminogen activator inhibitor 1 by human adipose tissue: possible link between visceral fat accumulation and vascular disease. *Diabetes* 46:860-867, 1997

29. Arita Y, Kihara S, Ouchi N, Takahashi M, Maeda K, Miyagawa J, Hotta K, Shimomura I, Nakamura T, Miyaoka K, Kuriyama H, Nishida M, Yamashita S, Okubo K, Matsubara K, Muraguchi M, Ohmoto Y, Funahashi T, Matsuzawa Y: Paradoxical decrease of an adipose-specific protein, adiponectin, in obesity. *Biochem Biophys Res Commun* 257:79-83, 1999

30. Yang W S, Lee W J, Funahashi T, Tanaka S, Matsuzawa Y, Chao C L, Chen C L, Tai T Y, Chuang L M: Weight reduction increases plasma levels of an adipose-derived anti-inflammatory protein, adiponectin. *J Clin Endocrinol Metab* 86:3815-3819, 2001

31. Weyer C, Funahashi T, Tanaka S, Hotta K, Matsuzawa Y, Pratley R E, Tataranni P A: Hypoadiponectinemia in obesity and type 2 diabetes: close association with insulin resistance and hyperinsulinemia. *J Clin Endocrinol Metab* 86:1930-1935, 2001

32. Tschritter O, Fritsche A, Thamer C, Haap M, Shirkavand F, Rahe S, Staiger H, Maerker E, Haring H, Stumvoll M: Plasma adiponectin concentrations predict insulin sensitivity of both glucose and lipid metabolism. *Diabetes* 52:239-243, 2003

33. Yamauchi T, Kamon J, Waki H, Terauchi Y, Kubota N, Hara K, Mori Y, Ide T, Murakami K, Tsuboyama-Kasaoka N, Ezaki O, Akanuma Y, Gavrilova O, Vinson C, Reitman M L, Kagechika H, Shudo K, Yoda M, Nakano Y, To be K, Nagai R, Kimura S, Tomita M, Froguel P, Kadowaki T: The fat-derived hormone adiponectin reverses insulin resistance associated with both lipoatrophy and obesity. *Nat Med* 7:941-946, 2001

34. McLaughlin T, Abbasi F, Kim H S, Lamendola C, Schaaf P, Reaven G: Relationship between insulin resistance, weight loss, and coronary heart disease risk in healthy, obese women. *Metabolism* 50:795-800, 2001

35. Matsubara M, Maruoka S, Katayose S: Decreased plasma adiponectin concentrations in women with dyslipidemia. *J Clin Endocrinol Metab* 87:2764-2769, 2002

36. Zoccali C, Mallamaci F, Tripepi G, Benedetto F A, Cutrupi S, Parlongo S, Malatino L S, Bonanno G, Seminara G, Rapisarda F, Fatuzzo P, Buemi M, Nicocia G, Tanaka S, Ouchi N, Kihara S, Funahashi T, Matsuzawa Y: Adiponectin, metabolic risk factors, and cardiovascular events among patients with end-stage renal disease. *J Am Soc Nephrol* 13:134-141, 2002

37. Pagano C, Pilon C, Olivieri M, Mason P, Fabris R, Serra R, Milan G, Rossato M, Federspil G, Vettor R: Reduced plasma visfatin/pre B-cell colony enhancing factor in obesity is not related to insulin resistance in humans. *J Clin Endocrinol Metab* 91:3165-3170, 2006

38. Polk D M, Naqvi T Z: Cardiovascular disease in women: sex differences in presentation, risk factors, and evaluation. *Curr Cardiol Rep* 7:166-172, 2005

39. Milan E: Coronary artery disease. The other half of the heaven. *J Nucl Med Mol Imaging* 49:72-80, 2005

40. Berndt J, Kloting N, Kralisch S, Kovacs P, Fasshauer M, Schon M R, Stumvoll M, Bluher M: Plasma visfatin concentrations and fat depot-specific mRNA expression in humans. *Diabetes* 54: 2911-2916, 2005

41. Kern P A, Di Gregorio G B, Lu T, Rassouli N, Ranganathan G: Adiponectin expression from human adipose tissue: relation to obesity, insulin resistance, and tumor necrosis factor-alpha expression. *Diabetes* 52:1779-1785, 2003

42. Kuperman D A, Lewis C C, Woodruff P G, Rodriguez M W, Yang Y H, Dolganov G M, Fahy J V, Erle D J: Dissecting asthma using focused transgenic modeling and functional genomics. *J Allergy Clin Immunol* 116:305-311, 2005

43. Ryan A S, Nicklas B J: Reductions in plasma cytokine levels with weight loss improve insulin sensitivity in overweight and obese postmenopausal women. *Diabetes Care* 27:1699-1705, 2004

44. Weisberg S P, McCann D, Desai M, Rosenbaum M, Leibel R L, Ferrante A W: Obesity is associated with macrophage accumulation in adipose tissue. *J Clin Invest* 112: 1796-808, 2003

45. Heilbronn L K, Noakes M, Clifton P M: Energy restriction and weight loss on very-low-fat diets reduce C-reactive protein concentrations in obese, healthy women. *Arterioscler Thromb Vasc Biol* 21:968-970, 2001

46. R. S. Ahima, J. S. Flier: Adipose tissue as an endocrine organ. *Trends Endocrinol Metab* 11, 327-32, 2000

47. G. Ailhaud: Adipose tissue as an endocrine organ. *Int J Obes Relat Metab Disord* 24 Suppl 2, S1-3, 2000

48. S. Lemieux: Contribution of visceral obesity to the insulin resistance syndrome. *Can J Appl Physiol* 26, 273-90, 2001

49. J. D. Brunzell, J. E. Hokanson: Dyslipidemia of central obesity and insulin resistance. *Diabetes Care* 22 Suppl 3, C10-3, 1999

50. P. Arner: Differences in lipolysis between human subcutaneous and omental adipose tissues. *Ann Med* 27, 435-8, 1995

51. M. D. Jensen: Lipolysis: contribution from regional fat. *Annu Rev Nutr* 17, 127-39, 1997

52. S. K. Fried, D. A. Bunkin, A. S. Greenberg: Omental and subcutaneous adipose tissues of obese subjects release interleukin-6: depot difference and regulation by glucocorticoid. *J Clin Endocrinol Metab* 83, 847-50, 1998

53. M. C. Alessi, F. Peiretti, P. Morange, M. Henry, G. Nalbone, I. Juhan-Vague: Production of plasminogen activator inhibitor 1 by human adipose tissue: possible link between visceral fat accumulation and vascular disease. *Diabetes* 46, 860-7, 1997

54. C. Karlsson, K. Lindell, M. Ottosson, L. Sjostrom, B. Carlsson, L. M. Carlsson: Human adipose tissue expresses angiotensinogen and enzymes required for its conversion to angiotensin II. *J Clin Endocrinol Metab* 83, 3925-9, 1998

55. J. N. Fain, P. S. Cheema, S. W. Bahouth, M. Lloyd Hiler: Resistin release by human adipose tissue explants in primary culture. *Biochem Biophys Res Commun* 300, 674-8, 2003

56. C. U. Niesler, K. Siddle, J. B. Prins: Human preadipocytes display a depot-specific susceptibility to apoptosis. *Diabetes* 47, 1365-8, 1998

57. H. Masuzaki et al.: Human obese gene expression. Adipocyte-specific expression and regional differences in the adipose tissue. *Diabetes* 44, 855-8, 1995

58. C. T. Montague, J. B. Prins, L. Sanders, J. E. Digby, S. O'Rahilly: Depot- and sex-specific differences in human leptin mRNA expression: implications for the control of regional fat distribution. *Diabetes* 46, 342-7, 1997

59. S. Cinti: The adipose organ: morphological perspectives of adipose tissues. *Proc Nutr Soc* 60, 319-28, 2001

60. Y. Matsuzawa, T. Funahashi, T. Nakamura: Molecular mechanism of metabolic syndrome X: contribution of adipocytokines adipocyte-derived bioactive substances. *Ann N Y Acad Sci* 892, 146-54, 1999

61. A. R. Saltiel: You are what you secrete. *Nat Med* 7, 887-8, 2001

62. P. Arner: The adipocyte in insulin resistance: key molecules and the impact of the thiazolidinediones. *Trends Endocrinol Metab* 14, 137-45, 2003

63. T. Yamauchi et al.: Cloning of adiponectin receptors that mediate antidiabetic metabolic effects. *Nature* 423, 762-9, 2003

64. G. J. Mick, X. Wang, K. McCormick: White adipocyte vascular endothelial growth factor: regulation by insulin. *Endocrinology* 143, 948-53, 2002

65. J. H. Mydlo, J. G. Kral, R. J. Macchia: Preliminary results comparing the recovery of basic fibroblast growth factor (FGF-2) in adipose tissue and benign and malignant renal tissue. *J Urol* 159, 2159-63, 1998

66. Hsueh W C, Mitchell B D, Aburomia R, Pollin T, Sakul H, Gelder E M, Michelsen B K, Wagner M J, St Jean P L, Knowler W C, Burns D K, Bell C J, Shuldiner A R: Diabetes in the Old Order Amish: characterization and heritability analysis of the Amish Family Diabetes Study. *Diabetes Care* 23:595-601, 2000

67. Bäckhed, F., Ding, H., Wang, T., Hooper, L. V., Koh, G. Y., Nagy, A., Semenkovich, C. F. & Gordon, J. I.: The gut microbiota as an environmental factor that regulates fat storage. *Proc. Natl. Acad. Sci. USA* 101:15718-15723, 2004

68. Turnbaugh P J, Ley R E, Mahowald M A, Magrini V, Mardis E R, Gordon J I: An obesity-associated gut microbiome with increased capacity for energy harvest. *Nature* 444(7122):1027-31, 2006

69. L. J. Hutley, A. C. Herington, W. Shurety, C. Cheung, D. A. Vesey, D. P. Cameron, J. B. Prins: Human adipose tissue endothelial cells promote preadipocyte proliferation. *Am J Physiol Endocrinol Metab* 281, E1037-44, 2001

70. Wolf, G: Gut Microbiota: A Factor in Energy Regulation. *Nutrition Reviews* 64(1):47-50, 2006

71. Cash H L, Whitham C V, Behrendt C L, Hooper L V: Symbiotic bacteria direct expression of an intestinal bactericidal lectin. *Science* 313(5790):1126-30, 2006

72. Hogan S P, Seidu L, Blanchard C, Groschwitz K, Mishra A, Karow M L, Ahrens R, Artis D, Murphy A J, Valenzuela D M, Yancopoulos G D, Rothenberg M E: Resistin-like molecule beta regulates innate colonic function: barrier integrity and inflammation susceptibility. *J Allergy Clin Immunol.* 118(1):257-68, 2006

73. Qin B, Qiu W, Avramoglu R K, Adeli K.: Tumor Necrosis Factor-{alpha} Induces Intestinal Insulin Resistance and Stimulates the Overproduction of Intestinal Apolipoprotein B48-Containing Lipoproteins. *Diabetes* 56(2):450-61, 2007

74. J. Janke, S. Engeli, K. Gorzelniak, F. C. Luft, A. M. Sharma: Mature adipocytes inhibit in vitro differentiation of human preadipocytes via angiotensin type 1 receptors. *Diabetes* 51, 1699-707, 2002

75. S. P. Weisberg, D. McCann, M. Desai, M. Rosenbaum, R. L. Leibel, A. W. Ferrante, Jr.: Obesity is associated with macrophage accumulation in adipose tissue. *J Clin Invest* 112, 1796-808, 2003

76. E. M. Nowicki, C. J. Billington, A. S. Levine, H. Hoover, A. Must, E. Naumova: Overweight, obesity, and associated disease burden in the Veterans Affairs ambulatory care population. *Mil Med* 168, 252-6, 2003

77. S. K. Fried, C. D. Russell, N. L. Grauso, R. E. Brolin: Lipoprotein lipase regulation by insulin and glucocorticoid in subcutaneous and omental adipose tissues of obese women and men. *J Clin Invest* 92, 2191-8, 1993

78. K. H. Kaestner, R. J. Christy, J. C. McLenithan, L. T. Braiterman, P. Cornelius, P. H. Pekala, M. D. Lane: Sequence, tissue distribution, and differential expression of mRNA for a putative insulin-responsive glucose transporter in mouse 3T3-L1 adipocytes. *Proc Natl Acad Sci USA* 86:3150-4, 1989

79. Federico L M, Naples M, Taylor D, Adeli K.: Intestinal insulin resistance and aberrant production of apolipoprotein B48 lipoproteins in an animal model of insulin resistance and metabolic dyslipidemia: evidence for activation of protein tyrosine phosphatase-1B, extracellular signal-related kinase, and sterol regulatory element-binding protein-1c in the fructose-fed hamster intestine. *Diabetes* 55(5):1316-26, 2006

80. Shehadeh N, Sukhotnik I, Shamir R.: Gastrointestinal tract as a target organ for orally administered insulin. *J Pediatr Gastroenterol Nutr.* 43(3):276-81. Review, 2006

81. Shamir R, Shehadeh N, Rosenblat M, Eshach-Adiv O, Coleman R, Kaplan M, Hamoud S, Lischinsky S, Hayek T.: Oral insulin supplementation attenuates atherosclerosis progression in apolipoprotein E-deficient mice. *Arterioscler Thromb Vasc Biol.* 23(1):104-10, 2003

82. Matsukawa A, Hogaboam C M, Lukacs N W, Lincoln P M, Evanoff H L, Strieter R M, Kunkel S L.: Expression and contribution of endogenous IL-13 in an experimental model of sepsis. *J Immunol.* 164(5):2738-44, 2000

83. Fukuhara A, Matsuda M, Nishizawa M, Segawa K, Tanaka M, Kishimoto K, Matsuki Y, Murakami M, Ichisaka T, Murakami H, Watanabe E, Takagi T, Akiyoshi M, Ohtsubo T, Kihara S, Yamashita S, Makishima M, Funahashi T, Yamanaka S, Hiramatsu R, Matsuzawa Y, Shimomura I.: Visfatin: a protein secreted by visceral fat that mimics the effects of insulin. *Science* 307(5708):426-430, 2005

84. Berndt J, Kloting N, Kralisch S, Kovacs P, Fasshauer M, Schon M R, Stumvoll M, Bluher M.: Plasma visfatin concentrations and fat depot-specific mRNA expression in humans. *Diabetes* 54(10):2911-6, 2005

85. Pagano C, Pilon C, Olivieri M, Mason P, Fabris R, Serra R, Milan G, Rossato M, Federspil G, Vettor R.: Reduced plasma visfatin/pre B-cell colony enhancing factor in obesity is not related to insulin resistance in humans. *J Clin Endocrinol Metab.* 91(8):3165-70, 2006

86. Yang, R. Z., Lee, M. J., Hu, H., Pray, J. E., Wu, H. B., Hansen, B. C., Fried, S. K., Shuldiner, A. R., McLenithan, J. C., Gong, D. W.: Identification of Omentin as a novel depot-specific adipokine in human adipose tissue: possible role in modulating insulin action. *Am J Physiol Endocrinol Metab.* 290(6):E1253-61, 2006

87. De Souza Batista, C. M., Yang, R. Z., Lee, M. J., Glynn, N. M., YU, D. Z., Pray, J. E., Ndubuizu, K., Patil, S., Schwartz, A., Kligman, M., Fried, S. K., Gong, D. W., Shuldiner, A. R., Polllin, T, I., McLenithan, J. C.: Omentin Plasma Levels and Gene Expression are Decreased in Obesity. *Diabetes* 56(6):1655-61, 2007

88. J. A. Johnson, S. K. Fried, F. X. Pi-Sunyer, J. B. Albu (2001) Impaired insulin action in subcutaneous adipocytes from women with visceral obesity, *Am J Physiol Endocrinol Metab* 280, E40-9, 2001

What is claimed is:

1. A method of predicting an increased risk of: obesity, obesity-dependent subacute inflammation, obesity-dependent atherosclerosis, obesity-dependent cardiovascular disease or an obesity-dependent metabolic disease in a subject, comprising:
(a) determining an amount of omentin 1 protein (SEQ ID NO:1) or both omentin 1 protein and omentin 2 protein (SEQ ID NO:3) in a sample from a subject, and
(b) comparing the amount of omentin 1 protein or both omentin 1 protein and omentin 2 protein determined in (a) to a corresponding subject-matched control value determined for a population of subjects without obesity, obesity-dependent subacute inflammation, obesity-dependent atherosclerosis, obesity-dependent cardiovascular disease or an obesity-dependent metabolic disease, wherein when the amount of omentin 1 protein or both omentin 1 protein and omentin 2 protein determined in (a) is statistically significantly less than the corresponding subject-matched control value, the subject is predicted to have an increased risk of obesity, obesity-dependent subacute inflammation, obesity-dependent atherosclerosis, obesity-dependent cardiovascular disease or an obesity-dependent metabolic disease.

2. The method of claim 1, wherein the sample is selected from the group consisting of a whole blood sample, a serum sample, a plasma sample, a stool sample, a small intestine tissue sample, a visceral adipose tissue sample or a subcutaneous adipose tissue sample.

3. The method of claim 1, wherein the obesity-dependent metabolic disease is a metabolic disease selected from the group consisting of pre-diabetes, type 1 diabetes, type 2 diabetes, hyperglycemia, hyperlipidemia, dyslipidemia, and hypertension.

4. The method of claim 1, wherein the obesity-dependent cardiovascular disease is a cardiovascular disease selected from the group consisting of coronary heart disease, cerebral arterial disease, peripheral vascular disease and peripheral artery disease.

5. The method of claim 1, wherein the amount of protein is determined via chromatography, mass spectroscopy, or an immune-based assay selected from the group consisting of western blot analysis, ELISA and RIA.

6. The method of claim 1, wherein an amount of omentin 1 protein is determined and compared to a corresponding subject-matched control value.

* * * * *

UNITED STATES PATENT AND TRADEMARK OFFICE
CERTIFICATE OF CORRECTION

| | | |
|---|---|---|
| PATENT NO. | : 8,058,014 B2 | Page 1 of 1 |
| APPLICATION NO. | : 12/443146 | |
| DATED | : November 15, 2011 | |
| INVENTOR(S) | : Da-Wei Gong et al. | |

It is certified that error appears in the above-identified patent and that said Letters Patent is hereby corrected as shown below:

Column 1, lines 14-19, replace the text reading: "This invention was made in part with government support by National Institutes of Health Grant Nos. DK-620931983, AG20116 and P30DK072488, and the Veterans Administration, Geriatrics Research and Education Clinical Center (GRECC). The U.S. Government has certain rights in this invention." with the following text: --This invention was made with government support under Grant Numbers DK062093, AG020116, and DK072488 awarded by the National Institutes of Health and funding from the Veterans Administration, Geriatrics Research and Education Clinical Center (GREEC). The government has certain rights in the invention.--

Signed and Sealed this
Third Day of January, 2012

David J. Kappos
*Director of the United States Patent and Trademark Office*

SEQUENCE LISTING

<160> NUMBER OF SEQ ID NOS: 14

<210> SEQ ID NO 1
<211> LENGTH: 313

<212> TYPE: PRT
<213> ORGANISM: Homo sapiens

<400> SEQUENCE: 1

Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
            20                  25                  30

Ser Ser Pro Ser Leu Pro Arg Ser Cys Lys Glu Ile Lys Asp Glu Cys
        35                  40                  45

Pro Ser Ala Phe Asp Gly Leu Tyr Phe Leu Arg Thr Glu Asn Gly Val
    50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Gly Tyr Phe
            260                 265                 270

Pro Glu Ala Ser Pro Gln Gln Cys Gly Asp Phe Ser Gly Phe Asp Trp
        275                 280                 285

Ser Gly Tyr Gly Thr His Val Gly Tyr Ser Ser Ser Arg Glu Ile Thr
    290                 295                 300

Glu Ala Ala Val Leu Leu Phe Tyr Arg
305                 310

<210> SEQ ID NO 2
<211> LENGTH: 1284
<212> TYPE: DNA
<213> ORGANISM: Homo sapiens

<400> SEQUENCE: 2
ggcattgtgc cagggagggg tgaggctgga aaccttggtt ggccccactg ggcttcctcc      60
ataaagcttt ctgcacctca ttccacatca ggagcgtttt tggagaaagc tgcactctgt     120
tgagctccag ggcgcagtgg agggagggag tgaggagct ctctgtaccc aaggaaagtg     180
cagctgagac tcagacaaga ttacaatgaa ccaactcagc ttcctgctgt ttctcatagc     240

```
gaccaccaga ggatggagta cagatgaggc taatacttac ttcaaggaat ggacctgttc      300
ttcgtctcca tctctgccca gaagctgcaa ggaaatcaaa gacgaatgtc ctagtgcatt      360
tgatggcctg tattttctcc gcactgagaa tggtgttatc taccagacct tctgtgacat      420
gacctctggg ggtggcggct ggaccctggt ggccagcgtg catgagaatg acatgcgtgg      480
gaagtgcacg gtgggcgatc gctggtccag tcagcagggc agcaaagcag actacccaga      540
gggggacggc aactgggcca actacaacac ctttggatct gcagaggcgg ccacgagcga      600
tgactacaag aaccctggct actacgacat ccaggccaag gacctgggca tctggcacgt      660
gcccaataag tcccccatgc agcactggag aaacagctcc ctgctgaggt accgcacgga      720
cactggcttc ctccagacac tgggacataa tctgtttggc atctaccaga aatatccagt      780
gaaatatgga gaaggaaagt gttggactga caacggcccg tgatccctg tggtctatga      840 ttttggcgac gcccagaaaa cagcatctta ttactcaccc tatggccagc gggaattcac      900
tgcgggattt gttcagttca gggtatttaa taacgagaga gcagccaacg ccttgtgtgc      960
tggaatgagg gtcaccggat gtaacactga gcaccactgc attggtggag gaggatactt     1020
tccagaggcc agtccccagc agtgtggaga ttttctggt tttgattgga gtggatatgg     1080
aactcatgtt ggttacagca gcagccgtga gataactgag gcagctgtgc ttctattcta     1140
tcgttgagag ttttgtggga gggaacccag acctctcctc ccaaccatga gatcccaagg     1200
atggagaaca acttacccag tagctagaat gttaatggca gaagagaaaa caataaatca     1260
tattgactca aaaaaaaaaa aaaa                                            1284
```

<210> SEQ ID NO 3
<211> LENGTH: 325
<212> TYPE: PRT
<213> ORGANISM: Homo sapiens

<400> SEQUENCE: 3

```
Met Leu Ser Met Leu Arg Thr Met Thr Arg Leu Cys Phe Leu Leu Phe
1               5                   10                  15

Phe Ser Val Ala Thr Ser Gly Cys Ser Ala Ala Ala Ala Ser Ser Leu
            20                  25                  30

Glu Met Leu Ser Arg Glu Phe Glu Thr Cys Ala Phe Ser Phe Ser Ser
        35                  40                  45

Leu Pro Arg Ser Cys Lys Glu Ile Lys Glu Arg Cys His Ser Ala Gly
    50                  55                  60

Asp Gly Leu Tyr Phe Leu Arg Thr Lys Asn Gly Val Val Tyr Gln Thr
65                  70                  75                  80

Phe Cys Asp Met Thr Ser Gly Gly Gly Gly Trp Thr Leu Val Ala Ser
                85                  90                  95

Val His Glu Asn Asp Met Arg Gly Lys Cys Thr Val Gly Asp Arg Trp
            100                 105                 110

Ser Ser Gln Gln Gly Asn Lys Ala Asp Tyr Pro Glu Gly Asp Gly Asn
        115                 120                 125

Trp Ala Asn Tyr Asn Thr Phe Gly Ser Ala Glu Ala Ala Thr Ser Asp
    130                 135                 140

Asp Tyr Lys Asn Pro Gly Tyr Tyr Asp Ile Gln Ala Lys Asp Leu Gly
145                 150                 155                 160

Ile Trp His Val Pro Asn Lys Ser Pro Met Gln His Trp Arg Asn Ser
                165                 170                 175

Ala Leu Leu Arg Tyr Arg Thr Asn Thr Gly Phe Leu Gln Arg Leu Gly
            180                 185                 190
```

His Asn Leu Phe Gly Ile Tyr Gln Lys Tyr Pro Val Lys Tyr Arg Ser
            195                 200                 205

Gly Lys Cys Trp Asn Asp Asn Gly Pro Ala Ile Pro Val Val Tyr Asp
        210                 215                 220

Phe Gly Asp Ala Lys Lys Thr Ala Ser Tyr Tyr Ser Pro Tyr Gly Gln
225                 230                 235                 240

Arg Glu Phe Val Ala Gly Phe Val Gln Phe Arg Val Phe Asn Asn Glu
                245                 250                 255

Arg Ala Ala Asn Ala Leu Cys Ala Gly Ile Lys Val Thr Gly Cys Asn
            260                 265                 270

Thr Glu His His Cys Ile Gly Gly Gly Phe Pro Gln Gly Lys
            275                 280                 285

Pro Arg Gln Cys Gly Asp Phe Ser Ala Phe Asp Trp Asp Gly Tyr Gly
        290                 295                 300

Thr His Val Lys Ser Ser Cys Ser Arg Glu Ile Thr Glu Ala Ala Val
305                 310                 315                 320

Leu Leu Phe Tyr Arg
            325

<210> SEQ ID NO 4
<211> LENGTH: 1150
<212> TYPE: DNA
<213> ORGANISM: Homo sapiens

<400> SEQUENCE: 4 gcagggagc tccgagtgtc cacaggaagg gaactatcag ctcctggcat ctgtaaggat      60
gctgtccatg ctgaggacaa tgaccagact ctgcttcctg ttattcttct ctgtggccac     120
cagtgggtgc agtgcagcag cagcctcttc tcttgagatg ctctcgaggg aattcgaaac    180
ctgtgccttc tccttttctt ccctgcctag aagctgcaaa gaaatcaagg aacgctgcca    240
tagtgcaggt gatggcctgt attttctccg caccaagaat ggtgttgtct accagacctt    300
ctgtgacatg acttctgggg gtggcggctg gaccctggtg ccagcgtgc acgagaatga    360 catgcgtggg aagtgcacgg tgggtgatcg ctggtccagt cagcagggca caaagcaga    420 ctacccagag ggggatggca actgggccaa ctacaacacc tttggatctg cagaggcggc    480
cacgagcgat gactacaaga accctggcta ctacgacatc caggccaagg acctgggcat    540
ctggcatgtg cccaacaagt cccccatgca gcattggaga acagcgccc tgctgaggta    600 ccgcaccaac actggcttcc tccagagact gggacatataa tgtttggca tctaccagaa    660 atacccagtg aaatacagat cagggaaatg ttgaatgac aatggcccag ccatacctgt    720
ggtctatgac tttggtgatg ctaagaagac tgcatcttat tactcaccgt atggtcaacg    780
ggaatttgtt gcaggattcg ttcagttccg ggtgtttaat aacgagagag cagccaacgc    840
cctttgtgct gggataaaag ttactggctg taacactgag catcactgca tcggtggagg    900
agggttcttc ccacagggca aaccccgtca gtgtgggac ttctccgcct tgactggga    960 tggatatgga actcacgtta agagcagctg cagtcgggag ataacggagg cggctgtact   1020
cttgttctat agatgagaca gagctctgcg gtgtcagggc gagaaccatt cttccaaccc   1080
cggctatttg gagacggaaa aactggaatt ctaacaagga ggagaggaga ctaaatcaca   1140
tcaatttgca                                                                 1150

<210> SEQ ID NO 5
<211> LENGTH: 15
<212> TYPE: PRT

```
<213> ORGANISM: Artificial Sequence
<220> FEATURE:
<223> OTHER INFORMATION: chemically synthesized omentin 1 peptide

<400> SEQUENCE: 5

Thr Thr Arg Gly Trp Ser Thr Asp Glu Ala Asn Thr Tyr Phe Cys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: chemically synthesized omentin 1 peptide

<400> SEQUENCE: 6

Ser Gln Gln Gly Ser Lys Ala Val Tyr Pro Glu Gly Asp Gly Cys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: chemically synthesized omentin 1 peptide

<400> SEQUENCE: 7

Gly Ser Ala Glu Ala Ala Thr Ser Asp Asp Tyr Lys Asn Pro Cys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: chemically synthesized omentin 1 peptide

<400> SEQUENCE: 8

Val Pro Asn Lys Ser Pro Met Gln His Trp Arg Asn Ser Ser Cys
1               5                   10                  15

<210> SEQ ID NO 9
<211> LENGTH: 2102
<212> TYPE: DNA
<213> ORGANISM: Homo sapiens

<400> SEQUENCE: 9
agttaacagg ctggctcggt ggttcacgcc cgtaatccta gcacttgggc aagctgaggc      60
aggaggatca aggtcaggag ttctggagta gcctgggtaa catggggaga ccccgtttct    120
acagaaaaga aaagagtttt ttttgttttt tgttttttttt gagatggagt ttcactcttg   180
ttgcccaggc tggagtgcaa tggtgtgatc tcggctcact gcaacctccg cctcctggat    240
tcaggtgatt ctcctgcctc agcctcctga gtagctggga ttacaggcat gcaccaccac    300
gaccggctaa ttttgtattt ttagtagaga ccgggtttct ccatgttggt caggctggtc    360
tcgatctttt gacctcagat gatccaccca cctcggcctc ccaaagtgct gggattacag    420
gcgtgagcca ccgcgcccag cccaaaaaaa gagtttttaa taatatgatg ttgataattg    480
tactgtggtt atacatgaca tattcctatt attagaaaac acactagttg gccaggcatg    540
gtggcttaca cctataatcc cagcacttgg gaggccgagg caggtggatc acgaggtcac    600
gagttcaaga ccagcctggc caagatggca aaacccgta tctactaaaa atacaaaaat     660
tagctgggcg tggtggtggg tgcctgtaat cccagttact cgggaggctg agacaggaga    720
```

-continued

| | |
|---|---|
| atcacttgaa cctgggaggc gggggttgca gtaagctgag accatgccat tgcactccaa | 780 |
| cctgggtgac agagtgaggc tctgtgtcaa aaaacaaaac aaaataaaaa aaacccatac | 840 |
| gcatttattt aaaggtaaaa gcccatgatg tatgtacctt accttcaaat ggttcagaaa | 900 |
| aaaattttgt gtgtgtgggt gtattttata tacatatatc tatatatata tagagagaga | 960 |
| gagagagaac acgaaagata aagcaaatgg ggtgaaatat taacaatagt tgaatctagg | 1020 |
| taaagggcat atatgtggct ttatattatt gttattttg caacatttaa taaatttcaa | 1080 |
| attgtttcta aacagagtta ataaaacaat aaaattacag caggatacat gcaataatta | 1140 |
| gtgtttggac agtgtatagt gtggacaaag gaaggatcca tcagctttgt ctggtgatgg | 1200 |
| gggtgtcagg gaaggcctca tagagaaatt ggaggaaaga ttggaaggat gatgtcttct | 1260 |
| tttcccattt atttattatt attattatta ttattatttt gaggtgaagt cttgctctgt | 1320 |
| tgcccaggct ggagtgcagt ggagcagtct ggctcactg caacctccac ctcctgggtt | 1380 |
| caagcagttc tcctgtctca gcctccagag tagctgggat tacgggtgca cgccactgca | 1440 |
| cccagctaaa ttttgtatt tttagtagag acaggggttgc accatgttgg ctggtcttga | 1500 |
| actcctgacc tcaggtaatc cgcccacctc ggcctcccaa agcgctatga ttataggtgt | 1560 |
| gagccactgt gcctggccaa ttattattct taattaatta atttatttt catgaggtgt | 1620 |
| cacctcagtc taaaaggatg atttcttgac agagttgtgt ctaggggggcc agggcatctg | 1680 |
| ggggaggtgg gagagggaga acgcagggga ggattgtgac ctatccacga atctgattag | 1740 |
| atactgctac attgtatggc ctgccttggc aaagcaggat gcccctcctc agatggcgac | 1800 |
| agtcacctgt gtggccagga acacagctcc ctgctcctcc agccagtcgc acgtcctttc | 1860 |
| tcatttccac ggtcccaggc tcaggtaccc tcagagggaa gggcttcaga ggaggggct | 1920 |
| agcagcctag gctgctcagg gttgggctgg gcagggctca ggtggtttgg ctctccacag | 1980 |
| ctctccacat aaagggacca gcacttcacc cttcatcagg atcctctgca ggggagctcc | 2040 |
| gagtgtccac aggaagggaa ctatcagctc ctggcatctg taaggatgct gtccatgctg | 2100 |
| gt | 2102 |

<210> SEQ ID NO 10
<211> LENGTH: 1384
<212> TYPE: DNA
<213> ORGANISM: Homo sapiens

<400> SEQUENCE: 10

| | |
|---|---|
| atacctgtgg tctatgactt tggtgatgct aagaagactg catcttatta ctcaccgtat | 60 |
| ggtcaacgtg agtgtttgct ccctaagtcc agtcataaat attttcttgt actcttggag | 120 |
| aatggtggca ataacaaca attaataatt gctagtattt actgagcact taaaatgcac | 180 |
| cagactcttg tcttggaact taacatgatt ttgtgtcatt taattaccat gagaaaacta | 240 |
| tgaagttaga attgctgtta tccccatttc acagcacgta atcccaggtt tcttcatcac | 300 |
| caccttgtat actcttataa ttgtggggaa aagaaaaaga gatcagactg ttactgtgtc | 360 |
| tatgtagaaa gaagtagaca taagagactc cattttggtc tgtgctgaga aaaattcttc | 420 |
| tgccttgaga tgctgttaat ctgtaaccct acccccaacc ctgtgctcac agagacatgt | 480 |
| gctgtgttga ctcacggttt aatggattta gggctgtgca ggatgtgctt tgttaaacaa | 540 |
| gtgcttgaag gcagcatgct tgttaaaggt catcaccact ctctaatctc aagtacccag | 600 |
| ggacacaata cactgcggaa ggccgcaggg acctctgtct aggaaagcca ggtattgtcc | 660 |
| aaggtttctc cccatgtgat agcctgagat atggcctcgt gggaagggaa agacctgact | 720 |

-continued

```
gtcccccagc cgacaccca caaagggtct gtgctgagga ggattagtaa aagaggaagg    780
cctctttgca gttgagataa gaggaaggca tctgtcttct gcttatccct gggcaatgga    840
atgttttggt gtaaaacccg attgtatgtt ctatttactg agataggaga aaaccacctt    900
agggctggag gtgagacatg ctggcggcaa tactgctttt taatgcaccg agatgtttat    960
gtatgtgcac gtcaaaagca cagcaccttt tcttaacctt gtttatgaca cagacatttg   1020
ttcacatgtt ttcctgctga ccctctcccc actattaccc tattgtcctg ccacgtcccc   1080
ctctctgaga tggtagagat aatgatcaat aaatactgag ggaactcaga gactggtgct   1140
ggtgcgggtc ctccttatgc tgagcgccag tccctgggc ccactttct ttctctatac    1200 tttgtcgctg tgtctctttc ttttctcagt ctctcgttcc acccaacgag gaacacccac   1260
aggtgtggag gggcaggcca ccccttcaat aatagttaag aaaaggtgca tacaaaacat   1320
tagctgggca tgatggcgca tgcctgtaat cccagctcct cgggaggctg aggcaggaga   1380
atct                                                               1384
```

<210> SEQ ID NO 11
<211> LENGTH: 19
<212> TYPE: DNA
<213> ORGANISM: Artificial Sequence
<220> FEATURE:
<223> OTHER INFORMATION: chemically synthesized amplification primer

<400> SEQUENCE: 11
ctccagacac tgggacata                                                   19

<210> SEQ ID NO 12
<211> LENGTH: 19
<212> TYPE: DNA
<213> ORGANISM: Artificial Sequence
<220> FEATURE:
<223> OTHER INFORMATION: chemically synthesized amplification primer

<400> SEQUENCE: 12
tgaccctcat tccagcaca                                                   19

<210> SEQ ID NO 13
<211> LENGTH: 20
<212> TYPE: DNA
<213> ORGANISM: Artificial Sequence
<220> FEATURE:
<223> OTHER INFORMATION: chemically synthesized amplification primer

<400> SEQUENCE: 13
cgacctggaa gtccaactac                                                  20

<210> SEQ ID NO 14
<211> LENGTH: 18
<212> TYPE: DNA
<213> ORGANISM: Artificial Sequence
<220> FEATURE:
<223> OTHER INFORMATION: chemically synthesized amplification primer

<400> SEQUENCE: 14
atctgctgca tctgcttg                                                    18